(12) United States Patent
Cepko et al.

(10) Patent No.: US 9,610,363 B2
(45) Date of Patent: Apr. 4, 2017

(54) METHODS FOR INHIBITING STARVATION OF A CELL

(75) Inventors: Constance L. Cepko, Newton, MA (US); Claudio Punzo, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 241 days.

(21) Appl. No.: 13/264,515

(22) PCT Filed: Apr. 15, 2010

(86) PCT No.: PCT/US2010/031211
§ 371 (c)(1),
(2), (4) Date: May 18, 2012

(87) PCT Pub. No.: WO2010/121010
PCT Pub. Date: Oct. 21, 2010

(65) Prior Publication Data
US 2012/0232130 A1 Sep. 13, 2012

Related U.S. Application Data

(60) Provisional application No. 61/169,835, filed on Apr. 16, 2009.

(51) Int. Cl.
*A61K 48/00* (2006.01)
*C12N 9/16* (2006.01)
*C12N 9/88* (2006.01)
*C12N 9/00* (2006.01)

(52) U.S. Cl.
CPC .............. *A61K 48/005* (2013.01); *C12N 9/16* (2013.01); *C12N 9/88* (2013.01); *C12N 9/93* (2013.01); *C12Y 301/03011* (2013.01); *C12Y 401/01032* (2013.01); *C12Y 604/01001* (2013.01); *C12N 2799/025* (2013.01); *C12N 2830/008* (2013.01); *C12N 2840/203* (2013.01)

(58) Field of Classification Search
None
See application file for complete search history.

(56) References Cited

U.S. PATENT DOCUMENTS

2003/0129164 A1* 7/2003 Flannery et al. ............ 424/93.2
2007/0203083 A1* 8/2007 Mootha et al. ................. 514/44
2007/0224648 A1    9/2007 Cox et al.
2011/0268705 A1   11/2011 Cepko et al.
2011/0318424 A1   12/2011 Cepko et al.

FOREIGN PATENT DOCUMENTS

WO    WO2002087557 A1 * 11/2002
WO    WO2008/127675 A1 * 10/2008

OTHER PUBLICATIONS

Irani, et al. Improvement of the Primary Metabolism of Cell Cultures by Introducing a New Cytoplasmic Pyruvate Carboxylase Reaction. Biotechnology and Bioengineering 1999, 66(4):238-246.*
Goldman. Gluconeogenesis in the Amphibian Retina. Biochem. J. 1988, 254(2):359-365; abstract.*
Simpson, et al. Decreased Concentrations of GLUT1 and GLUT3 Glucose Transporters in the Brains of Patients with Alzheimer's Disease. Annals of Neurology 1994, 35(5):546-551; abstract; p. 546, col. 1, para 1; p. 548, col. 1, para 1.*
Punzo et al. Nature Neuroscience 12, 44-52 (2008) Published online: Dec. 7, 2008 | doi:10.1038/nn.2234 Stimulation of the insulin/mTOR pathway delays cone death in a mouse model of retinitis pigmentosa Claudio Punzo1, Karl Kornacker2 & Constance L Cepko1,3.*
WO2002087557A1—German to English translation of claims from Espacenet.*
Eckmiller (2003) Retinal DegenerationsAdvances in Experimental Medicine and Biologyvol. 533, 2003, pp. 277-285.*
Zheng et al. Proteomics 2009;9:1869-82.*
Mazzio et al. NeuroToxicol 2003;24:137-47.*
Miceli et al. Exp Cell Res 2005;302:270-80.*
Cuenca et al. Prog Retin Eye Res 2014;43:17-75.*
Kumar-Singh, Vision Res. 2008;48: 1671-1680.*
Kondoh et al. Histol Histopathol 2007;22:85-90.*
Casson et al. Arch Ophthalmol 2004;122:361-6.*
Sola et al. Brain Res 1996;741:294-9.*
Yoo et al. IOVS 2004;45:1523-30.*
Montana et al. Pharmacogenomics 2008;9:335-47.*
Hsu et al., "Glycolytic Enzymes and a GLUT-1 Glucose Transporter in the Outer Segments of; Rod and Cone Photoreceptor Cell". JBC (1991) 266(32):21745-21752.
Scholz et al., Lipid Metabolism by Rat Lung in vitro, Biochem. J. (1971) 124(2):257-264.
Weber et al., "Recombinant Adeno-associated Virus Serotype 4 Mediates Unique and; Exclusive Long-Term Transduction of Retinal Pigmented Epithelium in Rat, Dog, and; Nonhuman Primate after Subretinal Delivery", Molecular Therapy (2003) 7(6):774-781.
Madreperla et al., "Visual Acuity Loss in Retinitis Pigmentosa", *Arch Ophthalmol* (1990) 108, 358-61.
Punzo et al., "Cellular Responses to Photoreceptor Death in the rd1 Mouse Model of Retinal Degeneration", IOVS (2007) 48 (2): 849-857.
John et al., "Loss of cone molecular markers in rhodopsin-mutant human retinas with retinitis pigmentosa", *Mol Vis* (2000) 6, 204-15.
Yu et al., "Retinal degeneration and local oxygen metabolism", *Exp Eye Res* (2005) 80, 745-51.
Corrochano et al., "Attenuation of Vision Loss and Delay in Apoptosis of Photoreceptors Induced by Proinsulin in a Mouse Model of Retinitis Pigmentosa," *Invest Ophthalmol Vis Sci* (2008) 49, 4188-94.
Chen et al., "HDAC4 regulates neuronal survival in normal and diseased retinas", *Science* (2009) 323:256-9.
Punzo et al., "Stimulation of the insulin/mTOR pathway delays cone death in a mouse model of retinitis pigmentosa", *Nat Neurosci.* (2009) (1):44-52.

* cited by examiner

*Primary Examiner* — Janice Li
(74) *Attorney, Agent, or Firm* — McCarter & English, LLP; Maria Laccotripe Zacharakis; Deborah L. Nagle

(57) ABSTRACT

The present invention is directed to methods for the treatment or prevention of starvation in a cell, e.g., a neuronal cell, and methods for the treatment and prevention of disorders associated therewith by the administration of an agent, e.g., a nucleic acid molecule, which enhances the intracellular generation and/or uptake of glucose, pyruvate, lactate, and/or NADPH.

17 Claims, 38 Drawing Sheets

| Affymetrix ID | Gene Symbol | AVG_C0/R | AVG_C0/C1 | AVG_C0/C2 |
|---|---|---|---|---|
| 1425337_at | Slc12a5 | 5.42 | 3.64 | 4.41 |
| 1432646_a_at | BG640370 | 4.46 | 3.22 | 3.85 |
| 1425833_a_at | Hpca | 4.19 | 3.12 | 3.90 |
| 1425227_a_at | ATP6V0A1 | 3.93 | 2.49 | 3.41 |
| 1425405_a_at | ADAR | 3.83 | 3.28 | 3.65 |
| 1426562_a_at | Olfm1 | 3.69 | 3.06 | 3.03 |
| 1415824_at | SCD2 | 3.66 | 2.23 | 2.99 |
| 1429385_at | Wdr68 | 3.54 | 3.67 | 3.88 |
| 1427754_a_at | DNM1 | 3.54 | 2.19 | 3.01 |
| 1420833_at | VAMP2 | 3.46 | 2.15 | 3.36 |
| 1454735_at | Odf2 | 3.45 | 2.47 | 2.98 |
| 1431107_at | Stk35 | 3.39 | 2.45 | 3.40 |
| 1454106_a_at | Cxxc1 | 3.39 | 2.72 | 3.58 |
| 1421255_s_at | Cabp1 | 3.39 | 2.00 | 1.98 |
| 1421780_a_at | Cabp5 | 3.36 | 2.21 | 2.38 |
| 1425338_at | PLCB4 | 3.33 | 2.58 | 2.49 |
| 1421349_x_at | Cend1 | 3.31 | 2.09 | 2.56 |
| 1425711_a_at | AKT1 | 3.27 | 2.23 | 3.28 |
| 1425457_a_at | GRB10 | 3.23 | 2.62 | 3.19 |
| 1451056_at | PSMD7 | 3.23 | 2.37 | 2.22 |
| 1448541_at | Kns2 | 3.23 | 2.27 | 3.04 |
| 1425659_at | Tom1l2 | 3.21 | 2.54 | 3.36 |
| 1448997_at | Pscd1 | 3.18 | 2.67 | 3.01 |
| 1442138_at | Gpr63 | 3.14 | 1.93 | 1.98 |
| 1426115_a_at | Kcnj9 | 3.13 | 2.87 | 2.69 |
| 1450202_at | GRIN1 | 3.13 | 2.39 | 2.94 |
| 1428157_at | GNG2 | 3.12 | 2.95 | 3.22 |
| 1424359_at | OPLAH | 3.08 | 1.42 | 1.75 |
| 1418174_at | Dbp | 3.05 | 1.99 | 2.12 |
| 1426975_at | OS-9 | 2.97 | 2.63 | 3.11 |
| 1435276_a_at | Dgcr2 | 2.96 | 2.32 | 2.73 |
| 1449936_at | KIAA1467 | 2.94 | 1.87 | 2.30 |
| 1455410_at | Faim2 | 2.93 | 1.47 | 1.76 |
| 1453137_at | PPM1J | 2.93 | 2.16 | 2.38 |
| 1435770_at | Txndc13 | 2.93 | 2.37 | 2.61 |
| 1457914_at | unknown | 2.88 | 2.86 | 2.91 |
| 1458163_at | BC066028 | 2.86 | 2.10 | 1.89 |
| 1433714_at | SULT4A1 | 2.85 | 1.82 | 1.79 |
| 1436713_s_at | Gd2 | 2.84 | 2.09 | 2.52 |

FIG. 19A

| Affymetrix ID | Gene Symbol | AVG_C0/R | AVG_C0/C1 | AVG_C0/C2 |
|---|---|---|---|---|
| 1422756_at | SLC32A1 | 2.83 | 2.05 | 1.91 |
| 1452688_at | Prpf39 | 2.80 | 3.58 | 3.19 |
| 1421391_at | VIPR2 | 2.79 | 2.10 | 2.18 |
| 1446071_at | Steap2 | 2.78 | 1.86 | 2.02 |
| 1454891_at | CDS2 | 2.77 | 2.09 | 2.61 |
| 1421862_a_at | Vamp1 | 2.76 | 1.96 | 2.46 |
| 1440358_at | ARHGEF15 | 2.74 | 2.38 | 2.28 |
| 1431355_s_at | TRPM7 | 2.72 | 2.60 | 2.52 |
| 1422793_at | PAFAH1B2 | 2.72 | 2.28 | 2.78 |
| 1453199_at | Acbd6 | 2.71 | 2.09 | 2.23 |
| 1449615_s_at | Bdllbp | 2.69 | 2.64 | 3.06 |
| 1432329_a_at | MATK | 2.69 | 2.18 | 2.36 |
| 1459826_at | Kcnq2 | 2.68 | 2.37 | 2.59 |
| 1438305_at | C11ORF2 | 2.67 | 2.02 | 2.57 |
| 1426467_s_at | C1ORF123 | 2.63 | 2.35 | 2.74 |
| 1429761_at | Rtn1 | 2.62 | 2.39 | 2.27 |
| 1420148_at | SLC6A6 | 2.61 | 2.41 | 2.95 |
| 1426888_at | BHMT2 | 2.61 | 2.55 | 2.68 |
| 1451980_a_at | Mapre2 | 2.59 | 1.80 | 1.81 |
| 1450512_at | Ntn4 | 2.58 | 2.25 | 3.12 |
| 1415795_at | Spin | 2.57 | 2.49 | 2.59 |
| 1434467_at | Atcay | 2.57 | 2.13 | 2.21 |
| 1426738_at | DGKZ | 2.56 | 1.66 | 1.90 |
| 1419278_at | USP48 | 2.54 | 2.08 | 2.12 |
| 1417455_at | TGFB3 | 2.52 | 2.19 | 2.04 |
| 1427478_at | USP12 | 2.50 | 2.74 | 2.90 |
| 1437319_at | Unc13c | 2.48 | 1.67 | 1.54 |
| 1427004_at | Pbxo2 | 2.47 | 1.68 | 1.55 |
| 1450177_at | NGFR | 2.46 | 2.26 | 2.19 |
| 1415845_at | Syt4 | 2.46 | 1.78 | 1.82 |
| 1428717_at | Sem1 | 2.45 | 2.11 | 2.11 |
| 1439160_at | 4732496O08Rik | 2.44 | 2.27 | 2.46 |
| 1450686_at | Pon2 | 2.43 | 1.93 | 1.68 |
| 1415803_at | CX3CL1 | 2.43 | 1.33 | 1.83 |
| 1421189_at | GABRB3 | 2.43 | 1.84 | 2.49 |
| 1416936_at | Aatk | 2.42 | 1.67 | 1.84 |
| 1416190_a_at | Sec61a1 | 2.42 | 2.29 | 2.96 |
| 1452357_at | 5-Sep | 2.42 | 1.69 | 1.77 |
| 1450311_at | SLC8A3 | 2.41 | 2.10 | 2.51 |
| 1460384_a_at | Arl4b | 2.37 | 1.91 | 2.19 |
| 1434563_at | Rps6kc1 | 2.37 | 2.26 | 2.27 |
| 1450080_at | Cxx1c | 2.37 | 1.46 | 1.69 |
| 1444552_at | KIAA0240 | 2.36 | 2.28 | 2.28 |
| 1450055_at | Van1 | 2.35 | 1.51 | 1.47 |
| 1448498_at | RPS6KA4 | 2.35 | 1.69 | 1.65 |
| 1424045_at | C6ORF35 | 2.33 | 2.04 | 2.52 |
| 1460321_at | Cnm4 | 2.32 | 1.75 | 1.91 |
| 1420387_at | Mpv17 | 2.32 | 2.06 | 2.12 |

FIG. 19B

| Affymetrix ID | Gene Symbol | AVG_C0/R | AVG_C0/C1 | AVG_C0/C2 |
|---|---|---|---|---|
| 1422756_at | SLC33A1 | 2.83 | 2.05 | 1.91 |
| 1452688_at | Prpf39 | 2.80 | 2.58 | 3.19 |
| 1421391_at | VIPR2 | 2.79 | 2.10 | 2.18 |
| 1446071_at | Stmp2 | 2.78 | 1.86 | 2.02 |
| 1454891_at | CD52 | 2.77 | 2.09 | 2.61 |
| 1421862_a_at | Vamp1 | 2.76 | 1.96 | 2.46 |
| 1440358_at | ARHGEF15 | 2.74 | 2.38 | 2.29 |
| 1431355_s_at | TRPM7 | 2.73 | 2.60 | 2.82 |
| 1422793_at | PAFAH1B2 | 2.72 | 2.25 | 2.78 |
| 1453199_at | Abd6 | 2.71 | 2.09 | 2.23 |
| 1449615_s_at | Hdlbp | 2.69 | 2.64 | 3.06 |
| 1432329_a_at | MATK | 2.69 | 2.18 | 2.36 |
| 1459826_at | Kcnq2 | 2.68 | 2.37 | 2.59 |
| 1438205_at | C11ORF2 | 2.67 | 2.02 | 2.57 |
| 1426467_s_at | C1ORF123 | 2.63 | 2.35 | 2.74 |
| 1429761_at | Rin1 | 2.62 | 2.39 | 2.27 |
| 1420148_at | SLC6A6 | 2.61 | 2.41 | 2.95 |
| 1426688_at | EHMT2 | 2.61 | 2.45 | 2.68 |
| 1451989_a_at | Mapre2 | 2.59 | 1.80 | 1.81 |
| 1450512_at | Ntm4 | 2.58 | 2.25 | 2.12 |
| 1415793_at | Spin | 2.57 | 2.49 | 2.39 |
| 1434467_at | Atcay | 2.57 | 2.13 | 2.21 |
| 1426738_at | DGKZ | 2.56 | 1.66 | 1.90 |
| 1419278_at | USP48 | 2.54 | 2.08 | 2.12 |
| 1417455_at | TGFB3 | 2.52 | 2.19 | 2.04 |
| 1427478_at | USP12 | 2.50 | 2.74 | 2.99 |
| 1437319_at | Unc13c | 2.48 | 1.67 | 1.54 |
| 1427004_at | Fbxo2 | 2.47 | 1.68 | 1.55 |
| 1459377_at | NGFR | 2.46 | 2.26 | 2.19 |
| 1418868_at | Syt4 | 2.46 | 1.78 | 1.82 |
| 1428717_at | Sem1 | 2.45 | 2.11 | 2.11 |
| 1439160_at | 4732496O08Rik | 2.44 | 2.27 | 2.46 |
| 1450686_at | Pen2 | 2.43 | 1.93 | 1.68 |
| 1415803_at | CX3CL1 | 2.43 | 1.33 | 1.83 |
| 1421189_at | GABRB3 | 2.43 | 1.84 | 2.49 |
| 1416936_at | Aatk | 2.42 | 1.67 | 1.84 |
| 1416180_a_at | Sec61a1 | 2.42 | 2.29 | 2.96 |
| 1452357_at | 5-Sep | 2.42 | 1.69 | 1.77 |
| 1450311_at | SLC8A3 | 2.41 | 2.10 | 2.51 |
| 1460384_a_at | Arid4b | 2.37 | 1.91 | 2.19 |
| 1434563_at | Rps6kc1 | 2.37 | 2.26 | 2.27 |
| 1458080_at | Cxxc | 2.37 | 1.46 | 1.69 |
| 1444552_at | KIAA0240 | 2.36 | 2.28 | 2.28 |
| 1450035_at | Vsnl1 | 2.35 | 1.51 | 1.47 |
| 1448498_at | RPS6KA4 | 2.35 | 1.60 | 1.65 |
| 1424045_at | C6ORF35 | 2.33 | 2.04 | 2.52 |
| 1460321_at | Camk4 | 2.32 | 1.75 | 1.91 |
| 1420387_at | Mpv17 | 2.32 | 2.06 | 2.32 |

FIG. 19C

| Affymetrix ID | Gene Symbol | AVG_C0/R | AVG_C0/C1 | AVG_C0/C2 |
|---|---|---|---|---|
| 1460661_at | EDG3 | 2.01 | 1.90 | 2.50 |
| 1417103_at | DDT | 2.01 | 1.33 | 1.59 |
| 1430632_at | LOC433749 | 2.00 | 2.11 | 2.35 |
| 1419746_at | Arhgap23 | 2.00 | 1.84 | 1.95 |
| 1426465_at | Dlgap4 | 2.00 | 1.67 | 1.67 |
| 1429187_at | Traed7 | 2.00 | 2.15 | 2.23 |
| 1418297_at | Dpysl4 | 2.00 | 1.98 | 2.03 |
| 1439031_s_at | MARK4 | 1.99 | 1.78 | 2.01 |
| 1424928_at | C11ORF30 | 1.98 | 1.97 | 2.06 |
| 1423802_at | Camkv | 1.97 | 1.27 | 1.13 |
| 1456869_at | Zfp787 | 1.97 | 1.84 | 2.07 |
| 1453068_at | 2300002D11Rik | 1.96 | 1.42 | 1.49 |
| 1416597_at | Bdgfrp2 | 1.96 | 1.69 | 1.65 |
| 1421971_a_at | Mrps34 | 1.95 | 1.42 | 1.45 |
| 1433921_s_at | Dpk3 | 1.94 | 2.00 | 2.33 |
| 1429036_at | Osrp3 | 1.94 | 2.41 | 3.05 |
| 1419753_at | Nix1 | 1.90 | 1.57 | 1.85 |
| 1439375_x_at | ALDOA | 1.89 | 1.79 | 1.65 |
| 1429943_a_at | PDE1C | 1.89 | 1.48 | 1.39 |
| 1434554_at | Trim37 | 1.88 | 1.96 | 2.22 |
| 1433117_a_at | RBJ | 1.88 | 1.59 | 1.39 |
| 1436775_a_at | Ankrd17 | 1.86 | 1.69 | 1.56 |
| 1427408_a_at | Tbrap3 | 1.86 | 1.87 | 2.09 |
| 1449263_at | Ufm1 | 1.86 | 2.10 | 2.14 |
| 1424914_at | KIAA1737 | 1.84 | 1.82 | 1.39 |
| 1450878_at | Sri | 1.83 | 1.53 | 1.61 |
| 1434027_at | Dscr1l2 | 1.83 | 1.52 | 1.67 |
| 1434027_at | RCAN3 | 1.83 | 1.52 | 1.67 |
| 1426343_at | STT3B | 1.82 | 2.04 | 2.46 |
| 1452730_at | Rps4y2 | 1.81 | 1.52 | 2.03 |
| 1423014_a_at | CLYBL | 1.79 | 1.54 | 1.66 |
| 1438016_at | Dkc1 | 1.79 | 1.38 | 1.23 |
| 1451364_at | Polr3gl | 1.78 | 1.71 | 1.68 |
| 1460363_at | Parc6c | 1.78 | 1.97 | 1.82 |
| 1450472_s_at | SMAD3 | 1.78 | 1.38 | 1.83 |
| 1417363_at | Zfp61 | 1.77 | 1.91 | 1.70 |
| 1448646_at | Wdr12 | 1.77 | 1.60 | 1.56 |
| 1417259_a_at | Can2b | 1.77 | 1.74 | 1.98 |
| 1426306_a_at | Maged2 | 1.76 | 1.91 | 1.85 |
| 1460393_at | St13 | 1.73 | 2.34 | 2.73 |
| 1433539_at | Commd3 | 1.71 | 1.89 | 1.99 |
| 1454987_a_at | H2-Ke6 | 1.71 | 1.88 | 1.73 |
| 1415978_at | Tubb3 | 1.71 | 1.70 | 1.72 |
| 1417128_at | Pick1o1 | 1.70 | 1.52 | 1.50 |
| 1424776_a_at | Slc25a28 | 1.70 | 1.60 | 1.49 |
| 1418632_at | UBE2H | 1.69 | 1.27 | 2.07 |
| 1422456_at | NSF | 1.68 | 1.46 | 1.40 |
| 1422679_s_at | Ctr9 | 1.67 | 2.06 | 2.07 |

FIG. 19D

| Affymetrix ID | Gene Symbol | AVG_C0/R | AVG_C0/C1 | AVG_C0/C2 |
|---|---|---|---|---|
| 1433009_at | Slc9a6 | 1.67 | 1.64 | 1.92 |
| 1435525_at | Kcnj17 | 1.65 | 1.40 | 1.43 |
| 1431212_a_at | TRMT6 | 1.64 | 2.05 | 1.92 |
| 1427077_a_at | AP2B1 | 1.63 | 1.89 | 2.01 |
| 1416284_at | Mrpl28 | 1.61 | 1.72 | 1.66 |
| 1415974_at | MAP2K2 | 1.61 | 1.71 | 1.65 |
| 1415956_a_at | PCTK1 | 1.61 | 1.46 | 1.80 |
| 1427073_at | Lace1 | 1.61 | 1.30 | 1.23 |
| 1435698_at | Rictor | 1.60 | 1.48 | 1.50 |
| 1425068_a_at | Tex264 | 1.60 | 1.89 | 1.80 |
| 1418432_at | Cab39 | 1.60 | 1.60 | 1.56 |
| 1432464_a_at | KIAA1543 | 1.60 | 1.43 | 1.54 |
| 1427258_at | Trim24 | 1.59 | 1.79 | 2.00 |
| 1427030_at | Txndc16 | 1.58 | 1.65 | 1.66 |
| 1422510_at | Cidspl | 1.58 | 1.38 | 1.33 |
| 1417223_at | Cd2bp2 | 1.57 | 1.39 | 1.34 |
| 1417148_at | PDGFRB | 1.57 | 1.47 | 1.41 |
| 1417063_at | C1QB | 1.56 | 2.26 | 2.57 |
| 1453269_at | Brf1 | 1.55 | 1.55 | 1.69 |
| 1417304_at | CALB1 | 1.55 | 1.26 | 1.36 |
| 1449087_at | TXNRD2 | 1.55 | 1.45 | 1.45 |
| 1427149_at | Plekha6 | 1.55 | 1.36 | 1.27 |
| 1417870_x_at | Ctsz | 1.55 | 1.79 | 1.95 |
| 1448122_at | Tcp1 | 1.55 | 1.62 | 1.46 |
| 1438461_at | PPP2R5E | 1.54 | 1.65 | 1.68 |
| 1456867_x_at | Ergic3 | 1.53 | 1.72 | 1.93 |
| 1422489_at | GCS1 | 1.52 | 1.73 | 1.83 |
| 1427987_at | Safb2 | 1.50 | 1.41 | 1.14 |
| 1416403_at | DDOST | 1.50 | 1.56 | 1.71 |
| 1431137_at | Rusc1 | 1.47 | 1.30 | 1.47 |
| 1421148_a_at | Tial1 | 1.46 | 1.69 | 1.98 |
| 1452448_at | Agr | 1.46 | 1.58 | 1.91 |
| 1451048_at | Metap2 | 1.43 | 1.62 | 1.61 |
| 1460853_at | 1700025K23Rik | 1.42 | 1.75 | 1.94 |
| 1438894_at | Selenoprotein O | 1.40 | 1.54 | 1.43 |
| 1452108_x_at | Gspt1 | 1.39 | 2.14 | 2.25 |
| 1432029_a_at | Smap1 | 1.38 | 1.60 | 1.50 |
| 1423212_at | Pscl | 1.38 | 1.98 | 1.86 |
| 1451050_at | NT5C3 | 1.38 | 1.56 | 1.63 |
| 1429455_at | Gapvd1 | 1.37 | 1.78 | 1.65 |
| 1423961_at | Wdr26 | 1.36 | 1.98 | 1.97 |
| 1427934_at | Lyrm2 | 1.32 | 1.54 | 1.64 |
| 1417258_at | Cct5 | 1.31 | 1.54 | 1.50 |
| 1448934_at | NDUFA10 | 1.31 | 1.51 | 1.55 |
| 1434894_at | Zc3h13 | 1.22 | 1.34 | 1.26 |
| 1423081_a_at | Tomm20 | 1.17 | 1.45 | 1.68 |
| 1418528_a_at | Dad1 | 1.16 | 1.27 | 1.28 |

FIG. 19E

METHODS FOR INHIBITING STARVATION OF A CELL

RELATED APPLICATIONS

This application claims priority to U.S. Provisional Application No. 61/169,835, filed on Apr. 16, 2009, the entire contents of which are incorporated herein by this reference.

STATEMENT REGARDING FEDERALLY SPONSORED RESEARCH OR DEVELOPMENT

This invention was made with Government support under contract EY014466 awarded by the National Institutes of Health. The government has certain rights in the invention.

FIELD OF THE INVENTION

The present invention is directed to methods for the treatment or prevention of starvation in a cell and disorders associated therewith by the administration of an agent which enhances the intracellular generation and/or uptake of glucose and/or intracellular generation and/or uptake of NADPH and/or intracellular generation and/or uptake of pyruvate and/or intracellular generation and/or uptake of lactate.

BACKGROUND OF THE INVENTION

Cells can be compromised by genetic and environmental factors that lead to their malfunction and death. For example, in the retina, specialized sensory neurons, the photoreceptors (rods and cones), as well as ganglion cells, the output neurons of the retina, are the neuronal cell types that can malfunction and die due to genetic and/or environmental reasons, leading to partial or complete loss of vision.

The retina contains two major types of light-sensitive photoreceptor cells, i.e., rod cells and cone cells. Cone cells are responsible for color vision and require brighter light to function, as compared to rod cells. There are three types of cones, maximally sensitive to long-wavelength, medium-wavelength, and short-wavelength light (often referred to as red, green, and blue, respectively, though the sensitivity peaks are not actually at these colors). Cones are mostly concentrated in and near the fovea. Only a small percentage of photoreceptors are cones in the periphery of the retina. Objects are seen most sharply in focus when their images fall on the cone-enriched spot, as when one looks at an object directly. Cone cells and rods are connected through intermediate cells in the retina to nerve fibers of the optic nerve. When rods and cones are stimulated by light, the nerves send off impulses through these fibers to the brain.

Reduced viability of cone cells is associated with various retinal disorders, in particular, retinitis pigmentosa. Retinitis pigmentosa is a family of inherited retinal degenerations (RD) that is currently incurable and frequently leads to blindness. Affecting roughly 1 in 3,000 individuals, it is the most prevalent form of RD caused by a single disease allele (RetNet, www.sph.uth.tmc.edu/Retnet/). The phenotype is characterized by an initial loss of night vision due to the malfunction and death of rod photoreceptors, followed by a progressive loss of cones (Madreperla, S. A., et al. (1990) *Arch Ophthalmol* 108, 358-61). Additionally, retinitis pigmentosa is further characterized by the following manifestations: night blindness, progressive loss of peripheral vision, eventually leading to total blindness, ophthalmoscopic changes consist in dark mosaic-like retinal pigmentation, attenuation of the retinal vessels, waxy pallor of the optic disc, and in the advanced forms, macular degeneration. Since cones are responsible for color and high acuity vision, it is their loss that leads to a reduction in the quality of life. In many cases, the disease-causing allele is expressed exclusively in rods; nonetheless, cones die too. Indeed, to date there is no known form of RD in humans or mice where rods die, and cones survive. In contrast, mutations in cone-specific genes result only in cone death.

SUMMARY OF THE INVENTION

The present invention is directed to methods for inhibiting starvation of a cell, as well as methods for treating or preventing a disorder associated with starvation of a cell. The present invention is based, at least in part, on the discovery that the upregulation of certain genes in a cell undergoing starvation can serve to enhance intracellular levels of glucose, lactate, pyruvate, and/or NADPH. In particular, the upregulation of genes encoding enzymes involved in glucose transport, glucose production (gluconeogenesis), lactate transport and NADPH production can serve to inhibit cellular starvation, thus increasing cellular viability.

Accordingly, the present invention provides methods for inhibiting starvation of a cell as well as methods for the treatment and/or prevention of disorders associated with cellular starvation, for example, retinitis pigmentosa, by enhancing the intracellular levels of glucose, pyruvate, lactate and/or NADPH.

In one aspect, the present invention is directed to a method for inhibiting starvation of a cell by contacting the cell with an agent that enhances the intracellular generation and/or uptake of glucose and/or lactate and/or pyruvate and/or NADPH in the cell. In another aspect, the present invention is directed to a method for treating or preventing a disorder associated with starvation of a cell in a subject by administering to the subject an agent that enhances the intracellular generation and/or uptake of glucose and/or lactate and/or pyruvate and/or NADPH. In another aspect, the present invention provides a method for treating or preventing retinitis pigmentosa in a subject by administering to the subject an agent that enhances the intracellular generation and/or uptake of glucose and/or lactate and/or pyruvate and/or NADPH. In yet another aspect, the present invention is directed to a method for prolonging the viability of a cone cell by contacting the cell with an agent that enhances the intracellular generation and/or uptake of glucose and/or lactate and/or pyruvate, and/or NADPH, e.g., for about 1 week, about 2 weeks, about 3 weeks, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 2 years, about 3 years, about 4 years, about 5 years, about 10 years, about 15, years, about 20 years, about 25 years, about 30 years, about 40 years, about 50 years, about 60 years, about 70 years, and about 80 years. In another aspect, the present invention is directed to a method for prolonging the viability of a rod cell by contacting the cell with an agent that enhances the intracellular generation and/or uptake of glucose and/or lactate and/or pyruvate, and/or NADPH, e.g., for about 1 week, about 2 weeks, about 3 weeks, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 2 years, about 3 years, about 4 years, about 5 years, about 10 years, about 15, years, about 20 years, about 25 years, about 30 years, about 40 years, about 50 years, about 60 years, about 70 years, and about 80 years Cell types suitable for use in the methods of the invention include, for example, any cell type that is undergoing starvation and/or ischemia, e.g., neuronal cells, skeletal muscle cells, pancreatic islet cells, vascular endothelial cells.

In various embodiments of the foregoing aspects of the invention, the agent enhances the intracellular generation of glucose, enhances the uptake of glucose into a cell, enhances the intracellular generation of NADPH, enhances the intracellular uptake of lactate, and/or enhances the intracellular uptake of pyruvate into a cell, in order to increase the level of intermediates for energy production or anabolic reaction such that the metabolic flux in a cell is enhanced through the pentose phosphate pathway, and/or the ability of a cell to generate phospholipids or other anabolic products is enhanced, and/or the ability of a cell to detoxify free oxygen radicals is enhanced.

In one embodiment, the agent for use in the methods of the invention is a nucleic acid molecule, e.g., a nucleic acid molecule which encodes an enzyme selected from the group consisting of a glucose transporter, a gluconeogenic gene, glucose-6-phosphatase, pyruvate carboxylase, phosphoenolpyruvate carboxykinase, fructose 1,6-bisphosphatase, lactate transporter and malic enzyme. The nucleic acid molecule may encode an enzyme involved in the pentose phosphate pathway, for example, glucose-6-phosphate dehydrogenase, 6-phosphogluconolactonase, phosphogluconate dehydrogenase, ribulose-5-phosphate isomerase, ribulose-5-phosphate epimerase, transketolase or transaldolase.

In another embodiment, the cell is contacted with or the subject is administered at least two nucleic acid molecules which enhance the intracellular generation and/or uptake of glucose and/or pyruvate and/or lactate and/or NADPH, for example, at least two nucleic acid molecules selected from the group consisting of the pyruvate carboxylase gene, the phosphoenolpyruvate carboxykinase gene, and the fructose 1,6-bisphosphatase gene.

In yet another embodiment, the nucleic acid molecule is contained within a vector, for example, a retrovirus, an adenovirus, an adenoviral/retroviral chimera, an adeno-associated virus (AAV), a herpes simplex virus I or II, a parvovirus, a reticuloendotheliosis virus, a poliovirus, a papillomavirus, a vaccinia virus and a lentivirus. In a particular embodiment, the vector is an AAV vector, for example, an AAV 2/5 or an AAV 2/8 vector.

In various embodiments, the disorder is a neurodegenerative disorder, for example, a stroke or Alzheimer's Disease. The disorder may also be an ocular disorder, for example, retinitis pigmentosa, age related macular degeneration, cone rod dystrophy, rod cone dystrophy or glaucoma. In yet another embodiment, the disorder is an ocular disorder associated with the decreased viability of cone cells and/or rod cells. In other embodiments, the ocular disorder is a genetic disorder. In still other embodiments, the disorder is a disorder which deprives cells of glucose, e.g., an ischemic disorder, e.g., heart attack, wound, diabetes, Parkinson's disease.

In certain embodiments, the nucleic acid molecule is administered by injection, e.g., an intraocular injection.

Other features and advantages of the invention will be apparent from the following detailed description and claims

BRIEF DESCRIPTION OF THE DRAWINGS

FIG. 14 further depicts the levels of phosphorylated S6 (p*-S6) (medium gray, light gray marks cones with PNA, dark gray nuclear DAPI stain) in wild type (g, h) and mutant (i-m) cones. (g) Low levels of p*-S6 were seen in wild type cones but not in cone OSs. (h) DAPI overlap of (g). (i, j) Strong uniform expression in cones was seen the PDE-β mutant shortly after the end of the major rod death phase (PW3). Area in lower right corner shows a region where cones had started to die. (j) DAPI overlap of (i). (k-l) Higher magnification at PW5 showing same field at three different confocal depths. (k) Within the plane of the cone outer segments, high levels of p*-S6 were seen in cones when compared to segments of wild type cones. (l) Strong staining was also seen in the plane of the cone nuclei, indicating a uniform cytoplasmic distribution. (m) Within the plane of the INL, levels of p*-S6 were much lower than in cones.

Values for both types of calculations are shown, for the fixed threshold and adjusted threshold.

Figures 17A, 17B, 17C, 17D, 17E:
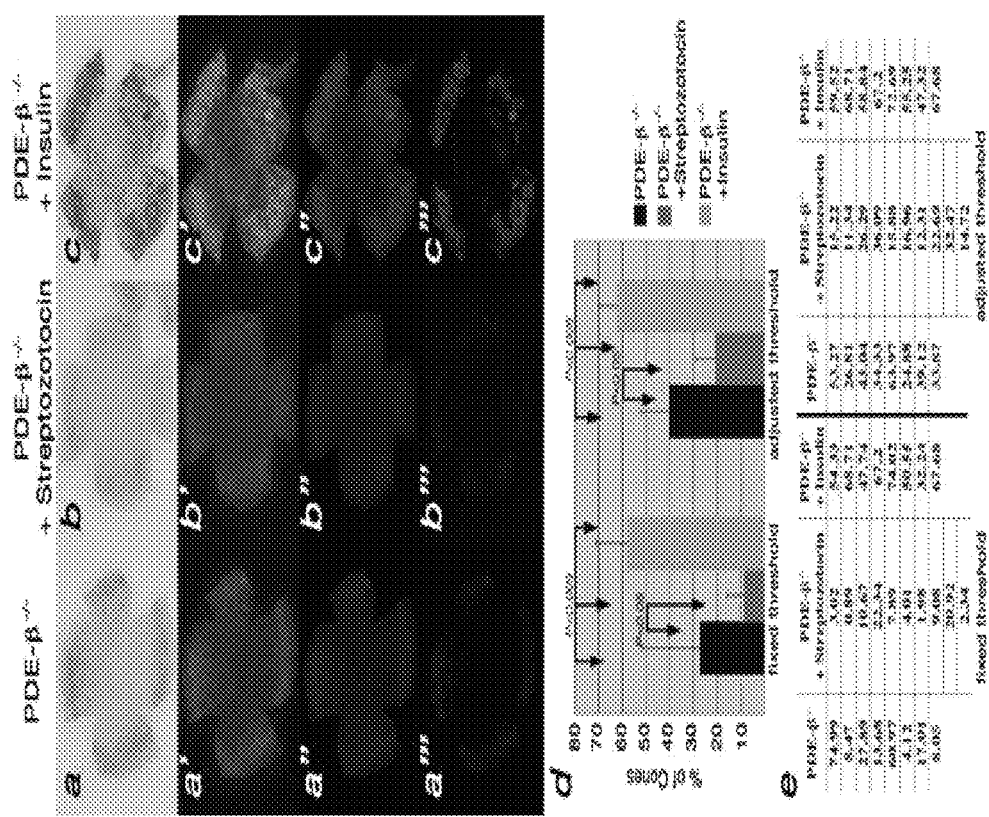
FIG. 17 depicts a method to calculate cone survival as described in Example 1 as follows: (a-c) Show retinal flat mounts stained for lacZ (see FIG. 15). (a) Untreated control PDE-β-/- mouse at PW7. (b) PDE-β-/- mouse at PW7 treated with one injection of Streptozotocin at PW3. (c) PDE-β-/- mouse at PW7 treated for 4 weeks with daily injections of insulin starting at PW3. (a'-c') Show inverted color images of corresponding panels (a-c). (a"-c") Show only the green channels whereas (a'''-c''') show only the red channels of the inverted color images (a'-c'). The red channel served as a proxy for the lacZ stain whereas the green channel served as a proxy for the retina. (d) Quantification of cone survival by calculating the surface area of red that co-localizes with green. Two different methods were employed, a fixed threshold and an adjusted threshold. The fixed threshold was determined by adjusting the lower intensity of the red channel in the image with the most intense lacZ staining (most intense red channel) to reflect the pattern of the lacZ staining. The same threshold for the red channel was then applied to all other images. As this method would under represent cone survival in mice that were not treated with insulin due to the less intense lacZ staining a second method was employed. For each image the lower intensity of the red channel was adjusted individually to match the blue pattern of the lacZ staining avoiding the problem of the difference in lacZ intensity. The increased intensity of lacZ in the insulin treated mice could be due to healthier cones that either have an increased transcription/translation or decreased protein degradation. (e) Shows the actual calculated values in percentage of cone survival for all retinae. Values are shown for the untreated mice, the Streptozotocin treated mice and the insulin treated mice.
Figures 18A, 18B, 18C:
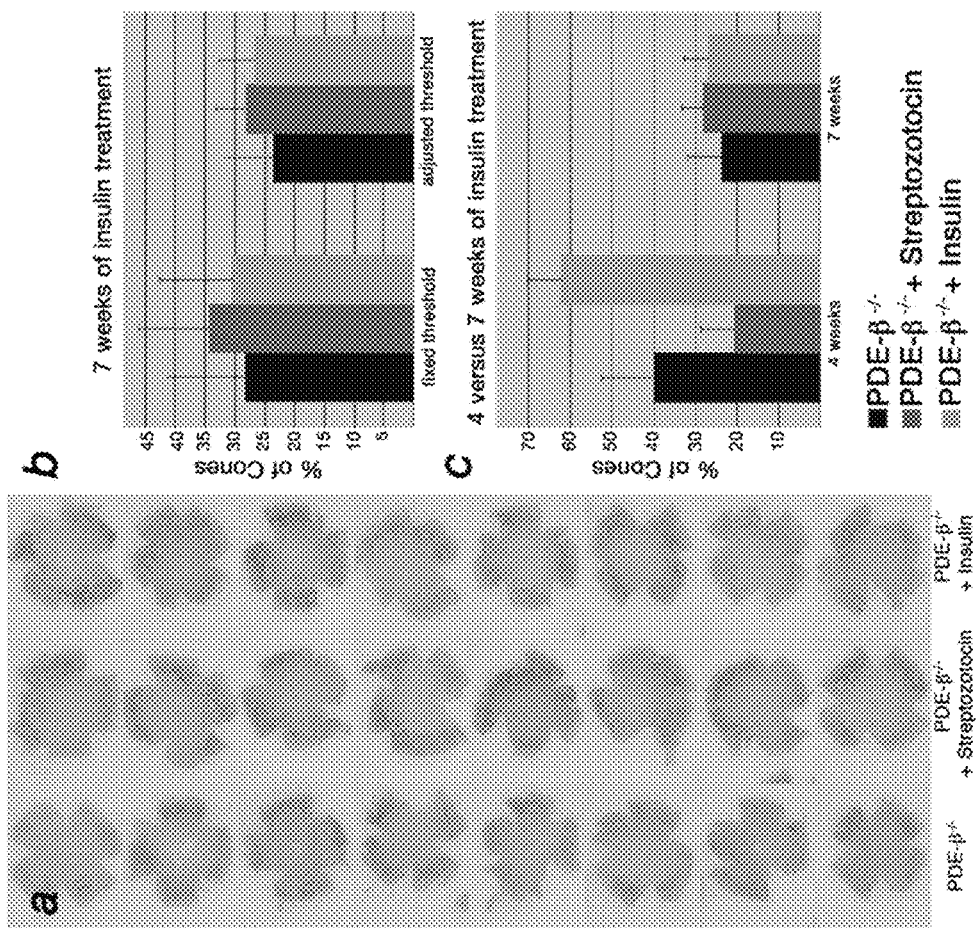

FIG. 18 depicts the assessment of cone survival after prolonged Insulin treatment as described in Example 1 as follows: (a) Composite of retinae after lacZ staining. First column shows untreated PDE-$\beta^{-/-}$ mice at PW10. Second column shows retinae of PDE-$\beta^{-/-}$ mice at PW10 that received a single injection of streptozotocin at PW3. Third column shows retinae of PDE-$\beta^{-/-}$ mice at PW10 that received daily injections of insulin starting at PW3. (b) Shows quantification of cone survival by the two methods described in FIG. 17. There was no significant difference in cone survival between treated and untreated mice at PW10. (c) Shows comparison between the 4 and 7 weeks treatment.

FIGS. 19A-E depict a table of 230 genes that had statistically significant changes in all 4 mouse models and had fold changes >2 at the onset of cone death, when compared to the other three time points. The fold change is indicated as $log_2$. (AVG: Average of fold change from the 4 mutants; C0: Onset of cone death; R: peak of rod death; C1& C2: first and second time point during cone death respectively, see also FIG. 7a).

Figure 20:
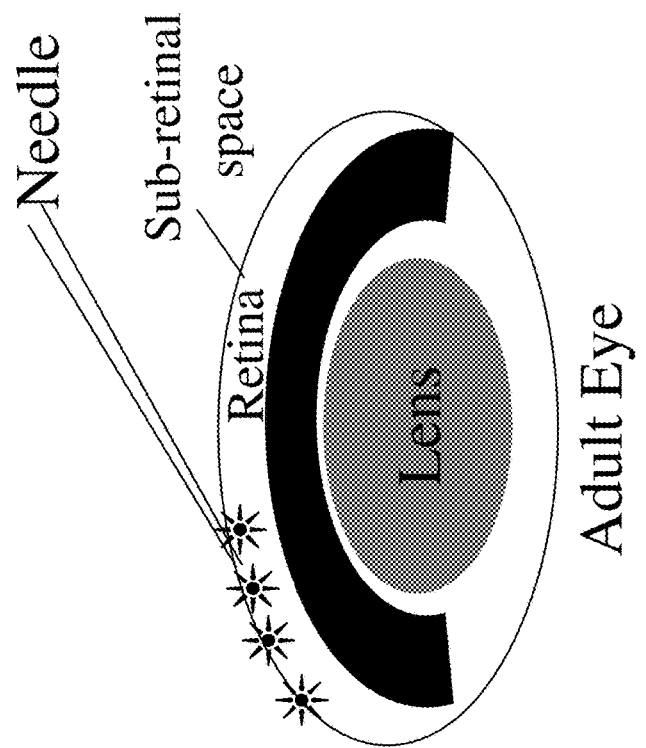

FIG. 20 depicts the injection into the sub-retinal space of the adult eye of an AAV vector containing genes encoding pyruvate carboxylase, fructose 1,6-bisphosphatase and phosphoenolpyruvate carboxykinase in order to induce gluconeogenesis.

Figure 21:
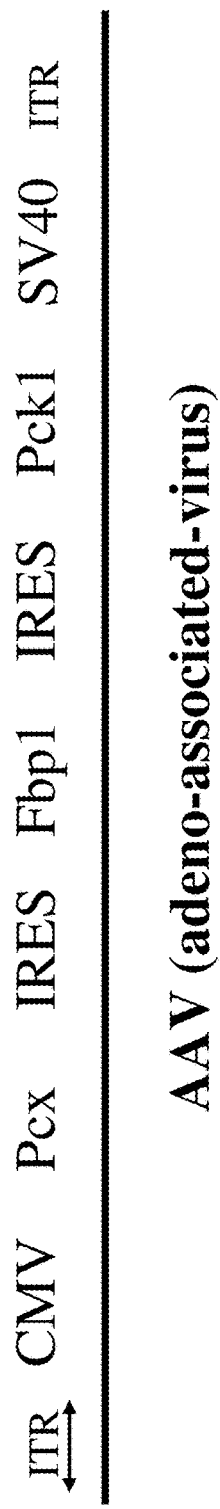

FIG. 21 schematically depicts the AAV vector that was used to infect cone cells in the eye of an rd1 mutant mouse.

Figure 22:
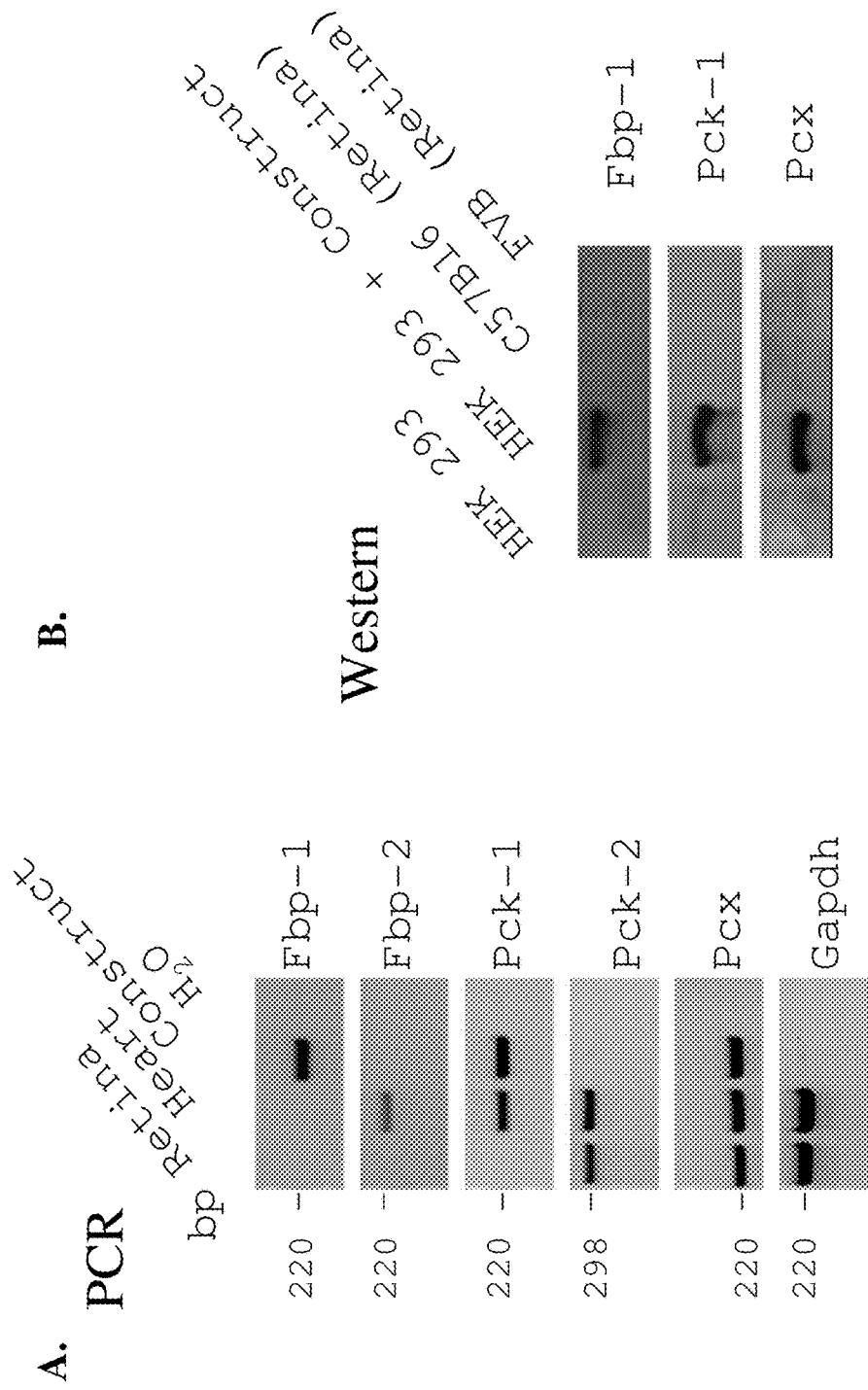

FIGS. 22A and B depict the mRNA expression and protein expression of gluconeogenesis genes. FIG. 22A shows that Fbp-1, Fbp-2, Pck-1, Pck-2, and Pcx mRNA are expressed in the retina and heart, and that the AAV vector comprising Fbp-1, Pck-1, and Pcx ("construct"; described in Example 2) expresses these genes. Gapdh is used as a loading control and water is used as a negative control. FIG. 22B is a Western blot demonstrating that the protein expression of Fbp-1, Pck-1, and Pcx in HEK 293 cells transfected with the AAV vector comprising these genes is upregulated as compared to the protein expression of these same genes in the retina and HEK 293 control samples.

Figure 23:
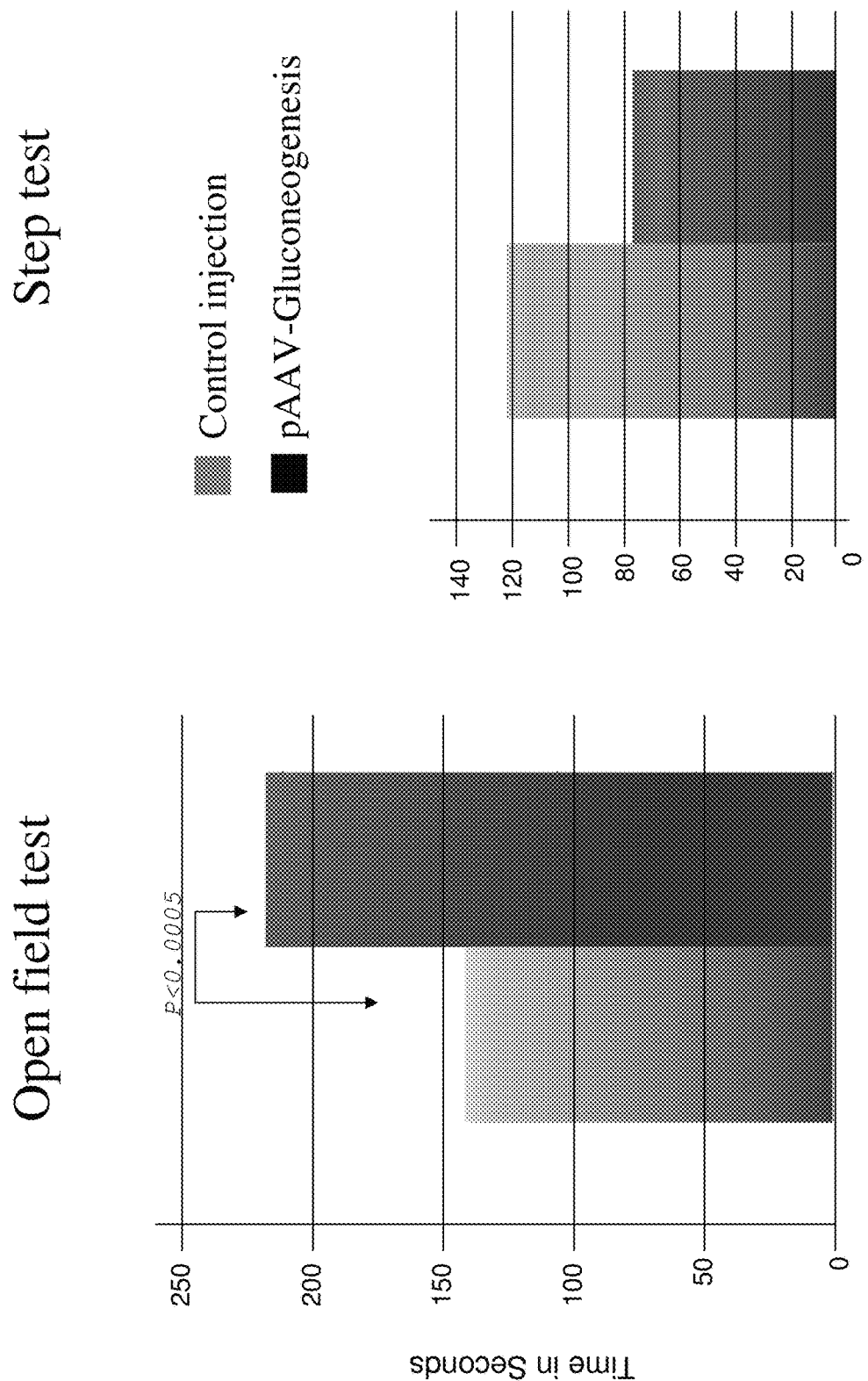

FIG. 23 is a graph depicting the open field and step tests performed on the rd1 mutant mice in which the AAV vector was introduced.

Figure 24:
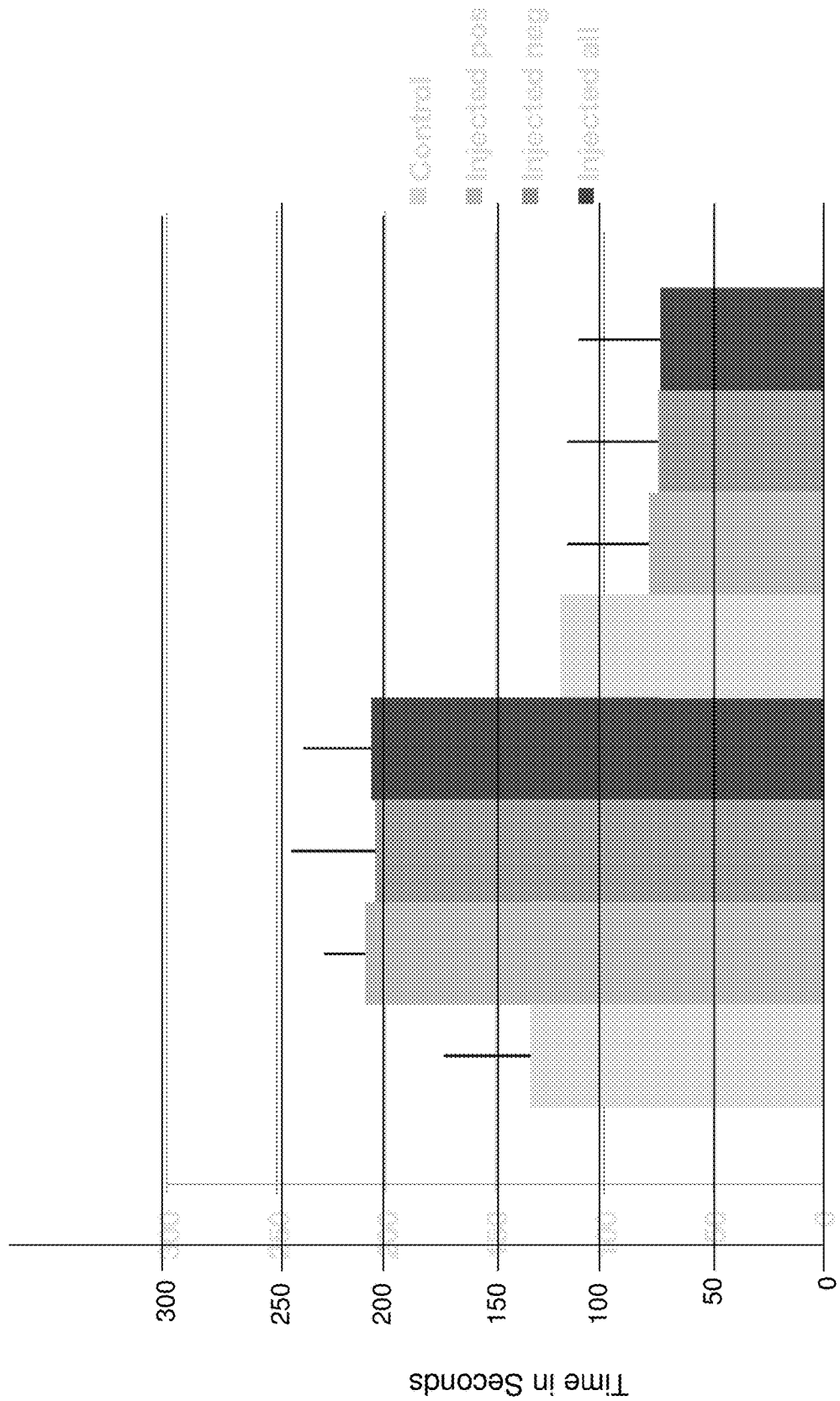

FIG. 24 is a graph depicting the open field and step tests performed on the rda1 mutant mice in which the AAV vector was introduced.

Figure 25:
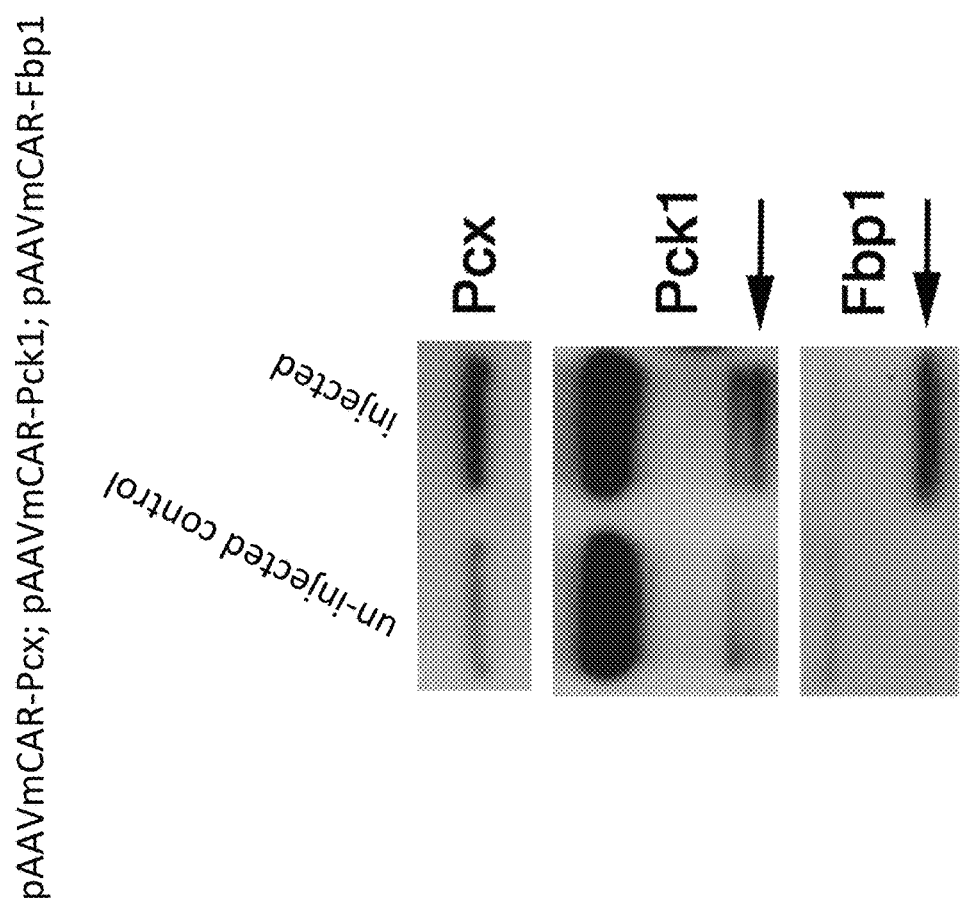

FIG. 25 depicts Western blot analysis of cellular extracts prepared from retinas transfected with three AAV vectors; one vector comprising Pcx, a second vector comprising Pck-1, and a third vector comprising Fbp-1.

Figure 26:
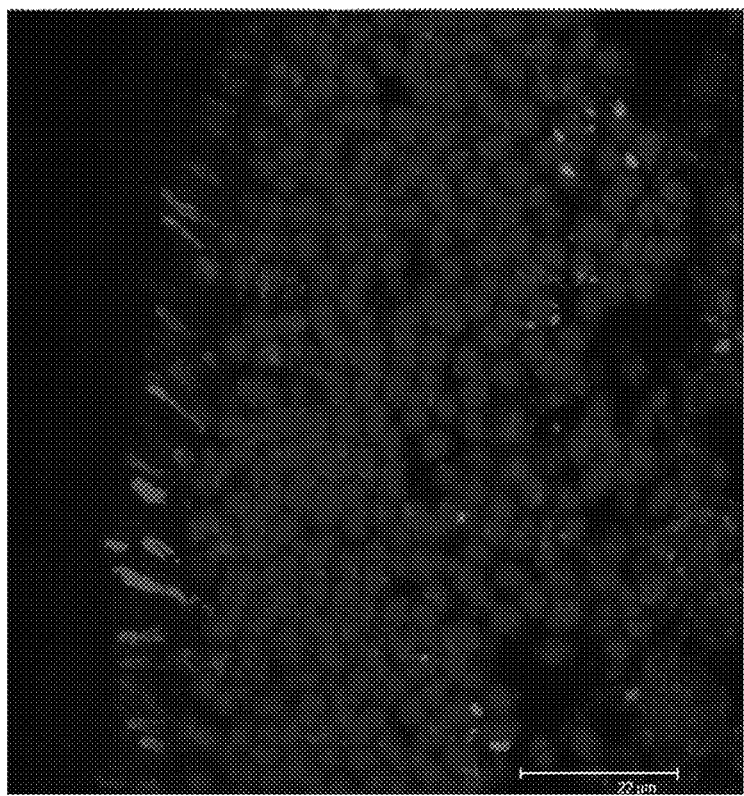
Figure 26:
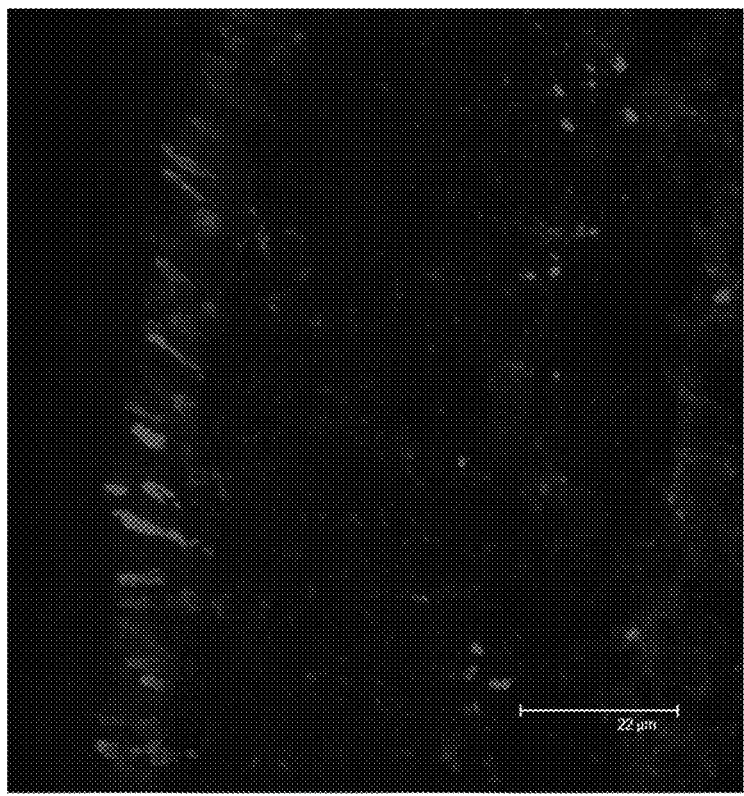

FIG. 26 depicts immunohistochemisty analysis showing overexpression of Pcx in photoreceptors of retinas transfected with three AAV vectors; one vector comprising Pcx, a second vector comprising Pck-1, and a third vector comprising Fbp-1.

Figure 27:
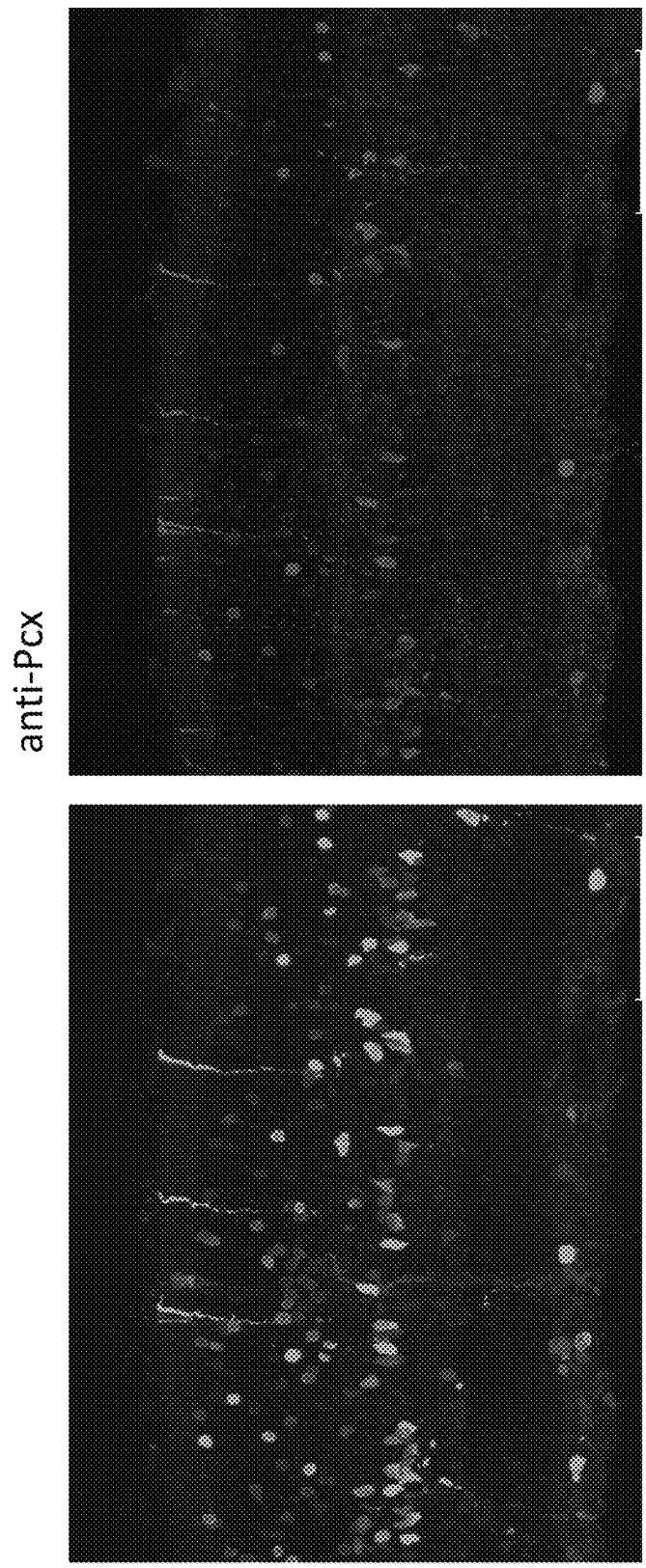

FIG. 27 depicts immunohistochemisty analysis showing overexpression of Pcx in photoreceptors of retinas transfected with an AAV vector comprising Pcx and mGFP and a second AAV vector comprising H2BGFP, Fbp-1, and Pck-1.

Figure 28:
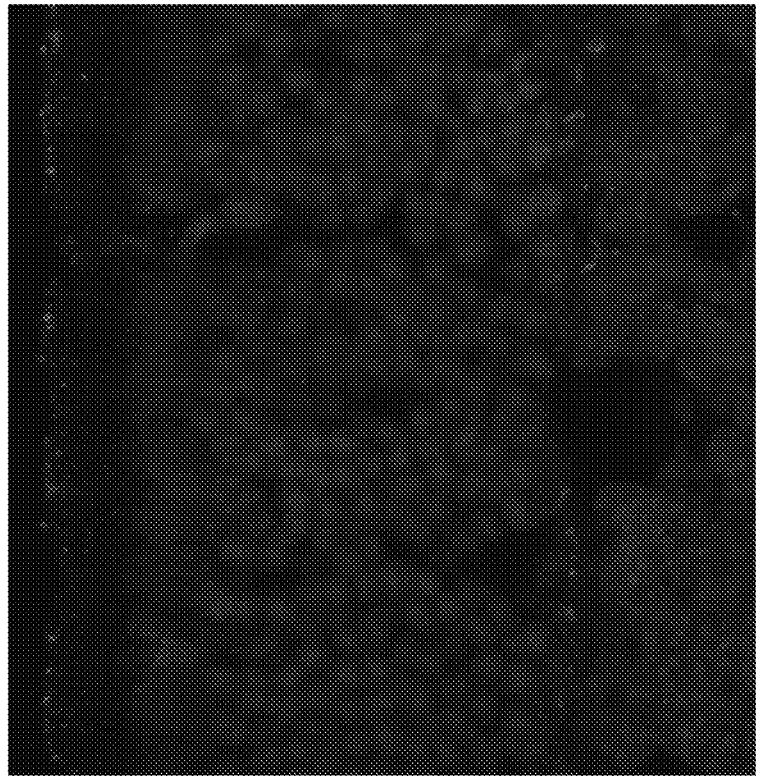
Figure 28:
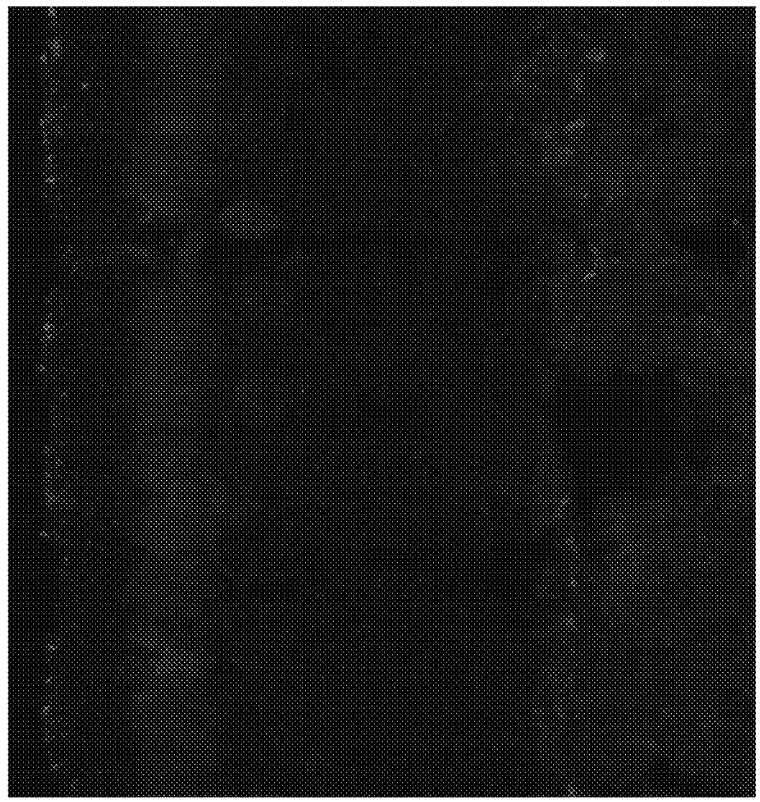

FIG. 28 depicts immunohistochemisty analysis showing overexpression of Fbp-1 in photoreceptors of retinas transfected with three AAV vectors; one vector comprising Pcx, a second vector comprising Pck-1, and a third vector comprising Fbp-1.

Figure 29:
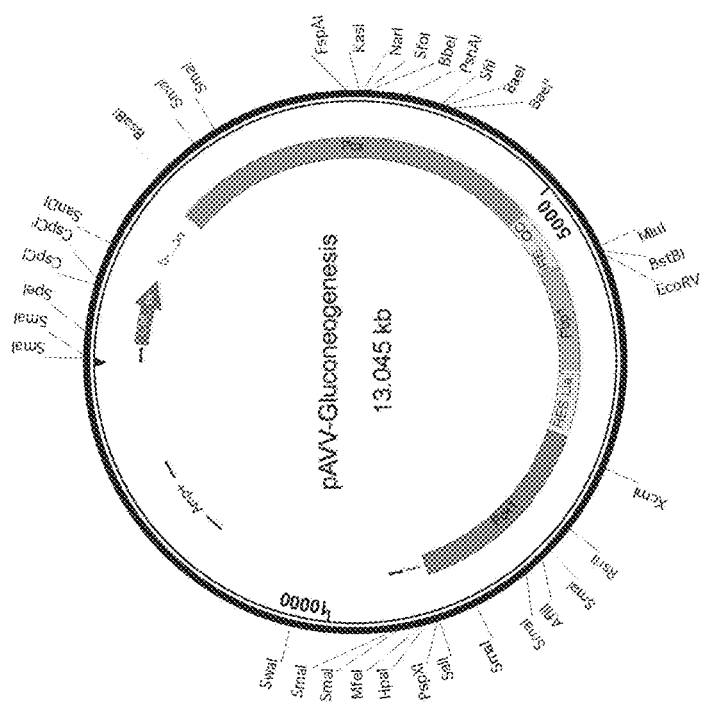

FIG. 29 depicts a map of the AAV2/5 vector comprising the CMV promoter and the gluconeogenesis genes, Pck-1, Fbp-1, and Pcx-1, used to infect cone cells in the eye of an rd1 mutant mouse. See also SEQ ID NO:11.

Figure 30:
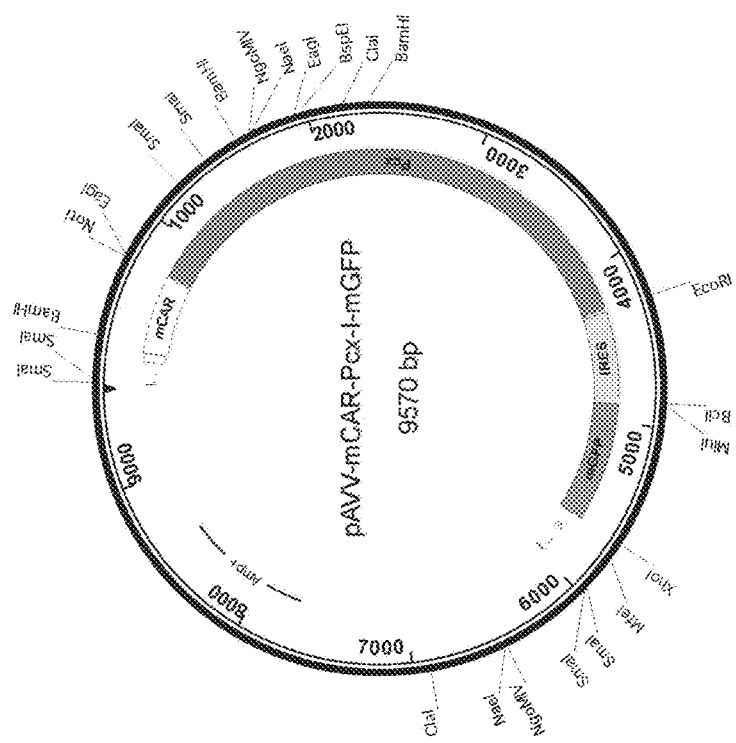

FIG. 30 depicts a map of the AAV2/5 vector comprising the CAR promoter, the gluconeogenesis gene, Pcx-1, and mGFP. See also SEQ ID NO:12.

Figure 31:
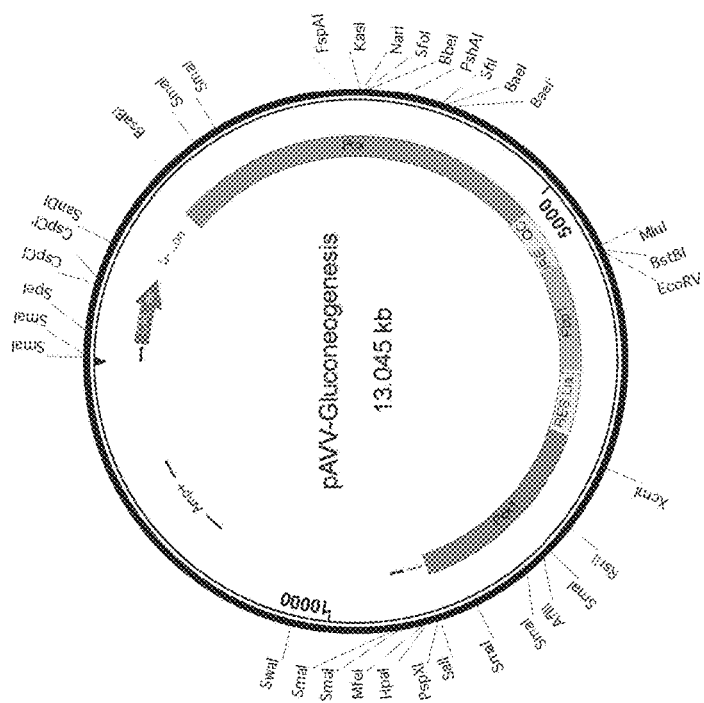

FIG. 31 depicts a map of the AAV2/5 vector comprising the CAR promoter and the gluconeogenesis gene, Pck-1. See also SEQ ID NO:13.

Figure 32:
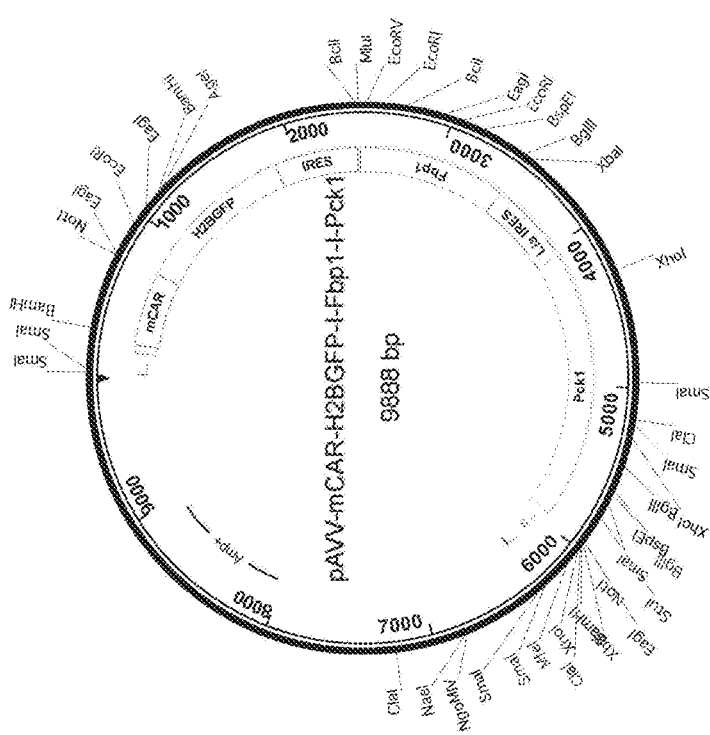

FIG. 32 depicts a map of the AAV2/5 vector comprising the CAR promoter, H2BGFP, and the gluconeogenesis genes, Fbp-1 and Pck-1. See also SEQ ID NO:14.

Figure 33:
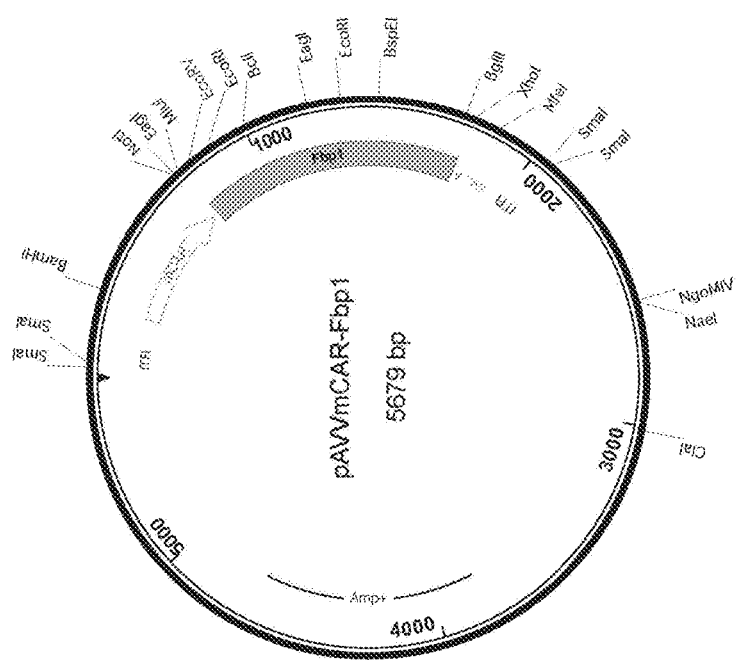

FIG. 33 depicts a map of the AAV2/5 vector comprising the CAR promoter and the gluconeogenesis gene, Fbp-1. See also SEQ ID NO:15.

Figure 34:
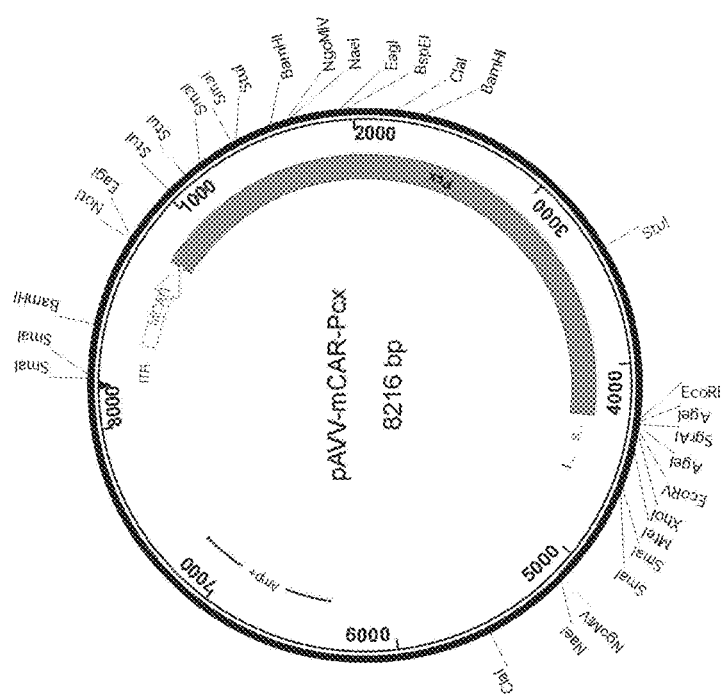

FIG. 34 depicts a map of the AAV2/5 vector comprising the CAR promoter and the gluconeogenesis gene, Pcx-1. See also SEQ ID NO:16.

DETAILED DESCRIPTION OF THE INVENTION

The present invention is based, at least in part, on the discovery that the upregulation of certain genes in a cell, e.g., a neuronal cell, undergoing cellular starvation, can serve to enhance intracellular levels of glucose, pyruvate, lactate, and/or NADPH. In addition, it has been discovered that cone cells in a mouse model of RP undergo self-digestion, or autophagy, a sign of insufficient nutrition. Accordingly, the upregulation of genes encoding enzymes involved in glucose transport, glucose production, gluconeogenesis, lactate transport and NADPH production can serve to inhibit cellular starvation, thus, increasing cellular viability. Additionally, increased levels of glucose, pyruvate, lactate, and/or NADPH can enhance production of phospholipids, the components of cell membranes, thereby increasing cellular viability under conditions when nutrition is limited.

Without wishing to be bound by any particular theory, it is believed that by upregulating the level of intracellular glucose, pyruvate, lactate, and/or NADPH, the cells are provided with additional nutrition to sustain themselves and, are further provided the building blocks for cellular structure, for example, the building blocks for the production of phospholipids, the primary component of cellular membranes. Accordingly, the enhancement of intracellular glucose, pyruvate, lactate, and/or NADPH serves to promote or enhance cellular viability, e.g., when cells are compromised by genetic and environmental factors and to treat or prevent a disorder associated with starvation of cells, e.g., a disorder that would otherwise lead to malfunction and death of the cells.

Accordingly, the present invention provides methods for inhibiting starvation of a cell, as well as methods for the treatment and/or prevention of disorders associated with cellular starvation, for example, retinitis pigmentosa, by enhancing the intracellular levels of glucose, pyruvate, lactate and/or NADPH.

In one embodiment of the invention, cells suitable for use in the instant methods are neuronal cells. As used herein, the terms "neuron" or "neuronal cell" refer to a nerve cell capable of receiving and conducting electrical impulses from the nervous system. A nerve cell or "neuron" typically comprises a cell body, an axon, axon terminals, and dendrites and is readily identifiable by one of ordinary skill in the art.

As used herein, the terms "neural" or "neural cell" also include "glial cells", also referred to as "neuroglia" or "glia", which are cells that provide support and nutrition (e.g., glucose or lactate), maintain homeostasis, form myelin, and participate in signal transmission in the nervous system.

The types of glial cells are: "astrocytes", "oligodendrocytes", "Schwann cells"), and "microglia". "Astrocytes" have numerous projections that anchor neurons to their blood supply and regulate nutrition of neuronal cells. They also regulate the external chemical environment of neurons by removing excess ions, notably potassium, and recycling neurotransmitters released during synaptic transmission. "Oligodendrocytes" and "Schwann cells" coat axons in the central or peripheral nervous system, respectively, to form a myelin sheath which provides insulation to the axon that allows electrical signals to propagate more efficiently. "Microglia" are specialized macrophages capable of phagocytosis.

In one embodiment, a neuron is a "photoreceptor cell", i.e., a specialized neuron found in the retina. The retina is a thin, transparent tissue containing about 120 million separate rod cells (night vision) and 7 million cone cells (day and color vision) as well as millions of other structural supporting and interconnecting cells. Photoreceptor cells consist of "rods" and "cones", which are the photosensitive cells of the retina. The rods contain rhodopsin, the rod photopigment, and the cones contain other distinct photopigments, which respond to light and ultimately trigger a neural discharge in the output cells of the retina, the ganglion cells. Ultimately, this signal is registered as a visual stimulus in the visual cortex and other target locations in the brain. The retinal pigment epithelial (RPE) cells produce, store and transport a variety of factors that are responsible for the normal function and survival of photoreceptors. Retinal neurons that can also sense light consist of photosensitive ganglion cells. These cells, known as the melanopsin ganglion cells are found in the inner retina, have dendrites and long axons projecting to the protectum (midbrain), the suprachiasmatic nucleas in the hypothalamus, and the lateral geniculate (thalamus). In one embodiment, a photoreceptor cell is a rod. In one embodiment, a photoreceptor cell is a cone. In one embodiment, a photosensitive cell is a cell is a melanopsin ganglion cell.

As used herein, the term "starvation of a cell", "cellular starvation", "cellular ischemia" refers to the insufficient supply of nutrients to a cell to allow for proper functioning and maintenance. In particular embodiments, cellular starvation includes insufficient supply of glucose, pyruvate, lactate, NADPH, and/or oxygen and/or insufficient ability to generate phospholipids, cellular membranes, cellular proteins, nucleic acid, carbohydrates, vitamins, or intermediates thereof, and slower than normal cellular processes, e.g., DNA replication, translation, generation of glucose, pyruvate, lactate, NADPH, oxygen, phospholipids, cellular membranes, cellular proteins, nucleic acid, carbohydrates, vitamins, or intermediates thereof. Methods for identifying a cell undergoing starvation are routine to one of ordinary skill in the art and include, for example, determination of the rate of cell division, protein synthesis, glucose uptake, intracellular oxygen levels, organelle digestion (macroautophagy), and protein degradation through, e.g., chaperone-mediated autophagy or the ubiquitin-proteasome system.

As used herein, the term "disorders associated with starvation of a cell" includes disorders in which there is insufficient supply of nutrients to the cell to allow for proper functioning and maintenance. Exemplary disorders include disorders, diseases, conditions or injuries in which upregulation of intracellular glucose, pyruvate, lactate, NADPH would be beneficial, e.g., to increase cell viability, such as ischemic disorders, neurodegenerative disorders, ocular disorders, retinal disorders, stroke, heart attack, or wound healing.

As used herein, the term "neurodegenerative disorder" refers to disorders in which neuronal integrity is threatened, for example, where neuronal cells display decreased survival or exhibit an inability or reduced ability to propagate a signal. Neurodegenerative disorders are well known in the art and include, for example, stroke or Alzheimer's Disease.

As used herein, the term "ocular disorder" refers to a disorder of the eye. In a particular embodiment of the invention, the ocular disorder is characterized and/or associated with cellular starvation. For example, ocular disorders include, but are not limited to, retinal disorders, retinitis pigmentosa, age related macular degeneration, cone rod dystrophy, rod cone dystrophy and glaucoma.

As used herein, the term "retinal disorder" refers generally to a disorder of the retina. In one embodiment, the retinal disorder is associated with decreased viability, for example, death, of cone cells, and/or rod cells. Moreover, in a particular embodiment, a retinal disorder is not associated with blood vessel leakage and/or growth, for example, as is the case with diabetic retinopathy, but, instead is characterized primarily by reduced viability of cone cells and/or rod cells. In certain embodiments, the retinal disorder is a genetic disorder. In a particular embodiment, the retinal disorder is retinitis pigmentosa.

As used herein, the term "retinitis pigmentosa" or "RP" is known in the art and encompasses a disparate group of genetic disorders of rods and cones. Retinitis pigmentosa generally refers to retinal degeneration often characterized by the following manifestations: night blindness, progressive loss of peripheral vision, eventually leading to total blindness; ophthalmoscopic changes consist in dark mosaic-like retinal pigmentation, attenuation of the retinal vessels, waxy pallor of the optic disc, and in the advanced forms, macular degeneration. In some cases there can be a lack of pigmentation. Retinitis pigmentosa can be associated to degenerative opacity of the vitreous body, and cataract. Family history is prominent in retinitis pigmentosa; the pattern of inheritance may be autosomal recessive, autosomal dominant, or X-linked; the autosomal recessive form is the most common and can occur sporadically.

As used herein, the terms "Cone-Rod Dystrophy" or "CRD" and "Rod-Cone Dystrophy" or "RCD" refer to art recognized inherited progressive diseases that cause deterioration of the cone and rod photoreceptor cells and often result in blindness. CRD is characterized by reduced viability or death of cone cells followed by reduced viability or death of rod cells. By contrast, RCD is characterized by reduced viability or death of rod cells followed by reduced viability or death of cone cells.

As used herein, the term "age-related macular degeneration" also referred to as "macular degeneration" or "AMD", refers to the art recognized pathological condition which causes blindness amongst elderly individuals. Age related macular degeneration includes both wet and dry forms of ARMD. The dry form of ARMD, which accounts for about 90 percent of all cases, is also known as atrophic, nonexudative, or drusenoid (age-related) macular degeneration. With the dry form of ARMD, drusen typically accumulate in the retinal pigment epithelium (RPE) tissue beneath/within the Bruch's membrane. Vision loss can then occur when drusen interfere with the function of photoreceptors in the macula, which may include reduction of the flow of nutrients from the choroidal vasculature through the RPE to the photoreceptors. The dry form of ARMD results in the gradual loss of vision over many years. The dry form of ARMD can lead to the wet form of ARMD. The wet form of ARMD, also known as exudative or neovascular (age-related) macular degeneration, can progress rapidly and cause severe damage to central vision. The macular dystrophies include Stargardt Disease, also known as Stargardt Macular Dystrophy or Fundus Flavimaculatus, which is the most frequently encountered juvenile onset form of macular dystrophy.

As used herein, the term "glaucoma" has its art recognized meaning, and refers to a group of eye diseases characterized by degeneration of the optic nerve head and visual field loss, often caused by increased intraocular pressure due to blockage of the channel through which aqueous humor drains (chronic or open-angle glaucoma) or by pressure of the iris against the lens (acute or angle-closure glaucoma). The term "glaucoma," as used herein, includes primary glaucomas, secondary glaucomas, and familial (i.e., inherited glaucomas). The increase in intraocular pressure may result in a reduction of blood flow through the retinal vasculature, thus leading to a reduction in nutrients delivered to retinal neurons.

As used herein, the term "stroke" refers to the art recognized pathological condition in which impairment of consciousness and neurological symptom(s) are acutely induced by a cerebrovascular disorder, which includes intracerebral hemorrhages (hypertensive intracerebral hemorrhage and the like), cerebral infarction, transient ischemic attack, subarachnoid hemorrhage, cerebral thrombosis (atherothrombotic cerebral infarction and the like), cerebral embolism (cardiogenic cerebral embolism and the like) and lacunar infarction.

As used herein, the terms "Alzheimer's Disease" or "AD" encompass both non-hereditary and hereditary forms of the disease. Specifically, the terms, as used herein, include the non-hereditary form which is a progressive degenerative disease of the brain primarily associated with aging. The terms further include the hereditary form called familial Alzheimer's disease (FAD). Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and death in the range of four to twelve years.

The term "glucose transporter" as used herein refers to a protein that catalyzes the transport of glucose across a cell membrane. More specifically the glucose transporter facilitates the uptake of glucose into the cytoplasm across the plasma membrane.

The term "lactate transporter" as used herein refers to a protein that catalyzes the transport of lactate across a cell membrane. More specifically the lactate transporter facilitates the uptake of lactate into the cytoplasm across the plasma membrane.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. A nucleic acid molecule used in the methods of the present invention can be isolated using standard molecular biology techniques. Using all or portion of a nucleic acid sequence of interest as a hybridization probe, nucleic acid molecules can be isolated using standard hybridization and cloning techniques (e.g., as described in Sambrook, J., Fritsh, E. F., and Maniatis, T. Molecular Cloning. A Laboratory Manual. 2nd, ed., Cold Spring Harbor Laboratory, Cold Spring Harbor Laboratory Press, Cold Spring Harbor, N.Y., 1989).

An "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived.

A nucleic acid molecule for use in the methods of the invention can also be isolated by the polymerase chain reaction (PCR) using synthetic oligonucleotide primers designed based upon the sequence of a nucleic acid molecule of interest. A nucleic acid molecule used in the methods of the invention can be amplified using cDNA, mRNA or, alternatively, genomic DNA as a template and appropriate oligonucleotide primers according to standard PCR amplification techniques. Furthermore, oligonucleotides corresponding to nucleotide sequences of interest can be prepared by standard synthetic techniques, e.g., using an automated DNA synthesizer.

The nucleic acids for use in the methods of the invention can also be prepared, e.g., by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, a nucleic acid molecule of the invention is an siRNA molecule. In another embodiment, a nucleic acid molecule of the invention is an shRNA molecule. In one embodiment, a nucleic acid molecule of the invention mediates RNAi.

In another embodiment, a nucleic acid molecule of the invention mediates translational inhibition. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287. 2431-2432 (2000); Zamore, P. D., et al. Cell 101, 25-33 (2000). Tuschl, T. et al. Genes Dev. 13, 3191-3197 (1999); Cottrell T R, and Doering T L. 2003. Trends Microbiol. 11:37-43; Bushman F. 2003. Mol. Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more of the chemistries described herein for use in antisense RNA can be employed in molecules that mediate RNAi.

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes or nucleic acid molecules to which they are operatively linked and are referred to as "expression vectors" or "recombinant expression vectors" or simply "expression vectors". Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. In some embodiments, "expression vectors" are used in order to permit pseudotyping of the viral envelope proteins.

Expression vectors are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses, adeno-associated viruses, lentiviruses), which serve equivalent functions.

As used herein, the term "retrovirus" is used in reference to RNA viruses that utilize reverse transcriptase during their replication cycle. The retroviral genomic RNA is converted into double-stranded DNA by reverse transcriptase. This double-stranded DNA form of the virus is capable of being integrated into the chromosome of the infected cell; once integrated, it is referred to as a "provirus." The provirus serves as a template for RNA polymerase II and directs the expression of RNA molecules which encode the structural proteins and enzymes needed to produce new viral particles. At each end of the provirus are structures called "long terminal repeats" or "LTRs." LTRs contain numerous regulatory signals, including transcriptional control elements, polyadenylation signals, and sequences needed for replication and integration of the viral genome. LTRs may be several hundred base pairs in length.

The term "AAV vector" refers to a vector derived from an adeno-associated virus serotype, including without limitation, AAV-1, AAV-2, AAV-3, AAV-4, AAV-5, or AAVX7. "rAAV vector" refers to a vector that includes AAV nucleotide sequences as well as heterologous nucleotide sequences. rAAV vectors require only the 145 base terminal repeats in cis to generate virus. All other viral sequences are dispensable and may be supplied in trans (Muzyczka (1992) *Curr. Topics Microbiol. Immunol.* 158:97). Typically, the rAAV vector genome will only retain the inverted terminal repeat (ITR) sequences so as to maximize the size of the transgene that can be efficiently packaged by the vector. The ITRs need not be the wild-type nucleotide sequences, and may be altered, e.g., by the insertion, deletion or substitution of nucleotides, as long as the sequences provide for functional rescue, replication and packaging. In particular embodiments, the AAV vector is an AAV2/5 or AAV2/8 vector. Suitable AAV vectors are described in, for example, U.S. Pat. No. 7,056,502 and Yan et al. (2002) *J. Virology* 76(5): 2043-2053, the entire contents of which are incorporated herein by reference.

As used herein, the term "lentivirus" refers to a group (or genus) of retroviruses that give rise to slowly developing disease. Viruses included within this group include HW (human immunodeficiency virus; including but not limited to HW type 1 and HW type 2), the etiologic agent of the human acquired immunodeficiency syndrome (AIDS); visna-maedi, which causes encephalitis (visna) or pneumonia (maedi) in sheep; the caprine arthritis-encephalitis virus, which causes immune deficiency, arthritis, and encephalopathy in goats; equine infectious anemia virus (EIAV), which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SW), which cause immune deficiency and encephalopathy in sub-human primates. Diseases caused by these viruses are characterized by a long incubation period and protracted course. Usually, the viruses latently infect monocytes and macrophages, from which they spread to other cells. HW, FW, and SW also readily infect T lymphocytes (i.e., T-cells). In one embodiment of the invention, the lentivirus is not HW.

The term "promoter" as used herein refers to a recognition site of a DNA strand to which the RNA polymerase binds. The promoter forms an initiation complex with RNA polymerase to initiate and drive transcriptional activity. The complex can be modified by activating sequences termed "enhancers" or inhibitory sequences termed "silencers".

The terms "transformation," "transfection," and "transduction" refer to introduction of a nucleic acid, e.g., a viral vector, into a recipient cell.

As used herein, the term "subject" includes warm-blooded animals, preferably mammals, including humans. In a preferred embodiment, the subject is a primate. In an even more preferred embodiment, the primate is a human.

As used herein, the various forms of the term "modulate" are intended to include stimulation (e.g., increasing or upregulating a particular response or activity) and inhibition (e.g., decreasing or downregulating a particular response or activity).

As used herein, the term 417 contacting" (i.e., contacting a cell with an agent) is intended to include incubating the agent and the cell together in vitro (e.g., adding the agent to cells in culture) or administering the agent to a subject such that the agent and cells of the subject are contacted in vivo. The term "contacting" is not intended to include exposure of cells to an agent that may occur naturally in a subject (i.e., exposure that may occur as a result of a natural physiological process).

As used herein, the term "administering" to a subject includes dispensing, delivering or applying a composition capable of enhancing the intracellular generation and/or uptake of glucose, NADPH, pyruvate, and/or lactate to a subject by any suitable route for delivery of the composition to the desired location in the subject, including delivery by intraocular administration or intravenous administration. Alternatively or in combination, delivery is by the topical, parenteral or oral route, intracerebral injection, intramuscular injection, subcutaneous/intradermal injection, intravenous injection, buccal administration, transdermal delivery and administration by the rectal, colonic, vaginal, intranasal or respiratory tract route.

Various additional aspects of the methods of the invention are described in further detail in the following subsections.

Methods Of The Invention

The present invention provides methods for inhibiting starvation of a cell, e.g., a neuronal cell, which generally comprise contacting a cell with an agent which enhances the intracellular generation and/or uptake of glucose, pyruvate, lactate, and/or NADPH in the cell.

The present invention also provides methods for treating or preventing a disorder associated with starvation of a cell in a subject. The methods generally comprise administering to the subject an agent which enhances the intracellular generation and/or uptake of glucose, pyruvate, lactate, and/ or NADPH.

In another aspect, the present invention provides methods for treating or preventing retinitis pigmentosa in a subject. Such methods generally comprise administering to the subject an agent which enhances the intracellular generation and/or uptake of glucose, pyruvate, lactate, and/or NADPH.

The present invention further provides methods for prolonging the viability of a cone cell. The methods generally comprise contacting the cell with an agent which enhances the intracellular generation and/or uptake of glucose, pyruvate, lactate, and/or NADPH.

In one embodiment, the methods described herein can be performed in vitro. For example, intracellular levels of glucose, pyruvate, lactate, and/or NADPH can be modulated in a cell in vitro and then the treated cells can be administered or re-administered to a subject. In one embodiment, the cell is a mammalian cell, e.g., a human cell. For practicing the methods in vitro, cells can be obtained from a subject by standard methods and incubated (e.g., cultured) in vitro with an agent which stimulates intracellular levels of glucose, pyruvate, lactate, and/or NADPH. Methods for isolating cells are well known in the art. The cells can be readministered to the same subject, or another subject which is compatible with the donor of the cells.

For administration of cells to a subject, it may be preferable to first remove residual agents in the culture from the cells before administering them to the subject. This can be done, for example, by gradient centrifugation of the cells or by washing of the tissue. Methods for the ex vivo genetic modification of cells followed by re-administration to a subject are well known in the art and described in, for example, U.S. Pat. No. 5,399,346 the entire contents of which are incorporated herein by reference.

In one embodiment, the invention allows for modulation of intracellular levels of glucose, pyruvate, lactate, and/or NADPH in vivo, by administering to a subject a therapeutically effective amount of an agent as described herein. For example, intracellular levels of glucose, pyruvate, lactate, and/or NADPH can be modulated to treat or prevent a disorder associated with cellular starvation.

The claimed methods of modulation are not meant to include naturally occurring events. For example, the term "agent" or "modulator" is not meant to embrace endogenous mediators produced by the cells of a subject.

Application of the methods of the invention for the treatment and/or prevention of a disorder can result in curing the disorder, decreasing at least one symptom associated with the disorder, either in the long term or short term or simply a transient beneficial effect to the subject. Accordingly, as used herein, the terms "treat," "treatment" and "treating" include the application or administration of agents, as described herein, to a subject who is suffering from a disorder associated with starvation of a cell, or who is susceptible to such conditions with the purpose of curing, healing, alleviating, relieving, altering, remedying, ameliorating, improving or affecting such conditions or at least one symptom of such conditions. As used herein, the condition is also "treated" if recurrence of the condition is reduced, slowed, delayed or prevented.

Subjects suitable for treatment using the regimens of the present invention should have or are susceptible to developing disorders associated with cellular starvation, e.g., neuronal cellular starvation, for example, retinal disorders. For example, subjects may be genetically predisposed to development of the disorders. Alternatively, abnormal progression of the following factors including, but not limited to visual acuity, the rate of death of cone and/or rod cells, night vision, peripheral vision, attenuation of the retinal vessels, and other ophthalmoscopic factors associated with retinal disorders such as retinitis pigmentosa may indicate the existence of or a predisposition to a retinal disorders. Other art recognized symptoms or risk factors, as associated with the development of or predisposition to the particular disorder, for example, Alzheimer's Disease or a stroke, heart attack, diabetes, Parkinson's, may be monitored as well known in the art.

The agents, as described herein, may be administered as necessary to achieve the desired effect and depend on a variety of factors including, but not limited to, the severity of the condition, age and history of the subject and the nature of the composition, for example, the identity of the genes or the affected biochemical pathway. In various embodiments, the compositions may be administered at least two, three, four, five or six times a day. Additionally, the therapeutic or preventative regimens may cover a period of at least about 2, 3, 4, 5, 6, 7, 8, 9, 10, 11, 12, 13, 14, 15, 16, 17, 18, 19, 20, 21, 22, 23 or 24 weeks.

The ability of an agent to upregulate intracellular levels of glucose, pyruvate, lactate, and/or NADPH can be determined as described herein, e.g., by determining the ability of the agent to modulate: cell viability (e.g., modulation of apoptosis), cleavage of LaminA or Caspase 3; expression of Opn1sw, Opn1mw, LAMP-2A, LAMP-2B, or LAMP-2C; protein production of LAMP-2A, LAMP-2B, LAMP-2C, HIF1-$\alpha$, or GLUT1; phosphorylation of mTOR, S6K1, AMPK, PTEN, or Akt; phospholipid production; production of reactive oxygen species; and/or the expression and protein synthesis of photoreceptor specific opsins.

In various embodiments, the methods of the present invention further comprise monitoring the effectiveness of treatment. For example, visual acuity, the rate of death of cone and/or rod cells, night vision, peripheral vision, attenuation of the retinal vessels, and other ophthalmoscopic changes associated with retinal disorders such as retinitis pigmentosa may be monitored to assess the effectiveness of treatment. Additionally, the rate of death of cells associated with the particular disorder that is the subject of treatment and/or prevention, may be monitored. Alternatively, the viability of such cells may be monitored, for example, as measured by phospholipid production. The assays described in the Examples section below may also be used to monitor the effectiveness of treatment.

In one embodiment, the agent is a nucleic acid molecule. In a particular embodiment, the nucleic acid molecule is a glucose transporter. For example, glucose transporters for use in the present invention may belong to the GLUT family of transporters (including at least one of GLUT1, GLUT2, GLUT3, GLUT4, GLUT5, GLUT6, GLUT7, GLUT8, GLUT9, GLUT10, GLUT11, GLUT12, GLUT13, and GLUT14), encoded by the SLC2 family of genes (including at least one of SLC2A1, SLC2A2, SLC2A3, SLC2A4, SLC2A5, SLC2A6, SLC2A7, SLC2A8, SLC2A9, SLC2A10, SLC2A11, SLC2A12, SLC2A13, and SLC2A14), which upregulate the cellular uptake of glucose by facilitated diffusion. In a particular embodiment, the nucleic acid molecule is SLC2A1 encoding the GLUT1 transporter.

The amino acid sequences of the GLUT family of transporters are known and can be found in, for example, GenBank Accession Nos. GI:166795299 (GLUT1; GI:4557851 (GLUT2; GI:5902090 (GLUT3; GI:4507011 (GLUT4); GI:4507013 (GLUT5, isoform 1); GI:207447703 (GLUT5, isoform 2); GI:223029432 (GLUT6, isoform 1); GI:223029430 (GLUT6, isoform 2); GI:134053883 (GLUT7); GI:21361449 (GLUT8); GI:47933387 (GLUT9, isoform 1); GI:47933389 (GLUT9, isoform 2); GI:13540547 (GLUT10); GI:190684655 (GLUT11, isoform a); GI:68226418 (GLUT11, isoform b); GI:68226420 (GLUT11, isoform c); GI:21553331 (GLUT12); GI:203098995 (GLUT13); and GI:23592238 (GLUT14).

The nucleotide sequences of the SLC2 family of transporters are known and can be found in, for example, GenBank Accession Nos. GI:166795298 (SLC2A1); GI:4557850 (SLC2A2); GI:221136810 (SLC2A3); GI:83722278 (SLC2A4); GI:207446701 (SLC2A5, variant 1); GI:207447702 (SLC2A5, variant 2); GI:223029431 (SLC2A6, variant 1); GI:223029429 (SLC2A6, variant 2); GI:134053882 (SLC2A7); GI:51870928 (SLC2A8); GI:47933386 (SLC2A9, variant 1); GI:47933388 (SLC2A9, variant 2); GI:39777591 (SLC2A1); GI:190684654 (SLC2A11, variant 1); GI:190684652 (SLC2A11, variant 2); GI:190684653 (SLC2A11, variant 3); GI:93277101 (SLC2A12); GI:203098994 (SLC2A13); and GI:24475843 (SLC2A14).

In another embodiment, the stimulatory agent is a nucleic acid molecule involved in promoting gluconeogenesis, thereby increasing metabolic flux through gluconeogenesis, and/or reducing metabolic flux through glycolysis. As is well known in the art, gluconeogenesis promotes the generation of glucose, whereas glycolysis promotes the degradation of glucose. Accordingly, the nucleic acid molecule may be a gluconeogenic gene including, but not limited to, pyruvate carboxylase, phosphoenolpyruvate carboxykinase and fructose 1,6-bisphosphatase. In a particular embodiment, one or more gluconeogenic genes may be utilized.

The nucleotide and amino acid sequences of pyruvate carboxylase are known and can be found in, for example, GenBank Accession Nos. GI:106049294 (variant 1), GI:106049291 (variant 2), and GI:106049527 (variant 3). The nucleotide and amino acid sequences of phosphoenolpyruvate carboxykinase are known and can be found in, for example, GenBank Accession Nos. GI:66346720 (variant 1) and GI:66346722 (variant 2). The nucleotide and amino acid sequences of fructose 1,6-bisphosphatase are known and can be found in, for example, GenBank Accession Nos. GI:160298191 (FBP1, variant 1), GI:189083691 (FBP1, variant 2), and GI:22907027 (FBP2).

The present invention further provides methods for increasing intracellular levels of lactate, which, in turn, can serve as an important precursor for gluconeogenesis and the production of glucose. As is well known in the art, lactate is converted to pyruvate, which, in turn, is converted to oxaloacetate for entry into gluconeogenesis and the production of glucose. Accordingly, in one embodiment, the agent may be involved in increasing the uptake of lactate. For example, the agent may be a stimulatory agent, e.g., a nucleic acid molecule that, for example, encodes a lactate transporter (a monocarboxylic acid transporter). In another embodiment, the agent may be an inhibitory agent that downregulates a negative regulator of, for example, a lactate transporter. In yet another embodiment, the agent may be a stimulatory agent, e.g., glutamate, that, for example, increases extracellular lactate concentrations my causing its release from neighboring cells, e.g., Muller glia and/or astrocytes.

The nucleotide and amino acid sequences of members of the monocarboxylic acid transporter family are known and can be found in, for example, GenBank Accession Nos. GI:115583684 (SLC16A1, variant 1) and GI:262073006 (SLC16A1, variant 2); GI:164663748 (SLC16A2); GI:109288011 (SLC16A3, variant 1), GI:109288008 (SLC16A3, variant 2), and GI:109288009 (SLC16A3, variant 3); GI:4759113 (SLC16A4); GI:20127461 (SLC16A5); GI:141802120 (SLC16A6); GI:34222196 (SLC16A7); GI:114796625 (SLC16A8); GI:197383642 (SLC16A9); GI:221139821 (SLC16A10); GI:23503292 (SLC16A11); GI:157041232 (SLC16A12); GI:222537717 (SLC16A13); and GI:42415495 (SLC16A14).

The present invention further provides methods for increasing intracellular levels of NADPH, which, as described above, is important for the generation of phospholipids, the primary component of cellular membranes. Moreover, NADPH serves to detoxify free oxygen radicals which can be damaging to cells, e.g., neuronal cells. For example, after rod cells die, excess oxygen, which is subsequently converted to free oxygen radicals in the presence of light or by phototransduction, accumulates around cone cells. The presence of free oxygen radicals diverts available NADPH from, for example, the generation of phospholipids, thereby reducing the viability of cells. By enhancing the levels of NADPH, in accordance with the methods of the present invention, one can serve to increase phospholipid production and, in turn, cellular membrane generation and, further, to detoxify otherwise damaging free oxygen radicals.

Accordingly, in a particular embodiment, the methods of the present invention are directed to enhancing the ability of a cell to generate NADPH. For example, increasing cellular levels of glucose by the methods described herein serves to increase metabolic flux through the pentose phosphate pathway, thereby generating increased levels of NADPH. Alternatively or in combination, cells suffering from starvation or subject suffering from disorders associated with such starvation can be contacted with agents, e.g., stimulatory agents, which directly enhance intracellular levels of NADPH. For example, the stimulatory agent may be a nucleic acid molecule, e.g., a nucleic acid molecule encoding malic enzyme, which serves to convert malate to pyruvate and generate NADPH as a byproduct. In another embodiment, the stimulatory agent may be, e.g., insulin or triiodothyronine (T3) that e.g., stimulates the expression of malic enzyme. In yet another embodiment, the stimulatory agent may be glutamate that, e.g., stimulates lactate release from neighboring cells.

The nucleotide and amino acid sequences of members of the malic enzyme family are known and can be found in, for example, GenBank Accession Nos. GI:112382261 (ME1), GI:270265877 (ME2, variant 1), GI:270265878 (ME2, variant 2), GI:62420879 (ME3, variant 1), GI:62420881 (ME3, variant 2), and GI:239049446 (ME3, variant 3).

In another embodiment, the agent is an inhibitory agent which downregulates a negative regulator of the synthesis of, for example, malate. In one aspect, the present invention is directed to the use of an agent, e.g., a nucleic acid molecule, vectors and compositions comprising such nucleic acid molecules, to prolong the viability of cone cells. In one embodiment, the viability or survival of cones cells is short term viability, e.g., about 1 week, about 2 weeks, about 3 weeks, about 4 weeks, about 5 weeks, about 6 weeks, about 7 weeks, about 8 weeks, about 3 years, about 4 years, about 5 years, about 10 years, about 15, years, about 20 years, about 25 years, about 30 years, about 40 years, about 50 years, about 60 years, about 70 years, and about 80 years.

The methods of the invention described above, thus, may be used to treat or prevent starvation of cells and disorders associated with such starvation. In one embodiment, the disorder is a neurodegenerative disorder, such as a stroke or Alzheimer's Disease. In other embodiments, the disorder is an ocular disorder including, but not limited to, retinitis pigmentosa, age related macular degeneration, cone rod dystrophy, rod cone dystrophy and glaucoma. In further embodiments, the disorder is an ocular disorder associated with decreased viability of cone and/or rod cells. In yet another embodiment, the disorder is a genetic disorder.

In one embodiment, the invention is directed to a method of treating or preventing a disorder associated with starvation of a neuronal cell, for example, retinitis pigmentosa, in a subject by selecting a subject who is susceptible to the development of the disorder and administering to the subject an effective amount of the nucleic acid molecules, vectors and/or compositions of the present invention, thereby treating or preventing the disorder in the subject.

The overall strategy to save neurons from degeneration is to supply them with the genes that will allow them to make up for deficits in the building materials that are required to maintain function and survival. Genes encoding gluconeogenic enzymes, glucose transporter(s), and/or NADPH synthetic enzymes are those targeted for delivery. Vectors derived from AAV, adenoviruses, lentiviruses and/or other types of retroviruses, as well as electroporation can be used.

Age related macular degeneration is another disease in which cones die. The early signs of this disease are drusen, which are accumulations of lipids and proteins in the region between the choroidal vasculature, the retinal pigmented epithelium, and photoreceptors. The drusen likely impedes the flow of nutrients through the RPE to the photoreceptors. Treatments with the gluconeogenic enzymes would prevent the rapid death of nutritionally deprived cones. In addition to cone photoreceptor survival, the survival of several other types of neurons has been proposed to result form lack of glucose and/or oxygen, or other nutrients.

Glaucoma is another disease that can be treated using the methods of the present invention. Glaucoma is a disease in which ganglion cells die, and high intraocular pressure often accompanies ganglion cell death. Compromised blood flow due to increased pressure might cause the ganglion cells to die. Gluconeogenic enzymes are expected to prolong their survival by allowing lactate made by Muller glial cells to be utilized for glucose synthesis.

Stroke is yet another disease that can be treated using the methods of the present invention. Stroke is caused by a compromised blood supply. Given that neurons expend energy rapidly, a depletion in glucose and oxygen can lead to rapid death. Supplying the genes for gluconeogenesis quickly after a stroke will prevent neuronal death.

Similarly, heart attack is caused, at least in part, by compromised blood supply and, thus, depletion in glucose and oxygen often leading to heart muscle death. Accordingly, supplying the genes for gluconeogenesis quickly after a heart attack will prevent heart cell death Alzheimer's Disease may be caused, at least in part, by a reduction in energy supply. Physical and mental activity later in life is believed to supply good blood flow to the areas being used, thereby helping those cells maintain sufficient nutrition to prevent neuronal death. Providing cells with gluconeogenic genes is expected to also prevent this type of degeneration.

Injuries, such as burns and other wounds will also be benefited by the methods of the invention in that increases in glucose, pyruvate, lactate, and/or NADPH will allow the production of all cellular intermediates for cellular repair necessary for wound healing.

Agents for Use in the Methods of the Invention

Stimulatory Agents

The methods of the invention may use stimulatory agents which upregulate or enhance the intracellular generation and/or uptake of glucose, pyruvate, lactate, and/or NADPH in a cell. Examples of such stimulatory agents include proteins, nucleic acid molecules, e.g., expression vectors comprising nucleic acid molecules, and chemical agents that stimulate expression and/or activity of a protein which enhances the intracellular generation and/or uptake of glucose, pyruvate, lactate, and/or NADPH in a cell.

A preferred stimulatory agent is a nucleic acid molecule encoding a protein of interest. For example, a cDNA (full length or partial cDNA sequence) is cloned into a recombinant expression vector and the vector is transfected into cells using standard molecular biology techniques. The cDNA can be obtained, for example, by amplification using the polymerase chain reaction (PCR) or by screening an appropriate cDNA library.

Following isolation or amplification of a cDNA, the DNA fragment is introduced into a suitable expression vector. For example, nucleic acid molecules encoding a protein of interest in the form suitable for expression of the protein in a host cell, can be prepared using nucleotide sequences based on the nucleic acid sequence of a nucleic acid molecule encoding the protein of interest.

In one embodiment, a stimulatory agent can be present in an inducible construct. In another embodiment, a stimulatory agent can be present in a construct which leads to constitutive expression.

In one embodiment, the nucleic acid molecules of the invention may be delivered to cells, e.g., neuronal cells, or to subjects using a viral vector, preferably one whose use for gene therapy is well known in the art. Techniques for the formation of vectors or virions are generally described in "Working Toward Human Gene Therapy," Chapter 28 in Recombinant DNA, 2nd Ed., Watson, J. D. et al., eds., New York: Scientific American Books, pp. 567-581 (1992). An overview of suitable viral vectors or virions is provided in Wilson, J. M., Clin. Exp. Immunol. 107(Suppl. 1):31-32 (1997), as well as Nakanishi, M., Crit. Rev. Therapeu. Drug Carrier Systems 12:263-310 (1995); Robbins, P. D., et al., Trends Biotechnol. 16:35-40 (1998); Zhang, J., et al., Cancer Metastasis Rev. 15:385-401 (1996); and Kramm, C. M., et al., Brain Pathology 5:345-381 (1995). Such vectors may be derived from viruses that contain RNA (Vile, R. G., et al., Br. Med. Bull. 51:12-30 (1995)) or DNA (Ali M., et al., Gene Ther. 1:367-384 (1994)).

Examples of viral vector systems utilized in the gene therapy art and, thus, suitable for use in the present invention, include the following: retroviruses (Vile, R. G., supra; U.S. Pat. Nos. 5,741,486 and 5,763,242); adenoviruses (Brody, S. L., et al., Ann. N.Y. Acad. Sci. 716: 90-101 (1994); Heise, C. et al., Nat. Med. 3:639-645 (1997)); adenoviral/retroviral chimeras (Bilbao, G., et al., FASEB J.

11:624-634 (1997); Feng, M., et al., Nat. Biotechnol. 15:866-870 (1997)); adeno-associated viruses (Flotte, T. R. and Carter, B. J., Gene Ther. 2:357-362 (1995); U.S. Pat. No. 5,756,283); herpes simplex virus I or II (Latchman, D. S., Mol. Biotechnol. 2:179-195 (1994); U.S. Pat. No. 5,763, 217; Chase, M., et al., Nature Biotechnol. 16:444-448 (1998)); parvovirus (Shaughnessy, E., et al., Semin Oncol. 23:159-171 (1996)); reticuloendotheliosis virus (Donburg, R., Gene Therap. 2:301-310 (1995)). Extrachromosomal replicating vectors may also be used in the gene therapy methods of the present invention. Such vectors are described in, for example, Calos, M. P. (1996) *Trends Genet.* 12:463-466, the entire contents of which are incorporated herein by reference. Other viruses that can be used as vectors for gene delivery include poliovirus, papillomavirus, vaccinia virus, lentivirus, as well as hybrid or chimeric vectors incorporating favorable aspects of two or more viruses (Nakanishi, M. (1995) *Crit. Rev. Therapeu. Drug Carrier Systems* 12:263-310; Zhang, J., et al. (1996) *Cancer Metastasis Rev.* 15:385-401; Jacoby, D. R., et al. (1997) *Gene Therapy* 4:1281-1283).

In a particular embodiment, the viral vector for use in the methods of the present invention is an AAV vector. In particular embodiments, the viral vector is an AAV2/5 or AAV2/8 vector. Such vectors are described in, for example, U.S. Pat. No. 7,056,502, the entire contents of which are incorporated herein by reference.

The vector will include one or more promoters or enhancers, the selection of which will be known to those skilled in the art. Suitable promoters include, but are not limited to, the retroviral long terminal repeat (LTR), the SV40 promoter, the human cytomegalovirus (CMV) promoter, and other viral and eukaryotic cellular promoters known to the skilled artisan.

Guidance in the construction of gene therapy vectors and the introduction thereof into affected animals for therapeutic purposes may be obtained in the above-referenced publications, as well as in U.S. Pat. Nos. 5,631,236, 5,688,773, 5,691,177, 5,670,488, 5,529,774, 5,601,818, and PCT Publication No. WO 95/06486, the entire contents of which are incorporated herein by reference.

Generally, methods are known in the art for viral infection of the cells of interest. The virus can be placed in contact with the neuronal cell of interest or alternatively, can be injected into a subject suffering from a disorder associated with neuronal cellular starvation.

In one aspect of the invention, the therapeutic nucleic acid molecule or the vector containing the same will be in the form of a pharmaceutical composition containing a pharmaceutically acceptable carrier. As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for intraocular, parenteral, intravenous, intraperitoneal, topical, or intramuscular administration. In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the gene therapy vector, use thereof in the pharmaceutical compositions of the invention is contemplated. Supplementary active compounds can also be incorporated into the compositions.

In a particular embodiment, the pharmaceutical compositions of the present invention would be administered in the form of injectable compositions. The vector can be prepared as an injectable, either as liquid solutions or suspensions. The preparation may also be emulsified. Suitable excipients are, for example, water, saline, dextrose, glycerol, ethanol, or the like and combinations thereof. In addition, if desired, the preparation may contain minor amounts of auxiliary substances such as wetting or emulsifying agents, pH-buffering agents, adjuvants or immunopotentiators.

In a particular embodiment, the nucleic acid molecules and/or vectors are incorporated in a composition suitable for intraocular administration. For example, the compositions may be designed for intravitreal, subconjuctival, sub-tenon, periocular, retrobulbar, suprachoroidal, and/or intrascleral administration, for example, by injection, to effectively treat the retinal disorder. Additionally, a sutured or refillable dome can be placed over the administration site to prevent or to reduce "wash out", leaching and/or diffusion of the active agent in a non-preferred direction.

Relatively high viscosity compositions, as described herein, may be used to provide effective, and preferably substantially long-lasting delivery of the nucleic acid molecules and/or vectors, for example, by injection to the posterior segment of the eye. A viscosity inducing agent can serve to maintain the nucleic acid molecules and/or vectors in a desirable suspension form, thereby preventing deposition of the composition in the bottom surface of the eye. Such compositions can be prepared as described in U.S. Pat. No. 5,292,724, the entire contents of which are hereby incorporated herein by reference.

In general, the nucleic acid molecule is provided in a therapeutically effective amount to elicit the desired effect, e.g., enhancing intracellular levels of glucose, pyruvate, lactate, and/or NADPH. The quantity of the vector to be administered, both according to number of treatments and amount, will also depend on factors such as the clinical status, age, and weight of the subject to be treated, and the severity of the disorder. Precise amounts of active ingredient required to be administered depend on the judgment of the gene therapist and will be particular to each individual patient. Generally, the viral vector is administered in titers ranging from about $1 \times 10^5$, about $1.5 \times 10^5$, about $2 \times 10^5$, about $2.5 \times 10^5$, about $3 \times 10^5$, about $3.5 \times 10^5$, about $4 \times 10^5$, about $4.5 \times 10^5$, about $5 \times 10^5$, about $5.5 \times 10^5$, about $6 \times 10^5$, about $6.5 \times 10^5$, about $7 \times 10^5$, about $7.5 \times 10^5$, about $8 \times 10^5$, about $8.5 \times 10^5$, about $9 \times 10^5$, about $9.5 \times 10^5$, about $1 \times 10^6$, about $1.5 \times 10^6$, about $2 \times 10^6$, about $2.5 \times 10^6$, about $3 \times 10^6$, about $3.5 \times 10^6$, about $4 \times 10^6$, about $4.5 \times 10^6$, about $5 \times 10^6$, about $5.5 \times 10^6$, about $6 \times 10^6$, about $6.5 \times 10^6$, about $7 \times 10^6$, about $7.5 \times 10^6$, about $8 \times 10^6$, about $8.5 \times 10$, about $9 \times 10^6$, about $9.5 \times 10^6$, about $1 \times 10^7$, about $1.5 \times 10^7$, about $2 \times 10^7$, about $2.5 \times 10^7$, about $3 \times 10^7$, about $3.5 \times 10^7$, about $4 \times 10^7$, about $4.5 \times 10^7$, about $5 \times 10^7$, about $5.5 \times 10^7$, about $6 \times 10^7$, about $6.5 \times 10^7$, about $7 \times 10^7$, about $7.5 \times 10^7$, about $8 \times 10^7$, about $8.5 \times 10^7$, about $9 \times 10^7$, about $9.5 \times 10^7$, about $1 \times 10^8$, about $1.5 \times 10^8$, about $2 \times 10^8$, about $2.5 \times 10^8$, about $3 \times 10^8$, about $3.5 \times 10^8$, about $4 \times 10^8$, about $4.5 \times 10^8$, about $5 \times 10^8$, about $5.5 \times 10^8$, about $6 \times 10^8$, about $6.5 \times 10^8$, about $7 \times 10^8$, about $7.5 \times 10^8$, about $8 \times 10^8$, about $8.5 \times 10^8$, about $9 \times 10^8$, about $9.5 \times 10^8$, and about $1 \times 10^9$ colony forming units (cfu) per ml, although ranges may vary. Preferred titers will range from about $1 \times 10^6$ to about $1 \times 10^8$ cfu/ml.

In one embodiment, a packaging cell line is transduced with a retroviral vector carrying the desired nucleic acid molecule to form a producer cell line. The packaging cells may be transduced by any means known in the art, including, e.g., electroporation, $CaPO_4$ precipitation, or the use of liposomes. Examples of packaging cells that may be transfected include, but are not limited to, BOSC23, Bing, PE501, PA317, .PSI.-2, .PSI.-AM, PA12, T19-14X, VT-19-17-H2, .PSI.-CRE, .PSI.-CRIP, GP+E86, GP+envAm12, and DAN cell lines. Guidance on retroviral producing packaging cells and how to construct them can be found in Short et al., J. Neurosci. Res. 27:427-433 (1990); Miller, A. D., Human Gene Ther. 1:5-14 (1990); Danos, 0, "Construction of Retroviral Packaging Cell Lines," in Methods in Molecular Biology (M. Collins, ed.), Vol. 8, The Humana Press Inc., Clifton, N.J., 17-26 (1991); Murdoch, B., et al., Gene Therapy 4:744-749 (1997); and U.S. Pat. Nos. 5,529,774 and 5,591,624, the entire contents of which are incorporated herein by reference.

Retroviral vectors have also been successfully packaged with a vesicular stomatitis virus (VSV) envelope glycoprotein G ("pseudotyping"). These vectors are more stable and can be concentrated to $10^9$ cfu/ml, allowing them to be injected directly (Burns, J. C. et al. (1993) Proc. Natl. Acad. Sci. USA 90:8033-8037).

The producer cells can then be grafted near or into the desired location, for example, intraocularly. Direct injection of high titer retroviral producer cells (Murdoch, B., et al., Gene Ther. 4:744-749 (1997); Onodera, M., et al., Hum Gene Ther. 8:1189-1194 (1997)) should allow for efficient in situ infection with the retroviral sequences (Rainov, N. G., et al., Cancer Gene Ther. 3:99-106 (1996); Ram, Z., et al., Cancer Res. 53:83-88 (1993)). Producer cells injected intraocularly do not generally migrate from the site of injection. Moreover, although they may be rejected by the host, this does not occur for 5-10 days, by which time retroviral infection of nearby cells will have occurred (Ram, Z., et al., J. Neurosurg. 79:400-407 (1993)). In general, vector producer cell (VPC) dosages range from about $2.5 \times 10^8$, about $1 \times 10^8$, about $1.5 \times 10^8$, about $2 \times 10^8$, about $2.5 \times 10^8$, about $3 \times 10^8$, about $3.5 \times 10^8$, about $4 \times 10^8$, about $4.5 \times 10^8$, about $5 \times 10^8$, about $5.5 \times 10^8$, about $6 \times 10^8$, about $6.5 \times 10^8$, about $7 \times 10^8$, about $7.5 \times 10^8$, about $8 \times 10^8$, about $8.5 \times 10^8$, about $9 \times 10^8$, about $9.5 \times 10^8$, and about $1 \times 10^9$ VPCs. The exact amount of producer cells will ultimately be determined by the skilled artisan based on numerous factors, including, but not limited to, the available injectable volume, clinical status of the patient, and the severity of the disorder.

Preferably, the viral genomes of the viral vectors used in the invention should be modified to remove or limit their ability to replicate, however, replication conditional viruses will also be useful in the present invention, as will replicating vectors that are capable of targeting certain cells. (See, e.g., Zhang, J. et al. (1996) Cancer Metastasis Rev. 15:385-401).

In one embodiment, a single viral vector is used to carry multiple nucleic acid molecules, for example, genes encoding pyruvate carboxylase and phosphoenolpyruvate carboxykinase. In another embodiment, two viral vectors are used each carrying one or more genes of interest. If two viral vectors are used, they can be derived from the same or a different type of virus, and can be administered simultaneously or sequentially (i.e., without regard for a specific order).

The nucleic acid molecules can also be delivered using non-viral methods for gene transfer, preferably those whose use in gene therapy is known in the art (Nakanishi, M., Crit. Rev. Therapeu. Drug Carrier Systems 12:263-310 (1995); Abdallah, B., et al., Biol Cell 85:1-7 (1995); Zhang, J., et al., Cancer Metastasis Rev. 15:385-401 (1996); Philips, S. C., Biologicals 23:13-16 (1995); Lee, R. J. and Huang, L., Crit. Rev. Ther. Drug Carrier Syst. 14:173-206 (1997)). Examples of such non-viral vectors for gene delivery include prokaryotic vectors, cationic liposomes, DNA-protein complexes, non-viral T7 autogene vectors (Chen, X., et al., Hum. Gene Ther. 9:729-736 (1998)), fusogenic liposomes, direct injection of nucleic acid ("naked DNA"), particle or receptor-mediated gene transfer, hybrid vectors such as DNA-adenovirus conjugates or other molecular conjugates involving a non-viral and viral component, starburstpolyamidoamine dendrimers (Kukowska-Latallo, J. F., et al., Proc Natl Acad Sci USA 93:4897-4902 (1996); Tang, M. X., et al., Bioconjug. Chem. 7:703-714 (1996)), cationic peptides (Wyman, T. B., et al., Biochemistry 36:3008-3017 (1997)), mammalian artificial chromosomes (Ascenzioni, F., et al., Cancer Lett. 118:135-142 (1997)), and nanoparticles (Parker Read et al. J. Gene Med. 12:86-96 (2010); Frajo et al. PlosOne 1:E38 (2006).

In addition, the present invention provides an embodiment of the foregoing methods wherein the nucleic acid molecules are delivered using any cellular vector, preferably one whose use for gene therapy is well-established for those skilled in the art. Examples of such cellular vectors for gene therapy include endothelial cells (Rancourt, C., et al., Clin. Cancer Res. 4:265-270 (1998); Qjeifo, J. O., et al., Cytokines Mol. Ther. 2:89-101 (1996)) and macrophages including tumor-infiltrating macrophages (Zufferey, R., et al., Nat. Biotechnol. 15:871-875 (1997); Naldini, L., et al., Science 272:263-267 (1996)), each of which may be modified using viral or non-viral vectors to carry the desired nucleic acid molecules, and thus express the desired gene products. Other suitable non-viral vectors will be readily apparent to the skilled artisan.

Gene delivery can be enhanced by including an internal ribosome entry site (IRES) sequence to achieve coordinate expression of multiple genes on a bicistronic message. IRESs are sequences containing 500-600 bp that are typical of the 5' nontransduced regions of picornaviruses, including the polio- and encephalomyocarditis viruses (EMCV). See, e.g., Ghattas, I. R., et al., Molecular and Cellular Biology 11:5848-5859 (1991); Morgan, R. A., et al., Nucleic Acids Research 20:1293-1299 (1992). This approach has been used for efficient retroviral coexpression of the two subunits of interleukin-12 (Tahara, H., et al., J. Immunol. 154:6466-6474 (1995)). Similarly, a viral sequence, the picornavirus 2A sequence, can be used to create mRNAs encoding more than one protein. The viral 2A peptide is 16-20 amino acids and can be employed as a cleavage peptide located between two proteins of interest, where it promotes their cleavage into two separate proteins (Furler et al. Gene Ther. 8:864-873 (2001). Another alternative is for the vector to contain multiple genes under the control of distinct promoters.

Other examples of stimulatory agents for enhancing the intracellular generation and/or uptake of glucose, pyruvate, lactate, and/or NADPH in a cell is a small molecule compound, an antibody, or other protein as described below.

Inhibitory Agents

The methods of the invention may also use agents which inhibit a negative regulator of the intracellular generation and/or uptake of glucose, pyruvate, lactate, and/or NADPH. Such agents can be, for example, intracellular binding molecules that act to specifically inhibit the expression, processing, post-translational modification, or activity of a negative regulator of the intracellular generation and/or uptake of glucose, pyruvate, lactate, and/or NADPH. As used herein, the term "intracellular binding molecule" is intended to include molecules that act intracellularly to, for example, inhibit the processing expression or activity of a protein by binding to the protein or to a nucleic acid (e.g. an mRNA molecule) that encodes the protein.

Examples of intracellular binding molecules, described in further detail below, include antisense nucleic acids, intracellular antibodies, peptidic compounds, and chemical agents that specifically inhibit the activity of a negative regulator of intracellular levels of glucose, pyruvate, lactate, and/or NADPH.

In one embodiment, such an agent is an antisense nucleic acid molecule that is complementary to a gene encoding a negative regulator of intracellular levels of glucose, pyruvate, lactate, and/or NADPH, or to a portion of said gene, or a recombinant expression vector encoding the antisense nucleic acid molecule. The use of antisense nucleic acids to downregulate the expression of a particular protein in a cell is well known in the art (see e.g. Weintraub, H. et al., Antisense RNA as a molecular tool for genetic analysis, Reviews—Trends in Genetics, Vol. 1(1) 1986; Askari, F. K. and McDonnell, W. M. (1996) N. Eng J. Med. 334:316-318; Bennett, M. R. and Schwartz, S. M. (1995) Circulation 92:1981-1993; Mercola, D. and Cohen, J. S. (1995) Cancer Gene Ther.__:47-59; Rossi, J. J. (1995) Br. Med. Bull. 51:217-225; Wagner, R. W. (1994) Nature 372:333-335; each of which is incorporated herein by reference). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule.

Antisense sequences complementary to a sequence of an mRNA can be complementary to a sequence found in the coding region of the mRNA, the 5' or 3' untranslated region of the mRNA or a region bridging the coding region and an untranslated region (e.g. at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Antisense nucleic acids of the invention can be designed according to the rules of Watson and Crick base pairing. The antisense nucleic acid molecule can be complementary to the entire coding region of an mRNA, but more preferably is antisense to only a portion of the coding or noncoding region of an mRNA.

An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g. an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine. To inhibit expression in cells, one or more antisense oligonucleotides can be used.

Alternatively, an antisense nucleic acid can be produced biologically using an expression vector into which all or a portion of a cDNA has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. The antisense expression vector is prepared according to standard recombinant DNA methods for constructing recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector can be introduced into cells using a standard transfection technique.

Antisense nucleic acid molecules are typically administered to a subject or generated in situ such that they hybridize with or bind to cellular mRNA and/or genomic DNA encoding a protein to thereby inhibit expression of the protein, e.g. by inhibiting transcription and/or translation. The hybridization can be by conventional nucleotide complementarily to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g. by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, an antisense nucleic acid molecule that may be used in the methods of the invention is an α-anomeric nucleic acid molecule. An α-anomeric nucleic acid molecule forms specific double-stranded hybrids with complementary RNA in which, contrary to the usual, 8-units, the strands run parallel to each other (Gaultier et al. (1987) Nucleic Acids. Res. 15:6625-6641; incorporated herein by reference). The antisense nucleic acid molecule can also comprise a 2'-o-methylribonucleotide (Inoue et al. (1987) Nucleic Acids Res. 15:6131-6148; incorporated herein by reference) or a chimeric RNA-DNA analogue (Inoue et al. (1987) FEBS Lett. 215:327-330; incorporated herein by reference).

In still another embodiment, an antisense nucleic acid molecule that may be used in the methods of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g. hammerhead ribozymes (described in Haselhoff and Gerlach (1988) Nature 334:585-591; incorporated herein by reference)) can be used to catalytically cleave mRNA transcripts to thereby inhibit translation mRNAs. A ribozyme having specificity for an encoding nucleic acid molecule of interest can be designed based upon the nucleotide sequence of the cDNA. For example, a derivative of a Tetrahynena L-19 IVS RNA can be constructed in which the nucleotide sequence of the active site is complementary to the nucleotide sequence to be cleaved in, an encoding mRNA of interest. See, e.g. Cech et al. U.S. Pat. No. 4,987,071; Cech et al. U.S. Pat. No. 5,116,742; each of which is incorporated herein by reference. Alternatively, a mRNA of interest can be used to select a catalytic RNA having a specific ribonuclease activity from a pool of RNA molecules. See, e.g., Bartel, D. and Szostak, J. W. (1993) Science 261:1411-1418; incorporated herein by reference.

In another embodiment, a agent that promotes RNAi can be used to inhibit expression of a negative regulator of intracellular levels of glucose, pyruvate, lactate, and/or NADPH. RNA interference (RNAi is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287. 2431-2432 (2000); Zamore et al. Cell 101, 25-33 (2000). Tuschl et al. Genes Dev. 13. 3191-3197 (1999); Cottrell T R, and Doering T L. 2003. Trends Microbiol. 11:37-43; Bushman F. 2003. Mol. Therapy. 7:9-10; McManus M T and Sharp P A. 2002. Nat. Rev. Genet. 3:737-47; each of which is incorporated herein by reference). The process occurs when an endogenous ribonuclease cleaves the longer dsRNA into shorter, e.g. 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabsor Ambion. In one embodiment one or more of the chemistries described above for use in antisense RNA can be employed in molecules that mediate RNAi.

Antibodies can also be used as agents in the methods of the invention. In one embodiment, an antibody is an intracellular antibody that inhibits protein activity. Such an intracellular antibody is prepared using methods well known in the art which generally involve preparing a recombinant expression vector which encodes the antibody chains in a form such that, upon introduction of the vector into a cell, the antibody chains are expressed as a functional antibody in an intracellular compartment of the cell.

For inhibition of transcription factor activity according to the inhibitory methods of the invention, an intracellular antibody that specifically binds the protein is expressed within the nucleus of the cell. Nuclear expression of an intracellular antibody can be accomplished by removing from the antibody light and heavy chain genes those nucleotide sequences that encode the N-terminal hydrophobic leader sequences and adding nucleotide sequences encoding a nuclear localization signal at either the N- or C-terminus of the light and heavy chain genes (see e.g. Biocca et al. (1990) EMBO J. 9:101-108; Mhashilkar et al. (1995) EMBO J. 14:1542-1551; each of which is incorporated herein by reference). A preferred nuclear localization signal to be used for nuclear targeting of the intracellular antibody chains is the nuclear localization signal of SV40 Large T antigen (see Biocca et al. (1990) EMBO J. 9:101-108; Mhashilkar et al. (1995) EMBO J. 14:1542-1551; each of which is incorporated herein by reference).

To prepare an intracellular antibody expression vector, antibody light and heavy chain cDNAs encoding antibody chains specific for the target protein of interest, is isolated, typically from a hybridoma that secretes a monoclonal antibody specific for the protein. Antibodies can be prepared by immunizing a suitable subject, (e.g. rabbit, goat, mouse or other mammal), e.g., with a protein immunogen. An appropriate immunogenic preparation can contain, for example, recombinantly expressed protein or a chemically synthesized peptide. The preparation can further include an adjuvant, such as Freund's complete or incomplete adjuvant, or similar immunostimulatory compound. Antibody-producing cells can be obtained from the subject and used to prepare monoclonal antibodies by standard techniques, such as the hybridoma technique originally described by Kohler and Milstein (1975, Nature 256:495-497; incorporated herein by reference) (see also, Brown et al. (1981) J. Immunol. 127:539-46; Brown et al. (1980) J Biol Chem 255:4980-83; Yeh et al. (1976) PNAS76:2927-31; Yeh et al. (1982) Int. J. Cancer 29:269-75; each of which is incorporated herein by reference). The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387-402; M. L. Gefter et al. (1977) Somatic Cell Genet., 3:231-36; each of which is incorporated herein by reference). Briefly, an immortal cell line (typically a myeloma) is fused to lymphocytes (typically splenocytes) from a mammal immunized with a protein immunogen as described above, and the culture supernatants of the resulting hybridoma cells are screened to identify a hybridoma producing a monoclonal antibody that binds specifcally, a protein of interest. Any of the many well known protocols used for fusing lymphocytes and immortalized cell lines can be applied for the purpose of generating a monoclonal antibody (see, e.g. G. Galfre et al. (1977) Nature 266:550-52; Gefter et al. Somatic Cell Genet., cited supra; Lerner, Yale J. Biol. Med., cited supra; Kenneth, Monoclonal Antibodies, cited supra; each of which is incorporated herein by reference). Moreover, the ordinary skilled artisan will appreciate that there are many variations of such methods which also would be useful.

Typically, the immortal cell line (e.g. a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g. the P3-NS1/1-Ag4-1, P3-x63-Ag8.653 or Sp2/O— Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody that specifically binds the protein are identified by screening the hybridoma culture supernatants for such antibodies, e.g. using a standard ELISA assay.

Alternative to preparing monoclonal antibody-secreting hybridomas, a monoclonal antibody that binds to a protein can be identified and isolated by screening a recombinant combinatorial immunoglobulin library (e.g. an antibody phage display library) with the protein, or a peptide thereof, to thereby isolate immunoglobulin library members that bind specifically to the protein. Kits for generating and screening phage display libraries are commercially available (e.g. the Pharmacia Recombinant Phage Antibody System, Catalog No. 27-9400-01; and the Stratagene SurfZAP™ Phage Display Kit, Catalog No. 240612; each of which is incorporated herein by reference).

Examples of methods and compounds particularly amenable for use in generating and screening antibody display libraries can also be found in, for example, Ladner et al U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; Grifeths et al. (1993) EMBO J. 12:725-734; Hawkins et al. (1992) J Mol Biol 226:889-896; Clarkson et al. (1991) Nature 352:624-628; Gram et al. (1992) PNAS 89:3576-3580; Garrad et al. (1991) Bio/Technology 9:1373-1377; Hoogenboom et al. (1991) NucAcid Res 19:4133-4137; Barbas et al. (1991) PNAS 88:7978-7982; McCafferty et al. Nature (1990) 348: 552-554; each of which is incorporated herein by reference.

In another embodiment, ribosomal display can be used to replace bacteriophage as the display platform fro identifying antibodies for use in the methods of the invention (see, e.g. Hanes et al. 2000. Nat. Biotechnol. 18:1287; Wilson et al. 2001. Proc. Natl. Acad. Sci. USA 98:3750; Irving et al. 2001 J. Immunol. Methods 248:31; each of which is incorporated herein by reference). In yet another embodiment, cell surface libraries can be screened for antibodies (Boder et al. 2000. Proc. Natl. Acad. Sci. USA 97: 10701; Daugherty et al. 2000 J. Immunol. Methods 243:211; each of which is incorporated herein by reference). Such procedures provide alternatives to traditional hybridoma techniques for the isolation and subsequent cloning of monoclonal antibodies.

In another embodiment, an antibody that may be used in the methods of the invention is a substantially human antibody generated in transgenic animals (e.g., mice) that are incapable of endogenous immunoglobulin production (see e.g. U.S. Pat. Nos. 6,075,181, 5,939,598, 5,591,669 and 5,589,369 each of which is incorporated herein by reference).

For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies can also be isolated and manipulated as described herein.

Yet another highly efficient means for generating recombinant antibodies for use in the methods of the invention is disclosed by Newman, Biotechnology, 10:1455-1460 (1992); incorporated herein by reference. Specifically, this technique results in the generation of primatized antibodies that contain monkey variable domains and human constant sequences. This reference is incorporated by reference in its entirety herein. Moreover, this technique is also described in U.S. Pat. Nos. 5,658,570, 5,693,780 and 5,756,096; each of which is incorporated herein by reference.

Once a monoclonal antibody has been identified (e.g. either a hybridoma-derived monoclonal antibody or a recombinant antibody from a combinatorial library, including monoclonal antibodies that are already known in the art), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g. phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) Sequences of Proteins of Immunological Interest, Fifth Edition, U.S. Department of Health and Human Services, NIH Publication No. 91-3242 and in the "Vbase" human germline sequence database.

Once obtained, the antibody light and heavy chain sequences are cloned into a recombinant expression vector using standard methods. As discussed above, the sequences encoding the hydrophobic leaders of the light and heavy chains are removed and sequences encoding a nuclear localization signal (e.g. from SV40 Large T antigen) are linked in-frame to sequences encoding either the amino- or carboxy terminus of both the light and heavy chains. The expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly.

In another embodiment, an inhibitory agent for use in the methods of the invention is a peptidic compound derived from the amino acid sequence of a negative regulator of intracellular levels of glucose, pyruvate, lactate, and/or NADPH.

Peptidic compounds useful in the method of the invention can be made intracellularly in cells by introducing into the cells an expression vector encoding the peptide. Such expression vectors can be made by standard techniques using oligonucleotides that encode the amino acid sequence of the peptidic compound. The peptide can be expressed in intracellularly as a fusion with another protein or peptide (e.g. a GST fusion). Alternative to recombinant synthesis of the peptides in the cells, the peptides can be made by chemical synthesis using standard peptide synthesis techniques.

Synthesized peptides can then be introduced into cells by a variety of means known in the art for introducing peptides into cells (e.g. liposome and the like).

Another form of an inhibitory agent which inhibits a negative regulator of the generation and/or uptake of glucose, pyruvate, lactate, and/or NADPH in a cell is a chemical small molecule compound.

This invention is further illustrated by the following examples which should not be construed as limiting. The contents of all references, patents and published patent applications cited throughout this application, as well as the Figures, are hereby incorporated by reference.

EXAMPLES

Example 1

Assessing Stimulation of the Insulin/mTOR Pathway and Resulting Effects on Cone Cell Death in a Mouse Model of Retinitis Pigmentosa Material and Methods
Animals: Wild type (wt) mice (C57B1/6N) and PDE-β-/- mice (referred as rd1 or FVB/N) were purchased from Taconic Farms. The PDE-β-/- mice have a mutation in the β-subunit of cGMP *phosphodiesterase* (Bowes, C. et al. (1990) *Nature* 347, 677-80) (PDE). The PDE-γknock-out (PDE-γ-KO) lacks the γ-subunit of PDE (Tsang, S. H. et al. (1996) *Science* 272, 1026-9). The rhodopsin knock-out (Rho-KO) lacks the rod-specific opsin gene (Tsang, S. H. et al. (1996) *Science* 272, 1026-9; Lem, J. et al. (1999) *Proc Natl Acad Sci USA* 96, 736-41). The P23H mouse has a proline-23 to histidine mutation in the rhodopsin gene (Naash, M. I., et al. (1993) *Proc Natl Acad Sci USA* 90, 5499-503). As this mouse carries a transgene the strain was always crossed back to C57B1/6N to ensure that none of the progeny would carry two alleles of the transgene. The transgene is specifically expressed in rods (Gouras, P., et al. (1994) *Vis Neurosci* 11, 1227-31; Woodford, B. J., et al. (1994) *Exp Eye Res* 58, 631-5; al-Ubaidi, M. R. et al. (1990) *J Biol Chem* 265, 20563-9) and carries 3 mutations in the rhodopsin gene (Val-20 to Gly, Pro-23 to H is, Pro-27 to Leu). In this study it is referred as the P23H mutant. The cone-lacZ strain has been previously described (Wang, Y. et al. (1992) *Neuron* 9, 429-40). All procedures involving animals were in compliance with the ARVO Statement for the Use of Animals in Ophthalmic and Vision Research.

Figures 3A, 3O:
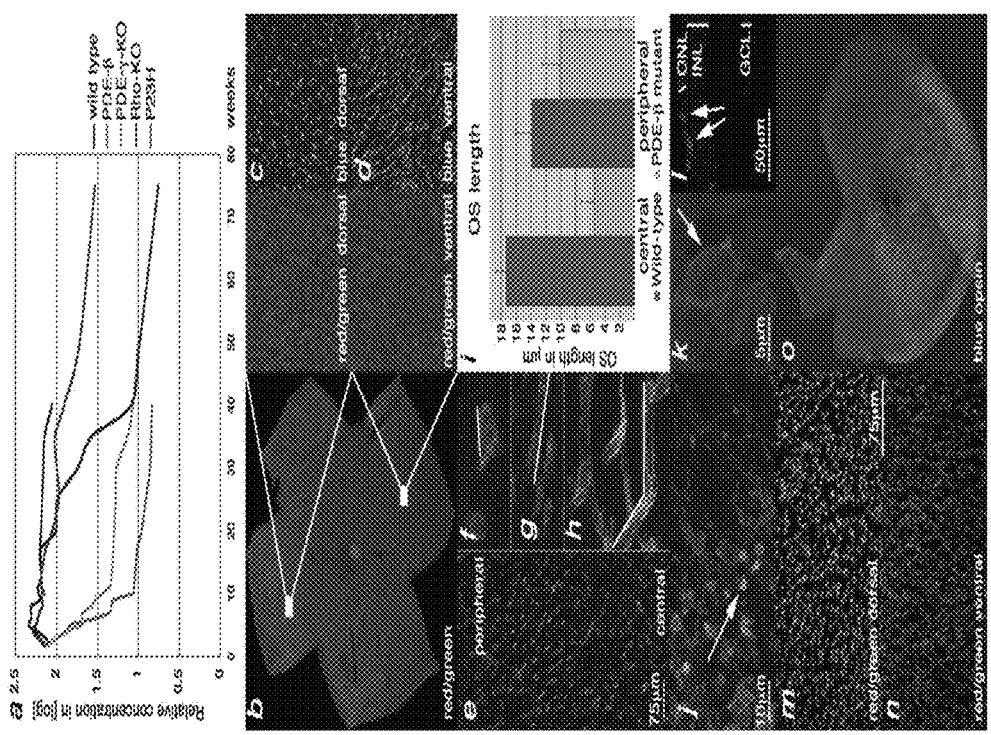
FIG. 3 depicts cone death kinetics described in Example 1 as follows: (a) qRT-PCR analysis for Opn1sw during cone degeneration. Changes are in indicated as the logarithm of the relative concentration over time on the Y-axis while X-axis indicates postnatal weeks. (b-h, j, k, m-o) Show retinal flat mounts. (k) Shows a retinal section. Medium gray shows PNA expression, light gray shows red/green opsin expression (b, j-n) or blue opsin expression (c, d, o). (b-d) Wild type retina at P35. Red/green opsin (b) and PNA (c, d) expression were detected dorsal and ventral while blue opsin (c, d) was detected only ventrally. (e-g, j-o) Analysis in the PDE-β mutant. (e-g) Central to peripheral gradient of PNA and shortening of cone outer segments (OS). At P20, prior to the major cone death phase, there were fewer elongated OS in the center (e) as compared to the periphery. (f) High magnification of a central or peripheral (g) OS from (e). (h) Wild type OS (white line in f-h marks the OS). (i) Quantification of OS length in central and peripheral regions. The data represents an average of 15 measurements on 3 different retinae of 3 week old mice. With the shortening of OSs during degeneration, red/green opsin was localized throughout the membrane of the cell body and PNA, which detects an extracellular protein(s), was reduced to a small dot attached to the residual OS (j) (arrow: shows red/green and PNA overlap). (k) High magnification of a cone showing red/green localization at the membrane of the main cell body (arrow). (l) Cross section showing red/green in cell body (arrows; j-l P70). Red/green opsin was detected mainly dorsal (l) during degeneration while PNA (m, n) or blue opsin (o) were not altered (m, n: P21, same scale bar; o: P49).
Figures 13A, 13B, 13C, 13D:
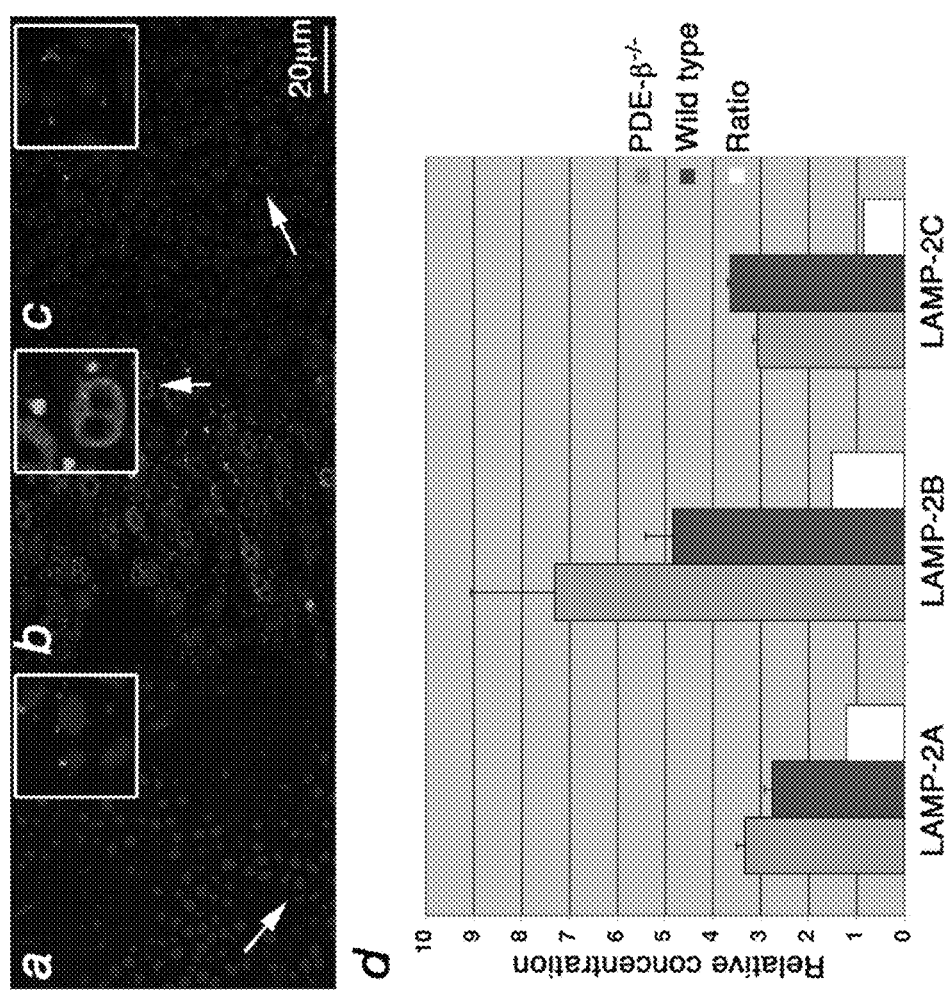
FIG. 13 depicts the increased levels of LAMP-2 at the lysosomal membrane as described in Example 1 as follows: (a-c) Immunofluorescence on retinal flat mounts where LAMP-2 is shown in light gray, red/green opsin in medium and dark gray shows nuclear DAPI stain. Insets in upper right corner (with box) show enlarged cells (arrow). (a) Wild type retinae at PW5 showing lysosome (small light gray dots) with normal LAMP-2 distribution. Weak red/green opsin signal is detected at the level of the PR nuclei since in wild type it is mainly found in the OSs. (b, c) PDE-β mutant at PW5. (b) Enlarged lysosomes (dots) due to accumulation of LAMP-2 at the lysosomal membrane are seen specifically in cones. (c) Confocal section of same field as in (b) taken at the level of the inner nuclear layer showing levels of LAMP-2 similar to those in wild type (a). (d) qRT-PCR for the 3 different LAMP-2 splice forms showing the relative concentration and the ratios between the PDE-β mutant and wild type.

Affymetrix array analysis: RNA was extracted as described previously (Punzo, C. & Cepko, C. (2007) *Ophthalmol Vis Sci* 48, 849-57). Three to 4 retinae were used per extraction. A minimum of two arrays were analyzed per time point. The statistical significance of each gene expression profile was determined by a Jonckheere-Terpstra test of the hypothesized cone-death patterned alternative, using exact p-values calculated by the Harding algorithm (Harding, E. F. (1984) *Applied Statistics* 33, 1-6).

qRT-PCR was performed as described previously with the same primers and conditions for Opn1sw and gapdh (Punzo, C. & Cepko, C. (2007) *Ophthalmol Vis Sci* 48, 849-57). The following primers and conditions were used for the three LAMP-2 splice forms: LAMP-2 forw. ctgaaggaagtgaatgtctacatg (SEQ ID NO:1); LAMP-2A rev. gctcatatccagtatgatggc (SEQ ID NO:2); LAMP-2B rev. cagagtctgatatccagcatag (SEQ ID NO:3); LAMP-2C rev. gacagactgataaccagtacg (SEQ ID NO:4). Conditions for all three PCRs: 95° for 3 sec, 52° for 15 sec, 72° for 25 sec. The data in FIG. 3a and FIG. 13d represent an average of 3 measurements corrected for gapdh.

Figures 10A, 10B:
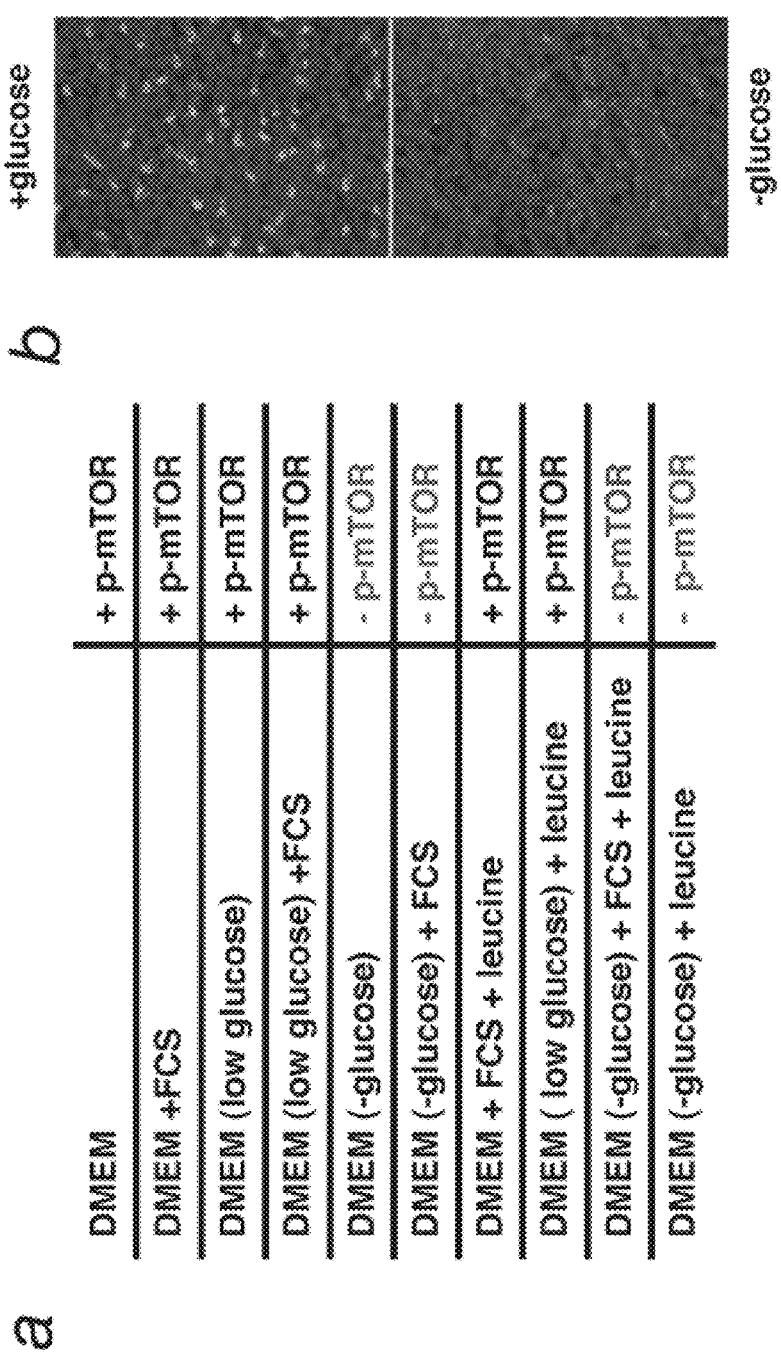
FIG. 10 depicts the dependence of p*-mTOR levels on the presence of glucose as described in Example 1. Different media conditions were tested (a) during 4 hours of retinal explant culture. After culture, retinae were fixed and stained for p*-mTOR (medium gray), PNA (light gray) and DAPI (dark gray). Retinal flat mounts were imaged (b). Dorsal p*-mTOR was only detected when glucose was present in the media.
Figures 11A, 11B, 11C, 11D, 11E, 11F, 11G, 11H, 11I, 11J:
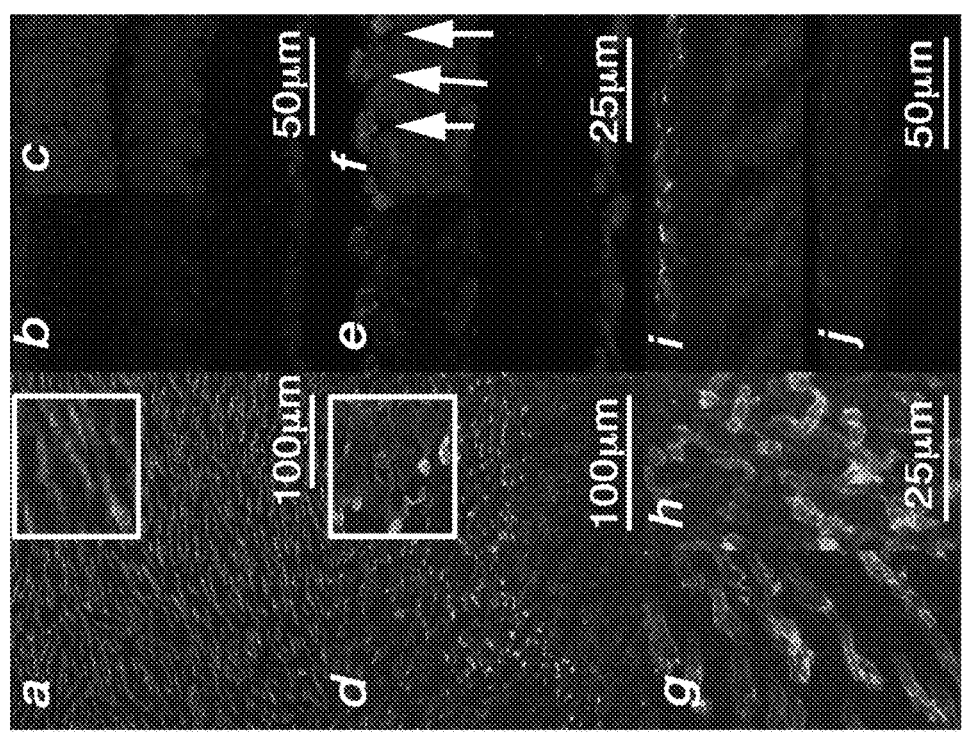
FIG. 11 depicts the upregulation of Hif-1α and GLUT1 in cones as described in Example 1. All panels show immunofluorescent staining. Left column (a, d, g, h,) shows retinal flat mounts and right column (b, c, e, f, i, j) retinal sections. Dark gray shows nuclear DAPI staining and light gray shows cones marked with PNA. (a-f) Staining for HIF-1α (medium gray). (a) Wild type (PW10) (inset) showing higher magnification. (b, c) Cross sections in wild type (PW10). (c) DAPI overlap of (b). (d-f) During cone degeneration in PDE-β-/- (PW10) increased levels of HIF-1α are found in cones (d, inset). (e, f) Cross sections show that the increase of Hif-1α occurs mainly in cones (arrows point to cones that at this stage are located within the top layer of the inner nuclear layer). (f) DAPI overlap of (e). (g) GLUT1 expression in wild type (PW10) (medium gray). Most of the signal in between the cones reflects expression in rods. (h j) Increased expression of GLUT1 in cones during degeneration seen in flat mounts (h) and sections (i j). (i) Overlap of (j) with PNA.
Figures 12A, 12B, 12C, 12D, 12E, 12F, 12G, 12H:
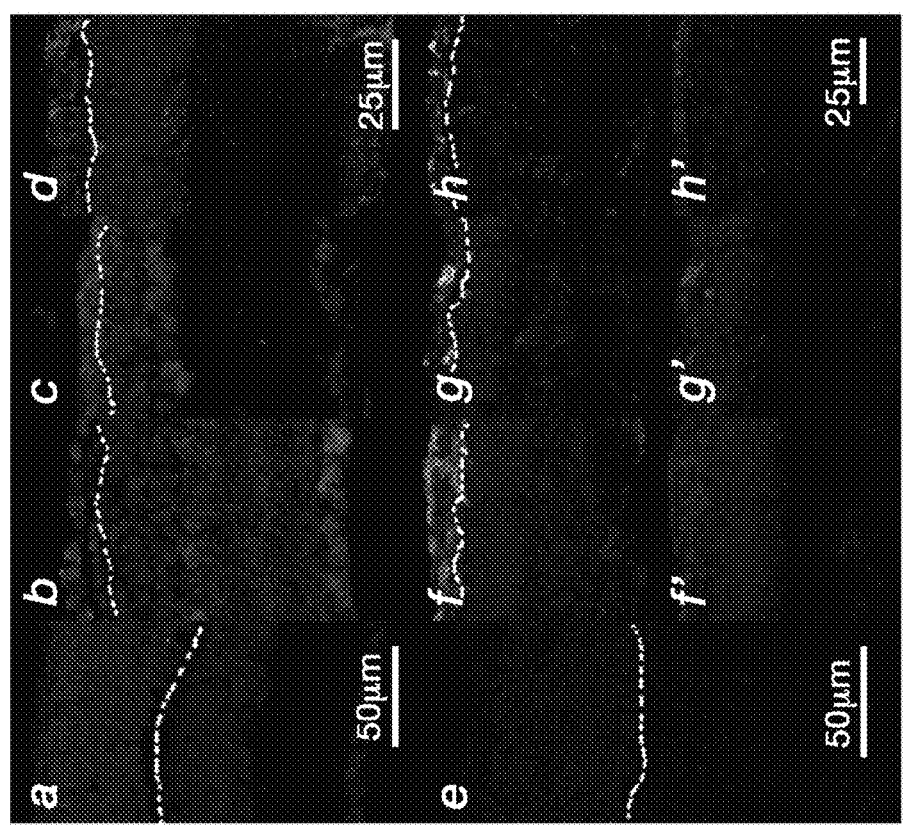
FIG. 12 depicts the upregulation of Hif-1α and GLUT1 in cones as described in Example 1 All panels show immunofluorescent signals within retinal sections. Dark gray shows nuclear DAPI staining and light gray shows cones marked with PNA. (a-d) Staining for HIF-1α (medium gray). (a) Wild-type at PW10 (see also FIG. 11a-c). (b) PDE-γ-KO at PW5. (c) Rho-KO at PW20. (d) P23H at PW70. (e-h) Staining for GLUT1 (medium gray). (e) Wild-type at PW10. (f) PDE-γ-KO at PW5 with PNA overlap. (f') Same image as (f) without PNA. (g) Rho-KO at PW20. (g') Same image as (g) without PNA. (h) P23H at PW70. (h') Same image as (h) without PNA. White dotted line marks border between the ONL and INL.

Retinal explant cultures: The retina was dissected free from other ocular tissues in DMEM, and then incubated in conditions according to the chart in FIG. 10a. Regular DMEM was at 4.5 g/L glucose, low glucose was at 1 g/L, leucine was added at 200 μM and FCS at 10%. Incubation was performed for 4 h and the retinae were fixed and processed for antibody staining as described below.

Figures 16A, 16B, 16C, 16D, 16E, 16F:
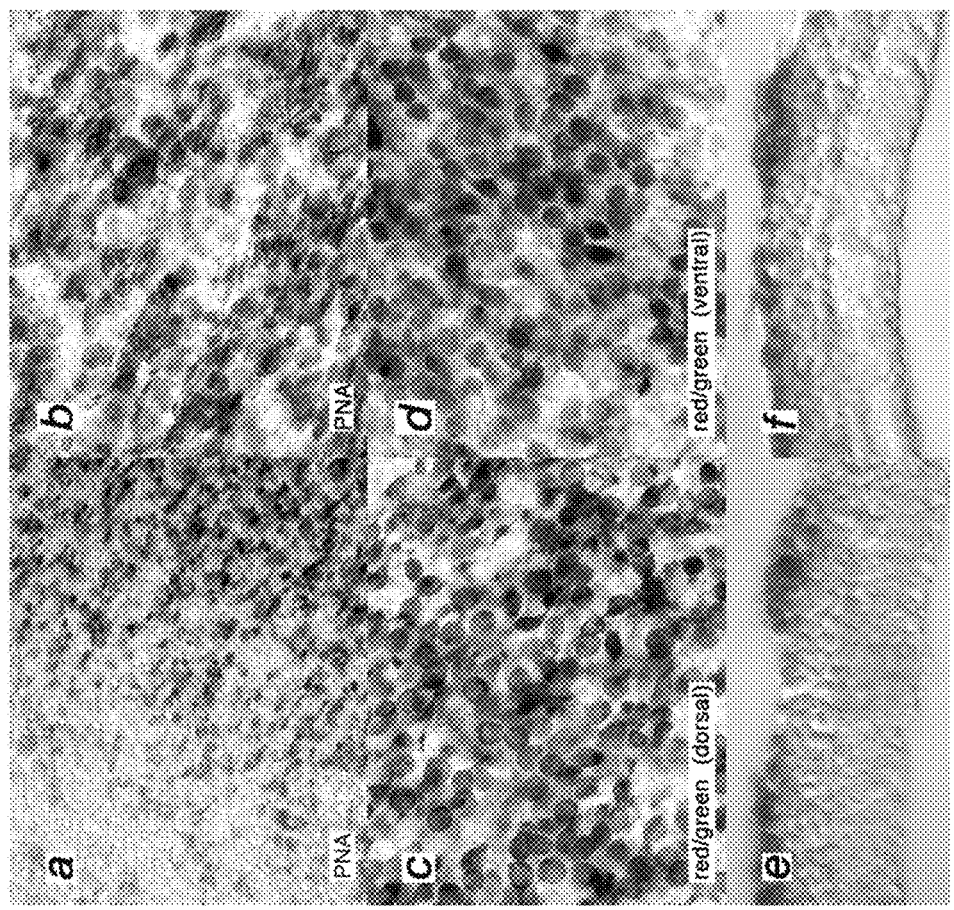
FIG. 16 depicts the cone-lacZ transgene in the PDE-β mutant at 7 weeks of age as described in Example 1 as follows: (a, b) Double labeling of cones with PNA (dark gray) and lacZ staining medium gray). More cones were labeled by lacZ than by PNA. Since PNA marks an extracellular matrix protein of the OS, once the OSs were reduced, PNA became a less reliable marker. (c, d) Double labeling of cones by α-red/green opsin (dark gray) and lacZ staining (X-gal; medium gray) in the dorsal (c) and ventral (d) retina. Red/green opsin levels decreased ventrally during degeneration which made this marker not suitable for detection of cones across the retina. (e, f) Sections of retina stained for lacZ showing the signal in cones on top of the INL.

TUNEL, X-gal histochemistry and In Situ Hybridizations were performed as described previously (Punzo, C. & Cepko, C. (2007) *Ophthalmol Vis Sci* 48, 849-57). For the double labeling of cones (see FIG. 16), retinae were first fixed in 2% PFA for 15 min. then processed for the X-GAL reaction and then post fixed in 4% PFA for 15 min. A biotin-PNA was used in an antibody staining procedure (see below) and detected with Streptavidin-POD (1:500, Roche) by a DAB stain (Sigma) according to the manufacture's instructions. The following ESTs were used for the red/green opsin and blue opsin probes respectively: red/green opsin (BE950633); blue opsin (BI202577). Probe for rhodopsin was generated by sub-cloning the coding sequence of the gene into pGEM-T Easy (Promega). The following primers were used for amplification of the coding sequence: forw. agccatgaacggcacagaggg (SEQ ID NO:5); rev. cttaggctggagccacctggct (SEQ ID NO:6). The antisense RNA was generated with T7 RNA polymerase.

Viral injections were performed as described previously (Punzo, C. & Cepko, C. L. (2008) *Dev Dyn* 237, 1034-42). Mice were injected at embryonic day 10 and harvested at postnatal week 10. The fusion protein was generated with a NotI site at the 5' end followed by GFP, then LC3, and then an XhoI site at the 3' end and cloned into pQCXIX (Clonetech: cat. #631515). The following primers were used for the fusion protein: 5'NotI-GFP atgcgggccgccaccatggtgagcaagggcgaggagc (SEQ ID NO:7), 3'GFP-LC3 aggtcttctcggacggcatcttgtacagctcgtccatgc-cgag (SEQ ID NO:8), 5'LC3 atgccgtccgagaagaccttcaagc (SEQ ID NO:9), 3'LC3-XhoI atctcgagttacacagccattgctgtcccgaatg (SEQ ID NO:10).

Rapamycin, Streptozotocin and Insulin treatments were performed as follows. Rapamycin was diluted to 10 mg/ml in ethanol. The stock was diluted to 0.015 mg/ml in drinking water over a period of 2 weeks. A single intraperitoneal injection of 150 μl (12 mg/ml in 0.1M citric acid, ph4.5) of Streptozotocin was injected at postnatal day (P) 21. Insulin was injected intraperitoneally daily starting at P21. The concentration was increased weekly such that the first week, 10 U/kg body weight, the second 15 U/kg, the third 20 U/kg and fourth 30 U/kg body weight, were injected. In the treatment that lasted 7 weeks 30 U/kg body weight were injected for the remaining 3 weeks. Blood glucose levels were measured by collecting a drop of blood from the tail directly onto a test strip from TrueTrack smart system (CVS pharmacy). Eye bleeds were avoided due to the fact that cell survival in the retina was being assayed.

Quantification of cone survival was performed as follows. The colors of the bright light image were inverted and processed with Imaris software (Bitplane Inc) to calculate the percentage of blue surface area versus the total retinal surface area (see also FIG. 17). A minimum of 8 retinae per treatment, and for the control, were analyzed. P-values were calculated by the student's t-test. The cone lacZ transgene was chosen over PNA as a cone marker since the transgene labels cones more persistently, since, due to the shortening of the cone OS, PNA was found to stain less reliably than lacZ (see FIG. 16).

Whole mount and section antibody staining were performed as previously (Punzo, C. & Cepko, C. L. (2008) *Dev Dyn* 237, 1034-42) described with the following modifications. Antibody staining for LAMP-2: Triton was replaced with 0.01% Saponin. Antibody staining for p*-mTOR and p*-S6: PBS was replaced by TBS in every step of the procedure. Primary antibody dilutions: mouse α-rhodopsin Rho4D21:20051; goat α-β-Galactosidase (Serotec) 1:400; rabbit α-blue opsin (Jeremy Nathans) 1:1000; rabbit α-Gnat1 1:200 (Santa Cruz); rabbit α-Cleaved Caspase-3 (Cell Signaling) 1:100; rabbit α-Cleaved Lamin A (Cell Signaling) 1:100; rabbit α-GLUT-1 (Alpha Diagnostics) 1:100; rabbit α-p*-mTOR (Ser2448) (Cell Signaling) 1:300; rabbit α-p*-S6 (Ser235/236) (Cell Signaling) 1:100; rabbit α-HIF-1α (R&D Systems) 1:300; rat α-LAMP-2 (clone: GL2A7, from DSHB) 1:200. Time points analyzed for the rod and cone death kinetics (P: postnatal day; PW: postnatal week): PDE-β-/-: P10-P20 daily, PW3-10 weekly, PW 12, PW15, PW18, PW45; PDE-γ-KO: P10-P20 daily, PW3-PW10 weekly, PW15, PW25, PW45; Rho-KO: PW4-PW8 weekly, PW10, PW11, PW17, PW20, PW25, PW27, PW31, PW34, PW37, PW45, PW55, PW80; P23H: PW5, PW10, PW16, PW25, PW30, PW35, PW40, PW65, PW70, PW75, PW80, PW85.

Results

Rod and Cone Death Kinetics

Figures 1A, 1Q:
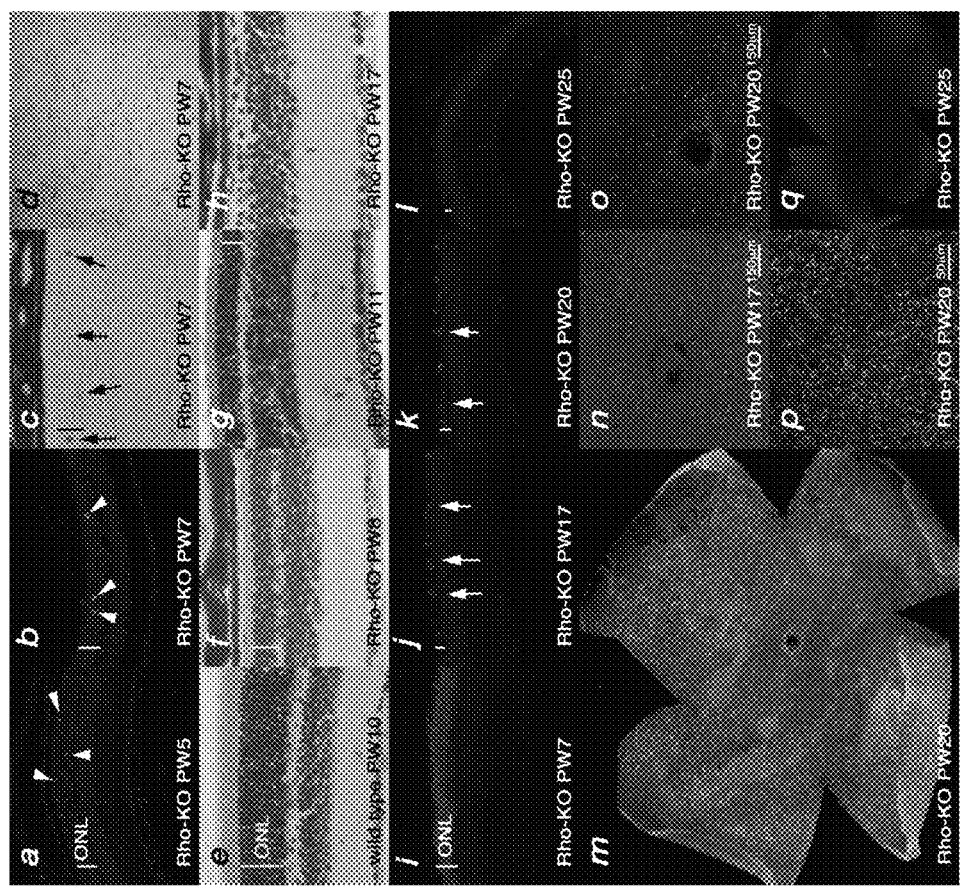
FIG. 1 depicts rod death kinetics in the Rho-KO mutant described in Example 1 as follows: (a-d) Onset of rod death seen by cleaved nuclear envelope protein LaminA (a), Cleaved Caspase3 (b) (arrowheads) as well as TUNEL (c, d) (arrows: dark gray) (light gray in a, b shows nuclear DAPI staining). (d) Shows a retinal flat mount with view onto the photoreceptor layer. (e-h) Progression of rod death determined by the reduction of the ONL as seen by HE staining. (i-q) End phase of rod death assessed by section analysis (i-l) or by retinal flat mounts (m-q). In the Rho-KO the onset of rod death is around PW5 (a) and progresses up to PW25 (l). By PW17 the ONL is reduced to one row of cells (h, j) and in the following 8 weeks the remaining rods die (j-q) as seen by immunofluorescence with an antibody directed against guanine nucleotide protein alpha transducin (Gnat1) on sections of progressively older animals (j-l). (m-q) Retinal flat mounts showing rods visualized by immunofluorescence with an antibody directed against Gnat1. (m) Shows entire retina while (m, o) show higher magnification around the optic nerve head and (p) shows peripheral region. (q) Shows no signal at PW25 where on sections rods were also not detected (l). Age (in postnatal weeks (PW)) is indicated in the panels. Vertical bar in (a-c, e-l) indicates thickness of the ONL.
Figures 2A, 2Q:
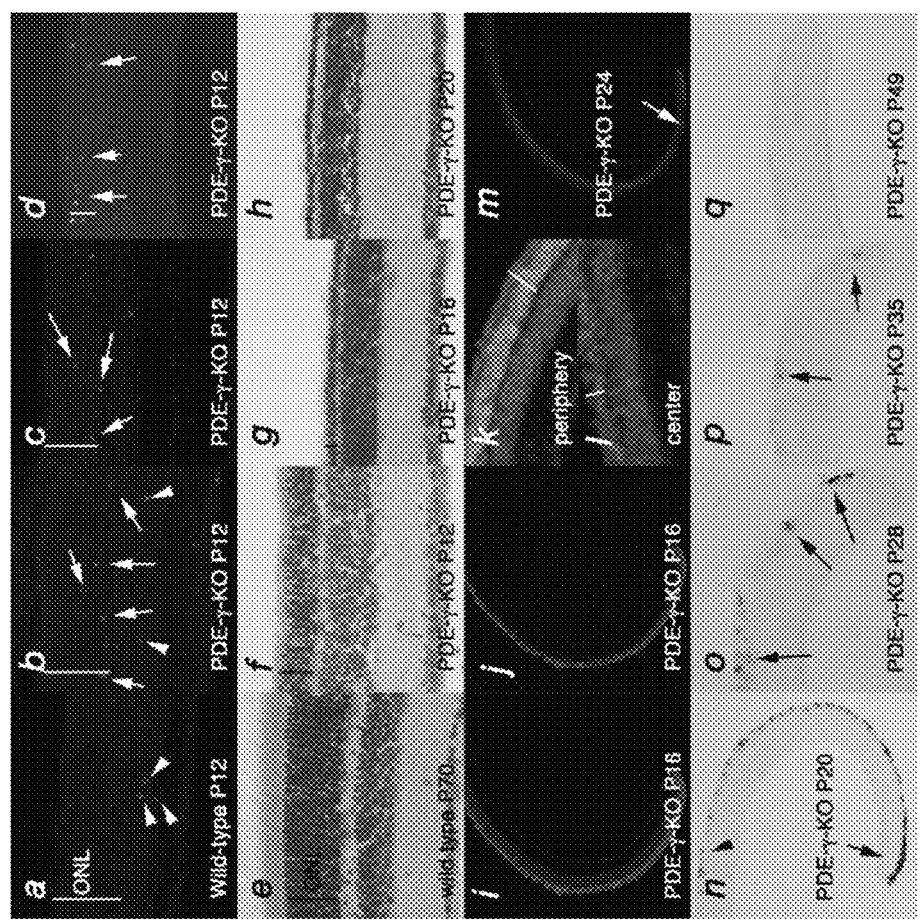
FIG. 2 depicts rod death kinetics in the PDE-γ-KO described in Example 1 as follows: (a-d) Onset of rod death seen by cleaved caspase 3 (a, b). At P12, misplaced and excess cells in the INL were dying as part of developmental cell death, as seen in a wild-type control (a) (arrowheads) while in the mutant, cells started to die in the ONL, where photoreceptors reside (b) (arrows). The onset of rod death was also seen by immunofluorescence for the cleaved nuclear envelope protein, LaminA (c) (arrows) as well as TUNEL (d) (arrows; light gray in a-d shows nuclear DAPI staining). Progression of rod death was determined by the reduction of the thickness of the ONL, as seen by HE staining (e-h). (i-q) End phase of rod death was assessed by analysis of sections of progressively older animals. (i-m) Rods were visualized by immunofluorescence with α-rhodopsin or by in situ hybridization for rhodopsin (n-q). (i, j) Retinal section at P16 showing peripheral to central region. (i) Same picture as in (j) with nuclear DAPI stain. (k, l) Higher magnification of section in (i) showing peripheral (k) and central (l) region. As rods die in a central to peripheral manner, more rods were present in the periphery than in the center. By P20, the ONL was reduced to 1 row of cells and rods were found mainly in the periphery (compare arrow (periphery) in (n) to arrowhead (central). The remaining rods in the PDE-γ-KO died over 4 weeks (n-q) as seen on sections. By P49 (q) all rods had died in this mutant (o-q: periphery). Age (in postnatal days (P)) is indicated in the panels. Vertical bar in (a-h, k, l) indicates thickness of the ONL. Data for PDE-β-/- are not shown as they are comparable to the PDE-γ-KO and data on the rod death kinetics of this mutant have been presented in an earlier publication (IOVS, 2007, 48 (2): 849-857).
Figures 4A, 4B, 4C, 4D, 4E, 4F, 4G:
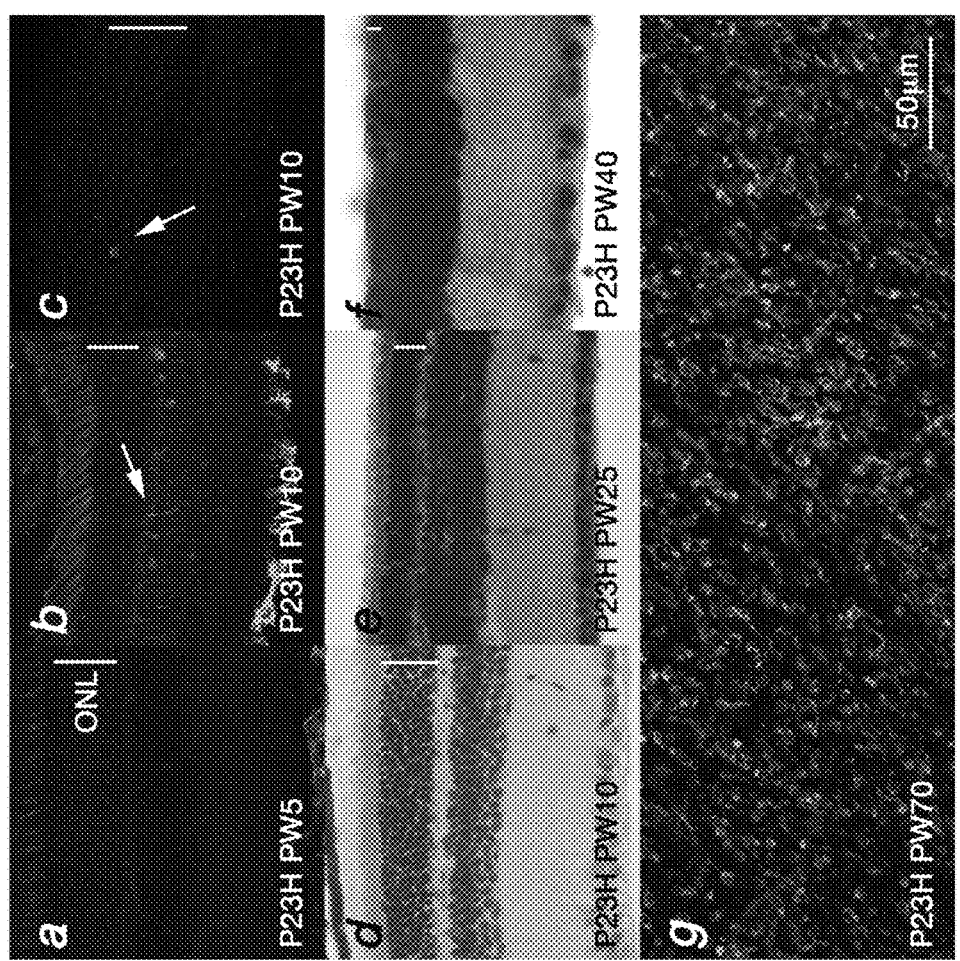
FIG. 4 depicts rod death kinetics in the P23H mutant described in Example 1 as follows. (a-c) Onset of rod death. As rod death progressed very slowly in this mutant, the upregulation of glial fibrillary acidic protein (GFAP) in Muller glia, which has been described as a hallmark of retinal degeneration, was used in conjunction with the other markers to determine the onset of rod degeneration. As seen by antibody staining against GFAP (a, b) degeneration started around PW10 (b). At PW5, GFAP was only found in the ganglion cell layer where it is normally expressed in astrocytes. Consistent with the upregulation of GFAP at PW10, cells positive for cleaved nuclear envelope protein LaminA (c) were also detected (arrow). However, few cells were seen per section due to the slow progression of rod death. (d-f) Progression of rod death determined by the reduction of the ONL as seen by HE staining. (g) End phase of rod death assessed by immunofluorescence with anti-rhodopsin. Although the ONL was reduced to one row of cells by PW35, no end point of rod death was determined. Rods continued to die slowly and even by PW70, many rods were still present (g). Interestingly, most of the rods at that age were confined to the ventral regions of the retina (see also FIG. 6). Age (in postnatal weeks (PW)) is indicated in the panels. Vertical bar in (a-f) indicates thickness of the ONL.
Figures 6A, 6B, 6C, 6D, 6E, 6F, 6G:
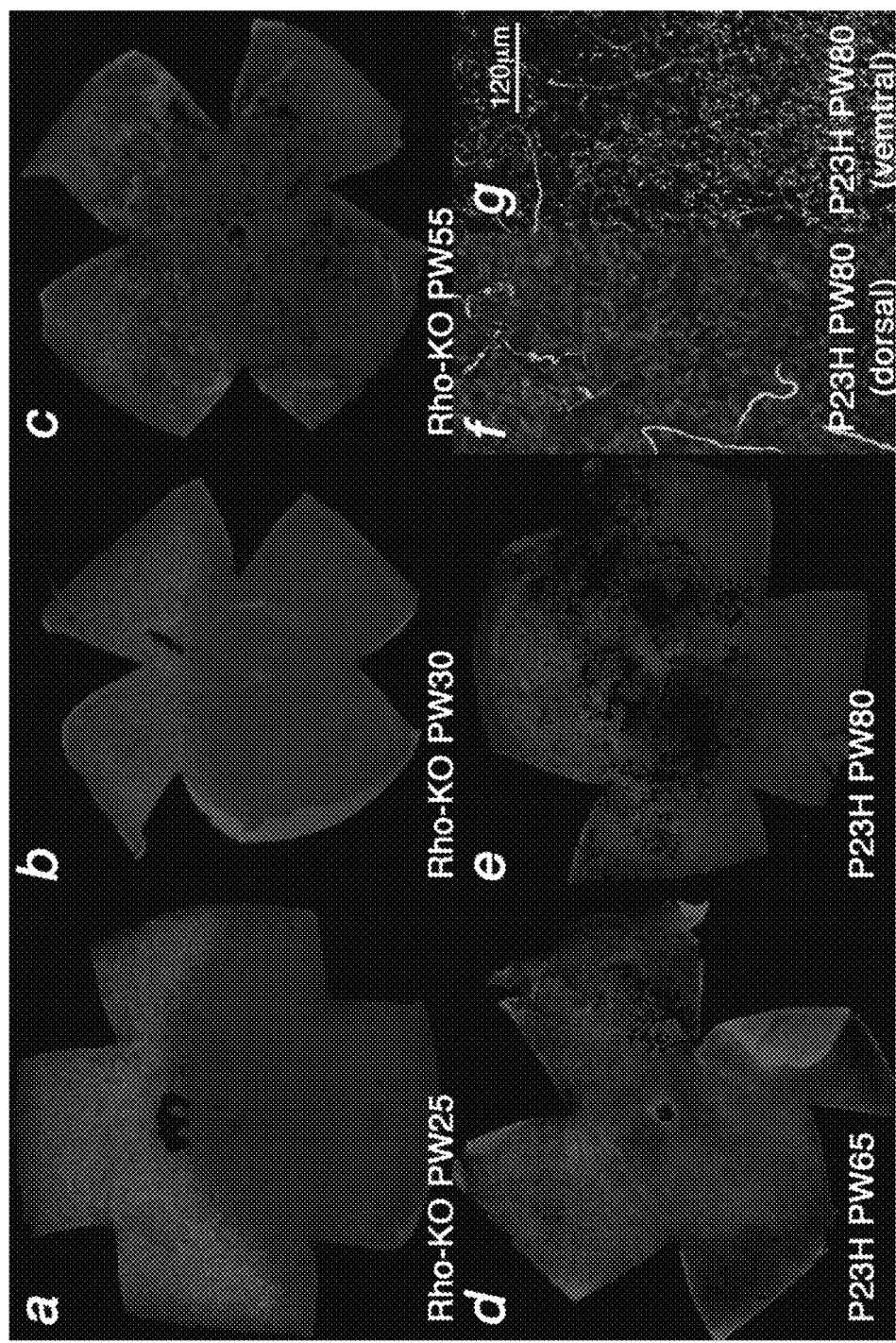
FIG. 6 depicts dorsal cone death kinetics seen by the immunofluorescence with anti-red/green opsin as described in Example 1 as follows: (a-c) Loss of dorsal cones in the Rho-KO mutant over time as seen by the reduced expression of red-green opsin. (d, e) Loss of dorsal cones in the P23H mutant over time. (f, g) Higher magnification of a double staining with an antibody against red/green opsin (medium gray) and rhodopsin (light gray) showing that most rods that survived up to PW80 were in the ventral regions (g) of the retina whereas the red/green expressing cones were mostly dorsal (f).

To establish a framework for comparing gene expression in 4 different models of RP, the equivalent stages of disease pathology were established through examination of the kinetics of rod (FIG. 1) (see also FIGS. 2 and 4) and cone (FIG. 3) (see also FIG. 6) death. Rod death kinetics were established by determining the onset, progression and end phase of rod death (FIG. 1). The time from the onset of rod death to the time when the outer nuclear layer (ONL) was reduced to 1 row of cells will be referred to as the major rod death phase. The time thereafter until rod death was complete will be referred to as the end phase of rod death. To determine the beginning of the major phase of rod death, cleavage of the nuclear envelope protein LaminA (FIG. 1a), and of the apoptotic protease Caspase3 (FIG. 1b), as well as TUNEL (FIG. 1c, d) were used. The continuation of the major rod death phase was monitored by these assays, as well as inspection of histological sections (FIG. 1e-h), as rods account for more than 95% of all PRs. Once the ONL reached one row of cells, the major phase of rod death was over. The end phase of rod death was determined using rod-specific markers to perform either in situ hybridization (see FIG. 2) or immunohistochemistry (FIG. 1i-l) on retinal sections. However, unless every section of a single retina is collected it is difficult to determine if any rods remain. Thus, retinal flat mounts also were used to allow a comprehensive analysis of the end phase of rod death (FIG. 1m-q). Interestingly, while in the two PDE mutants and in the Rho-KO mutant the end phase of rod death was clearly defined, in the P23H mutant, rods died so slowly that even 50 weeks (latest time point analyzed) after the end of the major phase of rod death, some rods were still present (see FIG. 4).

Two methods were used to determine the onset and progression of cone death. First, the overall time frame of cone demise was determined by quantitative real-time polymerase chain reaction (qRT-PCR) (FIG. 3a) for the ventral (Applebury, M. L. et al. (2000) *Neuron* 27, 513-23) cone specific transcript Opn1sw (opsin1 short-wave-sensitive: blue cone opsin). This allowed for an initial quantitative comparison among different strains, but was not adequate to determine the number of cones as transcript levels could vary prior to cell death. Next, whole mount immunohistochemistry for red/green opsin (Opn1mw: opsin1 medium-wave-sensitive) and peanut agglutinin lectin (PNA) were used (FIG. 3b-n). Both markers are expressed throughout the murine retina allowing for the visualization of cones (FIG. 3b-d). Interestingly, the onset of cone death always occurred at the equivalent stage of rod death, namely after the major rod death phase, when the thickness of the ONL was reduced to only a single row of cells. Cone death was found to proceed from the center to the periphery in all 4 models, as seen by staining with PNA (FIG. 3e). It was preceded by a gradual reduction of the outer segment (OS) length (FIG. 3f-i) and by opsin localization from the OS to the entire cell membrane (FIG. 3j-l). In addition, red/green opsin (Opn1mw) protein, which is normally detected throughout the mouse retina (FIG. 3b), was detected mainly dorsally during cone degeneration (FIG. 3m, n). However, PNA staining showed no appreciable difference across the dorsal/ventral axis (FIG. 3m, n). Similarly, blue opsin expression, which is normally detected only ventrally (Applebury, M. L. et al. (2000) *Neuron* 27, 513-23) (FIG. 3c, d), was not affected during degeneration (FIG. 3o). Shortening of cone OSs and loss of cone-specific markers has also been described in human cases of RP (John, S. K., et al. (2000) *Mol Vis* 6, 204-15).

Figures 5A, 5B, 5C:
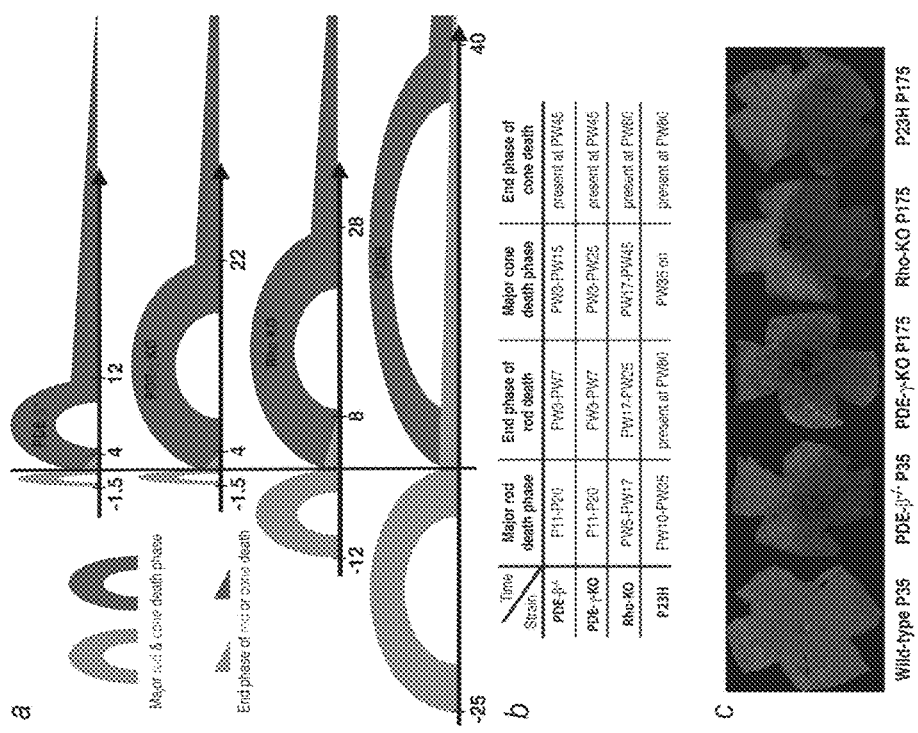
FIGS. 5A-5C depict the kinetics and histological changes that accompany rod and cone death across the 4 animal models of RP.

In summary, the kinetics and histological changes that accompanied rod and cone death shared several features across the 4 models. First, cone degeneration always started after the major rod death phase (FIG. 5a, b). This point was reached at very different ages in three of the 4 mutants, as the overall kinetics of rod death were quite different. Second, cone death was always central to peripheral and was preceded by a reduction in OS length. Third, in all 4 mutants, red/green opsin protein levels were detectable mainly dorsally during cone degeneration (FIG. 5c). These common features evidence a common mechanism(s) of cone death. Moreover, gene expression changes that were common across the 4 models at the onset of cone death serve to elucidate this common mechanism.

Microarray Analysis

Figures 7A, 7B, 7C:
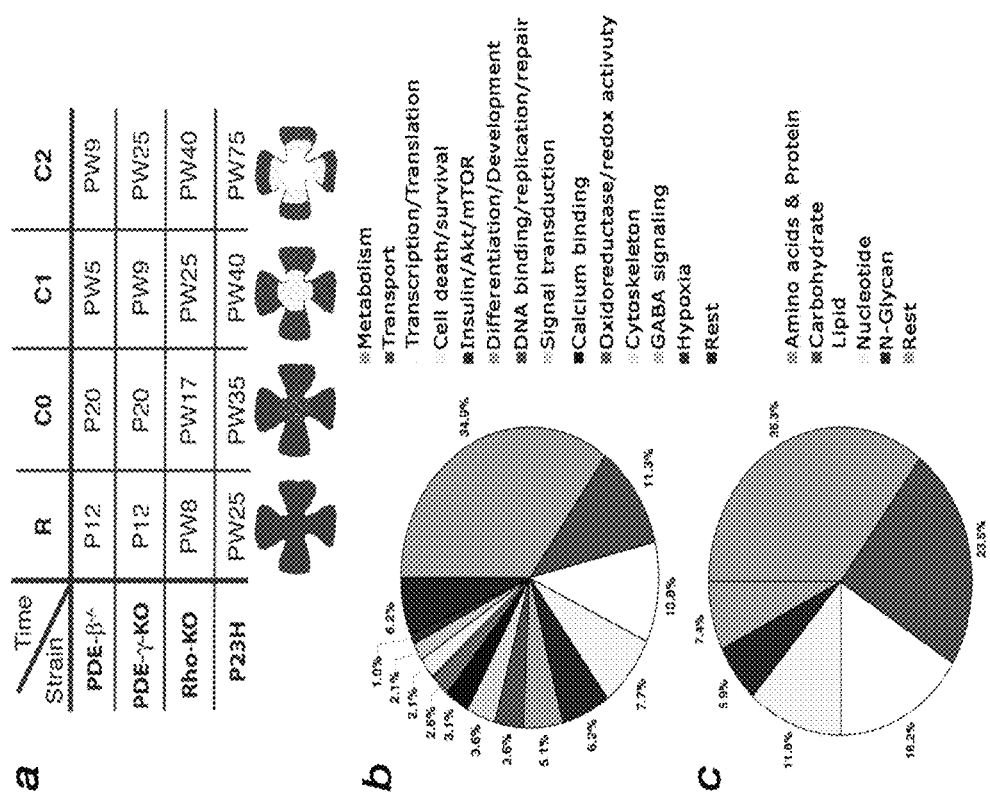
FIG. 7 depicts affymetrix microarray analysis as described in Example 1 as follows: (a) Equivalent time points in the 4 different mutants at which the microarray analysis was performed (R: approximately halfway through the major phase of rod death; C0: onset of cone death; C1 & C2 first and second time point during cone death respectively). Time is indicated in postnatal days (P) or postnatal weeks (PW). Cartoons depicting the progression of cone death are shown below the corresponding time points. (b) Distribution in percentage of the 195 genes that were annotated. (c) Distribution in percentage of the 68 genes (34.9%) that are part of metabolism in (b).

To determine common gene expression changes, RNA samples from all 4 models were collected halfway through the major phase of rod death, at the onset of cone death, and from two time points during the cone death phase (FIG. 7a). The RNA was then hybridized to an Affymetrix 430 2.0 mouse array. Gene expression changes were compared within the same strain across the 4 time points. Two criteria had to be fulfilled to select a gene for cross comparison among the 4 strains. First, the change over time had to be statistically significant (see Material & Methods). Second, a gene had to be upregulated at least 2 fold at the onset of cone death compared to the other three time points. This second criterion removed rod-specific changes that were still occurring at the onset of cone death while at the same time enriched for changes at the onset of cone death. A total of 240 Affymetrix IDs were found that satisfied both criteria within each of the 4 strains. The 240 IDs matched to 230 genes (see FIGS. 19A-E). Of the 195 genes that could be annotated, 34.9% (68 genes) were genes involved in cellular metabolism (FIG. 7b, c). The signaling pathway with the highest number of hits (12 genes) was the insulin/mTOR (mammalian target of rapamycin) signaling pathway (FIG. 7b), a key pathway in regulating many aspects of cellular metabolism. Thus, the data evidences that events at the onset of cone death coincided with changes in cellular metabolism likely to be regulated by the insulin/mTOR pathway.

mTOR in Wild Type and Degenerating Retinae

Figure 8:
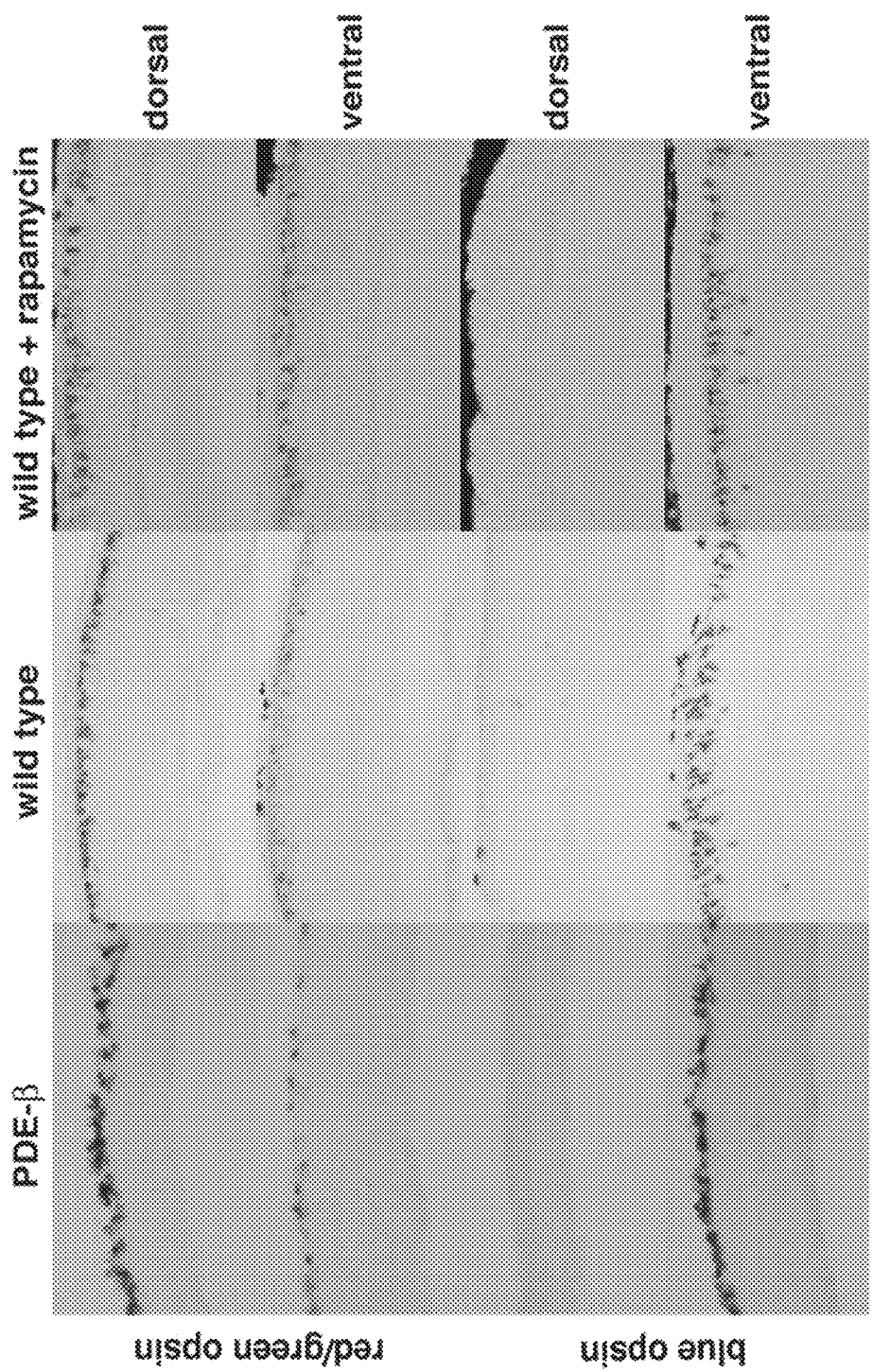
FIG. 8 depicts that red/green and blue opsin expression was not affected on the RNA level as described in Example 1 as follows: In situ hybridization for red/green opsin (first two rows) or blue opsin (third and fourth row) on retinal sections. RNA levels for red/green opsin and blue were comparable between ventral regions of mutant (first column), wild type animals treated with rapamycin (last column) or untreated wild type animals (second column).
Figures 9A, 9B, 9C, 9D, 9E, 9F, 9G, 9H, 9I, 9J, 9K, 9L, 9M:
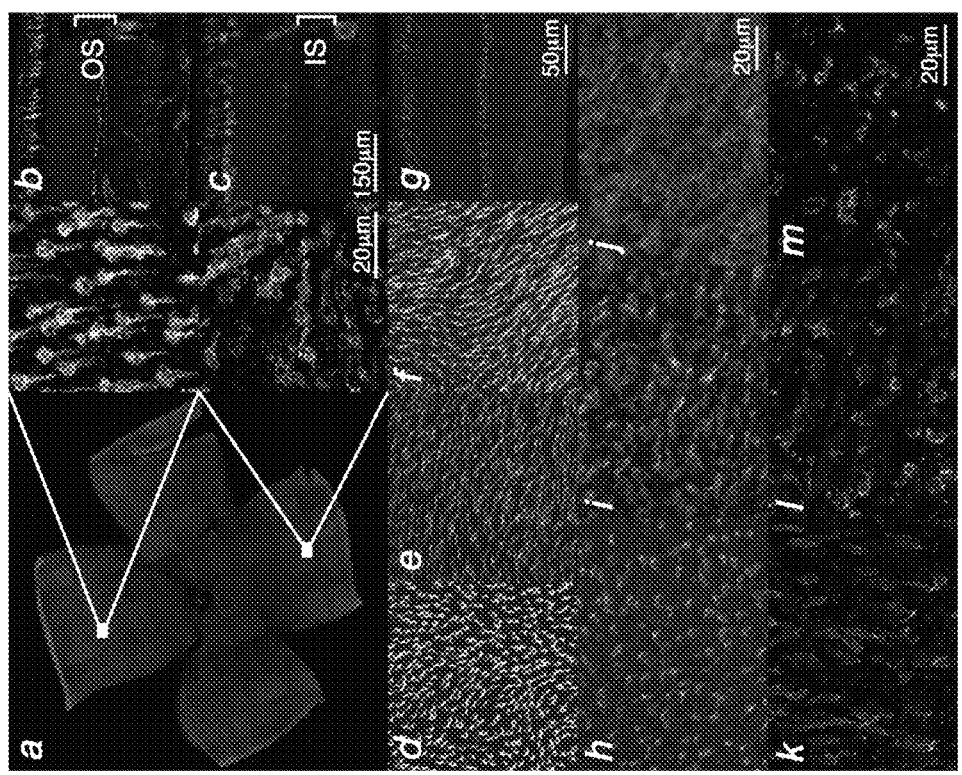
FIG. 9 depicts p*-mTOR in wild type and degenerating retinae as described in Example 1. All panels show immunofluorescence on retinal flat mounts (photoreceptor side up) with the exception of (b, c, g) which show retinal sections. Dark gray the nuclear DAPI stain. (a-c) p*-mTOR levels in wild type retinae. (a) Dorsal (up) enrichment of p*-mTOR. Higher magnification of dorsal and ventral region is shown to the right showing p*-mTOR in red and cone segments in green as detected by PNA. (b, c) Dorsal retinal sections stained for p*-mTOR (medium gray) and PNA (b) (light gray) or α-β-galactosidase (c) (lightest gray). The β-galactosidase is under the control of the human red/green opsin promoter and is expressed in all cones[48] (see Material & Methods). The insets in (b, c) show higher magnification of the cone segments indicating that the p*-mTOR signal is located in the lower part of the outer segment (OS; IS: inner segment). (d-g) Rapamycin treatment of wild type mice leads to downregulation of red/green opsin ventrally (e) but not dorsally (d) (medium gray). Ventral blue opsin (f) (medium gray) remains unaffected, as does PNA (d-g) (light gray). Rapamycin treatment does also not affect mTOR phosphorylation in wild type (g) (medium gray). (h-m) Reduced levels of dorsal p*-mTOR during photoreceptor degeneration (red signal). (h) Wild type control. (i, j) PDE-β mutant. The reduction starts during rod death at P15 (i) as the OSs (light gray: PNA) start to detach from the retinal pigmented epithelium. (j) By P30 only few cones medium gray: α-β-galactosidase) show high levels of p*-mTOR (dark gray). (k-l) A similar reduction is seen in dorsal cones of the other three mutants (cones marked in light gray by PNA). (k) PDE-γ-KO P35. (l) Rho-KO PW20. (m) P23H PW70.

Based on the findings of the microarray analysis, the insulin/mTOR signaling pathway was examined during the period of cone death. The kinase, mTOR, is a key regulator of protein synthesis and ribosome biogenesis (Reiling, J. H. & Sabatini, D. M. (2006) *Oncogene* 25, 6373-83). When cellular energy levels are high, mTOR allows energy consuming processes, such as translation, and prevents autophagy, while nutrient poor conditions have the reverse effect. Therefore, glucose, which increases cellular ATP levels, and amino acid availability, especially that of leucine, positively affect mTOR activity. To understand if cellular energy levels or amino acid availability might be compromised in cones during degeneration, levels of phosphorylated mTOR (p*-mTOR) were examined by immunofluorescence. Phosphorylation of mTOR increases kinase activity, and therefore levels of p*-mTOR can serve as an indicator of its activity level. Since every eukaryotic cell expresses mTOR, a certain level of p*-mTOR is likely to be found in every cell. Surprisingly, high levels of p*-mTOR were detected only in dorsal cones of wild type retinae (FIG. 9a-c). This phosphorylation pattern was reminiscent of the red/green opsin pattern seen during cone degeneration (FIG. 5c). Since mTOR is a key regulator of translation, we investigated whether the ventral red/green opsin downregulation that occurred during cone degeneration could be mimicked by a reduction in mTOR activity. To this end, wild type mice were treated with rapamycin, an mTOR inhibitor18. This treatment resulted in ventral downregulation of red/green opsin, without affecting blue opsin or PNA staining or the dorsal phosphorylation of mTOR itself (FIG. 9d-g). Thus, inhibition of mTOR in wild type recapitulated the expression of red/green opsin and blue opsin, as well as the pattern of PNA staining, in the mutants during degeneration, indicating that the ventral downregulation of red/green opsin seen during degeneration might be due to reduced mTOR activity. As expected for mTOR function, the downregulation of red/green opsin did not occur at the RNA level, but at the protein level, in untreated mutant mice, as well as in wild type mice treated with rapamycin (see FIG. 8). Finally, analysis of mutant retinae showed a decrease of p*-mTOR levels in dorsal cones during cone degeneration (FIG. 9h-m). To test whether the high level of p*-mTOR found in dorsal wild type cones was glucose-dependent, retinal explants of wild type mice were cultured in media for 4 hours in the presence or absence of glucose. Dorsal p*-mTOR was abolished in the absence of glucose even when leucine concentrations were increased in the medium (see FIG. 10). Thus, the data on mTOR establish a link between mTOR activity, the expression changes of red/green opsin seen during degeneration, and the microarray data, which indicated metabolic changes at the onset of cone death. Those changes may be caused by compromised glucose uptake in cones.

Responses of Cones to Nutritional Imbalance

The data on mTOR evidenced a nutritional imbalance in cones during cone degeneration, possibly caused by reduced glucose levels in cones. To test this idea, the level of the heterodimeric transcription factor, Hypoxia inducible factor 1 (HIF-1α/β), which improves glycolysis under stress conditions such as low oxygen, was examined. HIF-1 and mTOR are tightly linked as low oxygen results in low energy due to reduced oxidative phosphorylation, and therefore in reduced mTOR activity (Reiling, J. H. & Sabatini, D. M. (2006) *Oncogene* 25, 6373-83; Dekanty, A., et al. (2005) *J Cell Sci* 118, 5431-41; Hudson, C. C. et al. (2002) *Mol Cell Biol* 22, 7004-14; Treins, C., et al. (2002) *J Biol Chem* 277, 27975-81; Zhong, H. et al. (2000) *Cancer Res* 60, 1541-5; Thomas, G. V. et al. (2006) *Nat Med* 12, 122-7). An upregulation of the regulated subunit HIF-1α would likely reflect low glucose levels in cones, and not hypoxic conditions, as oxygen levels are increased due to the loss of rods (Yu, D. Y. & Cringle, S. J. (2005) *Exp Eye Res* 80, 745-51). Immunofluorescence analysis of HIF-1α during cone degeneration revealed an upregulation of the protein in cones in all 4 mouse models (FIG. 11a-f and 12a-d). Consistent with the upregulation of HIF-1α, glucose transporter 1 (GLUT1), a HIF-1α target gene (Wang, G. L., et al. (1995) *Proc Natl Acad Sci USA* 92, 5510-4; Ebert, B. L., et al. (1995) *J Biol Chem* 270, 29083-9) also was found to be upregulated in cones, again in all 4 mouse models (FIG. 11 g-j and FIG. 12e-h). Thus HIF-1α and GLUT1 upregulation are consistent with a response in cones to overcome a shortage of glucose. It also provides a link to the decreased p*-mTOR levels found during degeneration as well as the sensitivity of p*-mTOR to glucose.

Figures 14A, 14B, 14C, 14D, 14E, 14F, 14G, 14H, 14I, 14J, 14K, 14L, 14M:
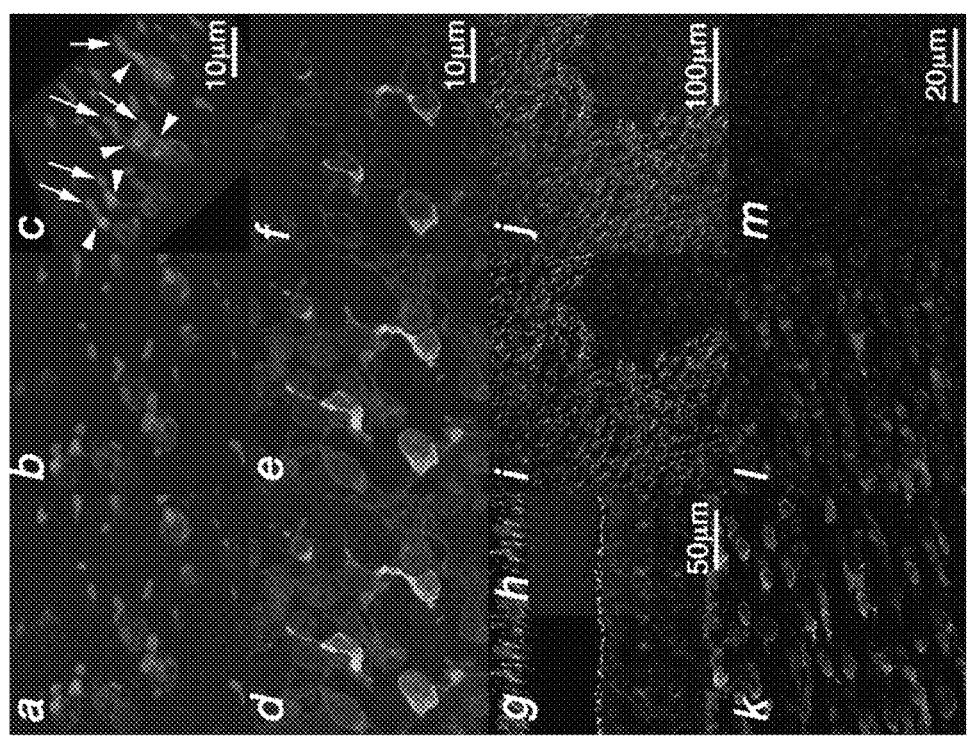
FIG. 14 depicts a retroviral vector, as described in Example 1, encoding a fusion protein between GFP and LC3 as used to infect the retinae of wild type (a-c) and PDE-β-/- (d-f) mice. Light gray signal shows expression of the fusion protein, medium gray signal shows red/green opsin expression, and dark gray signal shows nuclear DAPI staining. (a-f) Retinal flat mounts at PW10 showed uniform expression of the GFP fusion protein in cones without the formation of vesicular structures in wild type and mutant retinae. (a) DAPI overlap of (b). (c) 3D reconstruction of (b). Cone outer segments, as shown by red/green opsin signal (arrow), were attached to the cone inner segments (arrowhead), as shown by GFP signal. (d) DAPI overlap of (e). (f) Single confocal section showing cytoplasmic GFP and membrane bound red/green opsin (see also FIG. 3).

To ascertain if cones are nutritionally deprived, autophagy within cones was assessed. Two types of autophagy are inducible by various degrees of nutrient deprivation: macroautophagy and chaperone mediated autophagy (CMA) (Massey, A., et al. (2004) *Int J Biochem Cell Biol* 36, 2420-34; Finn, P. F. & Dice, J. F. (2006) *Nutrition* 22, 830-44; Codogno, P. & Meijer, A. J. (2005) *Cell Death Differ* 12 Suppl 2, 1509-18; Dice, J. F. (2007) *Autophagy* 3, 295-9). Macroautophagy is non-selective, targets proteins or entire organelles, and is marked by de novo formation of membranes that form intermediate vesicles (autophagosomes) that fuse with the lysosomes. The machinery required for macroautophagy has been shown to be present in PRs (Kunchithapautham, K. & Rohrer, B. (2007) *Autophagy* 3, 433-41). In contrast, CMA is selective and targets individual proteins for transport to the lysosomes. The presence of macroautophagy was assessed by infection with a viral vector encoding a fusion protein of green fluorescent protein (GFP) and light chain 3 (LC3), an autophagosomal membrane marker (Kabeya, Y. et al. (2000) *Embo J* 19, 5720-8; Mizushima, N., et al. (2004) *Mol Biol Cell* 15, 1101-11; Punzo, C. & Cepko, C. L. (2008) *Dev Dyn* 237, 1034-42). No difference was observed in GFP distribution in cones of wild type and mutant mice, indicating that formation of autophagosomes was absent during cone death (see FIG. 14a-f). Additionally, high levels of phosphorylated ribosomal protein S6 were found in all, or most, cones (see FIG. 14g-h) reflecting an increased activity of ribosomal S6 kinase 1 (S6K1), an inhibitor of macroautophagy (Codogno, P. & Meijer, A. J. (2005) *Cell Death Differ* 12 Suppl 2, 1509-18). Consistent with these findings is the fact that macroautophagy reflects an acute short-term response to nutrient deprivation or cellular stress conditions (Massey, A., et al. (2004) *Int J Biochem Cell Biol* 36, 2420-34; Finn, P. F. & Dice, J. F. (2006) *Nutrition* 22, 830-44). Prolonged non-selective degradation of newly synthesized proteins to overcome the stress condition would not be favorable to cells and would likely result in the relatively rapid death of most cones, rather than the slow death seen in RP.

CMA is normally activated over extended periods of starvation and results in increased levels of lysosomal-associated membrane protein (LAMP) type 2A at the lysosomal membrane (Massey, A., et al. (2004) *Int J Biochem Cell Biol* 36, 2420-34; Finn, P. F. & Dice, J. F. (2006) *Nutrition* 22, 830-44; Cuervo, A. M. & Dice, J. F. (200) *Traffic* 1, 570-83). Both starvation and oxidative stress can induce CMA (Massey, A., et al. (2004) *Int J Biochem Cell Biol* 36, 2420-34). Starvation increases LAMP-2A by preventing its degradation while oxidative stress results in de novo synthesis of LAMP-2A (Kiffin, R., et al. (2004) *Mol Biol Cell* 15, 4829-40). A LAMP-2 antibody that recognizes the proteins resulting from all 3 splice isoforms (Cuervo, A. M. & Dice, J. F. (2000) *J Cell Sci* 113 Pt 24, 4441-50) (A, B, C) showed high levels of LAMP-2 at the lysosomal membrane in all 4 mutants during cone degeneration (FIG. 13a-c; data only shown for PDE-β-/-). The high levels were specific to cones and were not seen in cells of the inner nuclear layer (FIG. 13b, c), which might reflect the possibility that cones are the only starving cells in the RP retina. qRT-PCR for the three splice isoforms showed only a minor increase in mRNA levels of LAMP-2A (1.2×) and a decrease in LAMP-2C (FIG. 13d) indicating that the increase seen in protein at the membrane is mainly due to nutritional deprivation and only to a lesser extent to oxidative stress (Komeima, K., et al. (2006) *Proc Natl Acad Sci USA* 103, 11300-5; Komeima, K., et al. (2007) *J Cell Physio* 213, 809-815; Kiffin, R., et al. (2004) *Mol Biol Cell* 15, 4829-40). Taken together, the data demonstrates that nutritional imbalance in cones leads to the activation of CMA, a process that is consistent with prolonged starvation.

Stimulation of the Insulin Receptor Pathway Prolongs Cone Survival

Figures 15A, 15B, 15C, 15D, 15E, 15F, 15G, 15H:
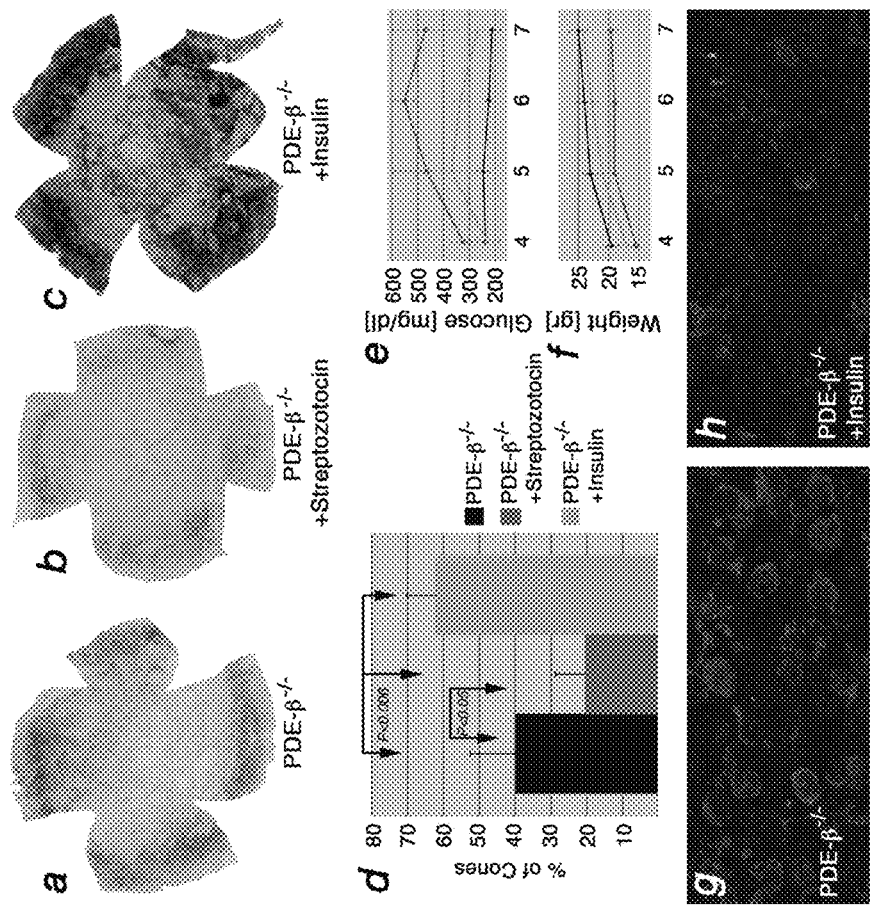
FIG. 15 depicts the affect of insulin levels on cone survival as set forth in Example 1 as follows: (a-c) Retinal flat mounts of PDE-β mutants at PW7 stained for lacZ[49,48] (dark gray) to detect cones (see Material & Methods and FIG. 16). (a) Example of untreated control. (b) Example of mouse injected with streptozotocin. (c) Example of mouse injected daily with insulin. (d) Quantification of cone survival after 4 weeks of treatment. Data represents an average of at least 8 retinae and indicates on the y-axis percentage of cone surface area versus surface area of entire retina (see FIGS. 17 and 18). (e) Measurements of blood glucose levels and body weight (f) performed weekly over the time span of the experiment. (g, h) Immunofluorescent staining on retinal flat mounts for HIF-1α (medium gray) and PNA (light gray) in untreated control PDE-β$^{-/-}$ (g) and PDE-β$^{-/-}$ mice treated for 4 weeks with insulin (h). Dark gray shows nuclear DAPI.

The data on mTOR, HIF-1α, GLUT1 and the induction of CMA demonstrated that a shortage of glucose in cones resulting in starvation and further demonstrated that the insulin/mTOR pathway plays an important role during cone death. To determine if the insulin/mTOR pathway can influence cone survival, we stimulated the pathway by systemic treatment of PDE-β-/- mice with insulin. The PDE-β mutant was chosen over the other three mutants due to its faster cone death kinetics, allowing for a better read-out of cone survival. Mice were treated with daily intraperitoneal injections of insulin over a 4 week period, starting at the onset of cone death. To reduce insulin, a single injection of streptozotocin, a drug that kills the insulin-producing beta cells of the pancreas, also was examined. Systemic administration of insulin results in a desensitized insulin receptor due to a feedback loop in the pathway, which causes an increase in blood glucose levels. Injection of streptozotocin, which also results in increased blood glucose levels, served as a control for the effect of elevated blood glucose, and also provided animals with reduced levels of insulin. PDE-β-/- mice injected with insulin showed improved cone survival compared to uninjected control mice. PDE-β-/- mice injected with Streptozotocin showed a decrease in cone survival (FIG. 15a-d). Improved cone survival was therefore due to insulin and not to the increased blood glucose levels (FIG. 15e). Additionally, cones in mutant mice treated with insulin did not show the upregulation of HIF-1α seen normally in cones during degeneration, consistent with the notion that cones were responding to insulin directly (FIG. 15g, h).

Discussion

The results presented herein show that cones exhibit signs of nutritional imbalance during the period of cone degeneration in RP mice. The microarray analysis demonstrates that there are changes in cellular metabolism involving the insulin/mTOR pathway at the onset of cone death. It was demonstrated that inhibition of mTOR in wild type mice resulted in the same pattern of loss of red/green opsin as seen during degeneration. In accord with changes in p*-mTOR, and its sensitivity to glucose, an upregulation of HIF-1α and GLUT1 was observed, demonstrating that glucose uptake, and/or the intracellular levels of glucose, may be compromised in cones of RP mice. Additionally, systemic administration of insulin prolonged cone survival, whereas depletion of endogenous insulin had the reverse effect. The systemic treatment with insulin prevented the upregulation of HIF-1α in cones seen normally during cone degeneration, demonstrating that insulin was directly acting on cones. Interestingly, a prolonged treatment of insulin during a time span of 7 weeks instead of 4 weeks did not show any significant improvement of cone survival (see FIG. 18). This may reflect the feedback loop of the pathway in which S6K1 acts directly onto the insulin-receptor substrate (IRS). The results indicate that nutrient availability in cones may be altered during the period of cone degeneration and that the insulin/mTOR pathway plays a crucial role. A recent report showed that constitutive expression of proinsulin in the rd10 mouse model of RP delays photoreceptor death, both of rods and cones (Corrochano, S. et al. (2008) *Invest Ophthalmol Vis Sci* 49, 4188-94). However, proinsulin seems not to act through the insulin receptor as mice treated with proinsulin did not develop hyperglycemia. Proinsulin blocks developmental cell death and thus may interfere with the apoptotic pathway in the postnatal retina. Macroautophagy, which is controlled by mTOR through its downstream target S6K1, was not detected during cone degeneration, while CMA appeared to be activated. Increased LAMP-2A levels at the lysosomal membrane indicated activation of CMA. In addition, the observations concerning mTOR, HIF-1α, and GLUT1 are consistent with starvation and CMA. The lack of detectable macroautophagy does not rule out the possibility that macroautophagy might occur for a short period of time (e.g., 24 hours) prior to the activation of CMA. The data only show that macroautophagy is not the main form of autophagy over an extended period of time, which is consistent with the notion that macroautophagy is a short-term response. The prolonged inhibition of macroautophagy is likely due to increased S6K1 activity as seen by increased p*-S6 levels. S6K1 is positively regulated by mTOR and AMP-activated protein kinase (AMPK) (Codogno, P. & Meijer, A. J. (2005) *Cell Death Differ* 12 Suppl 2, 1509-18), which reads out cellular ATP levels. Therefore, while mTOR may report metabolic problems with respect to glucose uptake, and reduce energy consuming processes and improve glycolysis through HIF-1α, AMPK may report normal cellular ATP levels and inhibit macroautophagy. This represents a specific response to the energy requirements of cones. Most of the glucose taken up by PRs never enters the Krebs cycle (Poitry-Yamate, et al. (1995) *J Neurosci* 15, 5179-91). Thus the shortage of glucose may not cause a shortage of ATP. Lactate, provided by Muller glia, can generate ATP via the Krebs cycle (Tsacopoulos, M., et al. (1998) *Prog Retin Eye Res* 17, 429-420. However, glucose is needed to generate NADPH in the pentose phosphate cycle, and NADPH is required for synthesis of phospholipids, the building blocks of cell membranes. PRs constantly shed their membranes at the tip of the OSs. Since reduced levels of glucose would result in reduction of membrane synthesis, the rate of OS phagocytosis by the RPE may be higher than the rate of membrane synthesis by cones. Consistent with this, OS shortening preceded cell death in these 4 models, as is also observed in human cases of RP17. Additionally, changes that affect lipid metabolism were also seen by the microarray analysis.

These studies described herein were designed to determine why the loss of rods result in cone death in RP. The previous hypotheses attributing cone death either to a toxin released by rod cells or to the lack of a trophic factor produced by rod cells and necessary for cone survival each fail to explain the pathology found in humans. The rod and cone death kinetics shown here clearly argue against a toxin produced by dying rods as a cause for cone death since the onset of cone death always occurred after the major rod death period. If a rod toxin caused cone death, then the onset of cone death should have either coincided with the onset of rod death or should have started shortly thereafter, since this would be the period of peak toxin production. Interestingly, the lack of a trophic factor produced by healthy rods and required for cone survival would agree with the onset of cone death seen in all four models as one would expect the onset of cone death during the end stages of rod death. However, the progression of cone death and the end phase of rod death make this unlikely hypothesis as the sole reason for cone death. In the two PDE mutants and in the Rho-KO mutant, cones were dying for many weeks after the end phase of rod death, indicating that they could survive quite awhile in the absence of rods. In addition, in the P23H model, rods died so slowly during the end phase of rod death, that during the entire period of cone death, rods were still present. The hypothesis that a lack of a rod trophic factor being the main cause for cone death seems unlikely given these discrepancies.

Our observations of nutritionally deprived cones demonstrate the dependence of cones on rods. The OS-RPE interactions are vital since the RPE shuttles nutrition and oxygen from the choroidal vasculature to PRs. Roughly 95% of all PRs in mouse and human are rods and approximately 20-30 OSs contact one RPE cell (Snodderly, D. M., et al. (2002) *Invest Ophthalmol Vis Sci* 43, 2815-8; Young, R. W. (1971) *Journal of Cell Biology* 49, 303-318). Thus, only 1-2 of those RPE-OS contacts are via cones. During the collapse of the ONL, the remaining cone:RPE interactions are likely perturbed. If these interactions drop below a threshold required for the proper flow of nutrients, the loss of rods results in a reduced flow of nutrients to cones. In all 4 mouse models, the onset of cone death occurred when the ONL reached one row of cells. This cell density therefore represents the critical threshold. Then, while the remaining rods die due to a mutation in a rod-specific gene, cone death begins due to nutrient deprivation. In accord with this notion, cone death progressed more slowly when the remaining rods died slowly. This mechanism would also explain why the loss of cones does not lead to rod death (Biel, M. et al. (1999) *Proc Natl Acad Sci USA* 96, 7553-7; Yang, R. B. et al. (1999) *J Neurosci* 19, 5889-970. Since in humans and mouse, cones are less than 5% of all PRs, the critical threshold that perturbs OS-RPE interactions would not be reached. Further support for this idea is provided by studies in zebrafish where the overall ratio of rods to cones is reversed (1:8). Additionally, the distribution of rods and cones in zebrafish is uneven such that certain regions are cone-rich whereas other regions are rod-rich. A recently isolated mutation in a cone-specific gene resulted in rod death, but only in regions of high cone density (Stearns, G., et al. (2007) *J Neurosci* 27, 13866-74), leading Stearns and co-workers to conclude that cell density is the crucial determinant. We determined that once a critical threshold of cell density is breached, improper OS-RPE interactions result in reduced flow of nutrients (e.g., glucose). This results in reduced OS membrane synthesis, which in turn further contributes to a reduced uptake of nutrients from the RPE. Ultimately, prolonged starvation, as indicated by the activation of CMA, leads to cell death. Since starvation can occur slowly over extended periods of time, and because the rate may fluctuate due to fluctuations in nutrient uptake, the slow and irregular demise of cones observed in humans results therefrom. Therefore, the results presented herein not only provide a new mechanism of cone death in RP that should direct future therapeutic approaches, but also consolidate the data from the literature with respect to the death kinetics of rods and cones seen in mice and patients with different RP mutations.

Example 2

Transfection of Cone Cells with Gluconeogenic Genes to Increase Cone Viability

Neurons can be compromised by genetic and environmental factors that lead to their malfunction and death. In the retina, specialized sensory neurons, the photoreceptors (rods and cones), as well as ganglion cells, the output neurons of the retina, are the neuronal cell types that malfunction and die, leading to partial or complete loss of vision. The reasons that retinal neurons die in a disease, Retinitis Pigmentosa, that leads to loss of vision have been investigated. In Retinitis Pigmentosa, mutation of a gene that is only expressed in rods leads to the death of the rods. Subsequently, cones also die. It has been discovered that cones suffer from a lack of activity in the mTOR pathway, and appear to be starving. Starvation in cones was indicated by the activation of the chaperone mediated autophagy pathway, whereby a cell digests selected proteins when under starvation conditions. Prior to autophagy, it was noted that the cone outer segments were shrinking, and that the synthesis and/or turnover of red/green opsin protein led to reduction of this protein in cones. These observations led to the determination that cones were starving due to a lack of glucose. It was reasoned that membrane biosynthesis was slowed, leading to a reduction in the size of the outer segments, which are very membrane rich. Membrane biosynthesis requires acetylCoA, which is derived from glucose (as well as other molecules). In addition, membrane biosynthesis, as well as many other anabolic reactions, require NADPH, which can be generated by the pentose phosphate pathway, which originates with glucose. The reduction in red/green opsin protein levels also was consistent with lack of a nutrient(s) as it could be due to lack of robust translation, and/or rapid turnover of this protein. In keeping with the rationale of insufficient glucose was a lack of detectable phosphorylation of mTOR in cones. It was shown that mTOR phosphorylation in cones was dependent upon glucose. Lack of mTOR phosphorylation leads to a reduction in translation and, thus, reduction in red/green opsin, as well as other proteins. Finally, the autophagy was also consistent with a reduction in nutrients, and glucose is a key nutrient. Therefore methods to supply cones with more glucose, and/or more NADPH were investigated.

Two ways were used to supply cells with more glucose. One was to increase intracellular glucose levels by providing cones with the means to synthesize their own glucose. Glucose synthesis, called gluconeogenesis, is carried out primarily in the liver, and to a limited extent in kidney and muscle. One might consider that the enzymes required for glucose synthesis could be those that break down glucose, during the process of glycolysis. However, some of the steps in glycolysis are energy producing and thus to reverse them requires a different process. Three enzymes must be supplied to allow the glucose to be synthesized, utilizing pyruvate or lactate as a starting point, and utilizing ATP and GTP to go uphill energetically in the synthesis. The first energy requiring step is catalyzed by Pcx (Pcx: Pyruvate Carboxylase)

and utilizes ATP. A subsequent energy requiring step is catalyzed by Pck1: Phosphoenolpyruvate carboxykinase) and requires GTP. The third gene that is required to carry out gluconeogenesis is Fbp1 (Fructose 1,6 biphosphatase). Both Pck1 and Fbp1 have two isoforms, known as Pck2 and Fbp2. Pck1 and Fbp1 are expressed in the liver and are located in the cytoplasm whereas Pck2 and Fbp2 are located in the mitochondria and are expressed normally in muscle cells. To allow cone cells to synthesize their own glucose, cones were infected with an AAV virus (AAV 2/5; genome from serotype 2, with rep and cap genes from serotype 5) that carries these 3 genes. The AAV2/5 has the advantage that it infects or expresses in cones. The vector design is as follows: CMV promotor-Pcx-IRES-Fbp1-IRES-Pck1 (see FIGS. 21 and 29; the sequence of the vector depicted in FIG. 29 is set forth in SEQ ID NO:11). The coding sequences for all three genes are on one transcript and the IRES elements (Internal ribosomal entry sites) allows translation of the two genes (Fbp1 and PCk1) downstream of Pcx. The endogenous expression of Fbp1, PCk1, and Pcx and the expression Fbp1, PCk1, and Pcx in the AAV vector ("construct") was analyzed by PCR analysis (FIG. 22A) and Western blot analysis (FIG. 22B).

This vector was tested in vivo in the rd1 mutant mouse, which has shown additional cone survival relative to controls. This result confirms that cones are starving due to limiting glucose. The morphology of the cone outer segments is remarkably similar to that of normal cones, with robust inner and outer segments, with red/green opsin properly localized to the outer segment. This observation also confirms that outer segment shortening was due to insufficient glucose. The animals were also tested in two behavioral assays, with infected animals demonstrating functional vision (see FIGS. 23 and 24).

An additional strategy to supply cones with more glucose is to provide them with a gene encoding a glucose transporter, such as glut1. The gene encoding glut1 is delivered using an AAV2/5 vector. There is likely excess extracellular glucose in the region around the cones. Rods constitute 97% of the cells in the area occupied by cones and, thus, the glucose that would have been taken up by the rods should still be available after the rods die. Cones with additional glut1 are able to take up more of this additional glucose. Another way to supply more nutrition to cones is to boost the uptake of nutrients from the retinal glial cell type that is in intimate contact with photoreceptors (the Muller glial cells). Muller glial cells also take up glucose and can use the glucose to produce, and then release, lactate, and perhaps pyruvate. The lactate can then be taken up by photoreceptors through a transporter, such as MCT1 or MCT2. In order to boost this process, the glut 1 gene can be delivered to Muller glia and/or the MCT1 or MCT2 gene can be delivered to photoreceptors. Finally, NADPH may be the limiting molecule that causes cones to die. NADPH is used for anabolic processes, as well as for detoxifying free oxygen radicals. After the rods die, the oxygen that would have been consumed by them is in excess in the vicinity of the cones. Excess free oxygen and light, as well as the phototransduction process, can lead to more oxygen free radicals, which are damaging to cellular macromolecules. NADPH may be utilized primarily for this purpose, reducing the supply of NADPH for anabolic processes, such as membrane biosynthesis. To supply more NADPH, the gene encoding malic enzyme is supplied in an AAV2/5 vector. This enzyme catalyzes NADPH synthesis in the cytoplasm, using malate that originates from citrate that exits from the mitochondria.

Example 3

Transfection of Cone Cells with Gluconeogenic Genes to Increase Cone Viability

As described in Example 2, AAV vectors (2/5) were created to transmit the three gluconeogenesis genes, Pcx, Pck, and Fbp-1 (as a single vector comprising the three genes operably linked to the CMV promoter), and were used to produce glucose in transfected cells.

As described below, the three genes (Pcx, Pck, and Fbp-1) were separated into different AAV vectors operably linked to the cone-specific promoter, CAR, from the cone arrestin gene. In some cases, a gluconeogenesis gene was also operably linked to the marker gene, H2BGFP, a nuclear form of GFP, or mGFP, a membrane-bound form of GFP, to allow the tracking of infected cells. FIG. 30 depicts a map of the AAV2/5 vector comprising the CAR promoter, the gluconeogenesis gene, Pcx-1, and mGFP (the sequence of this vector is set forth in SEQ ID NO:12); FIG. 31 depicts a map of the AAV2/5 vector comprising the CAR promoter and the gluconeogenesis gene, Pck-1 (the sequence of the vector is set forth in SEQ ID NO:13); FIG. 32 depicts a map of the AAV2/5 vector comprising the CAR promoter, H2BGFP, and the gluconeogenesis genes, Fbp-1 and Pck-1 (the sequence of this vector is set forth in SEQ ID NO:14); FIG. 33 depicts a map of the AAV2/5 vector comprising the CAR promoter and the gluconeogenesis gene, Fbp-1 (the sequence of this vector is set forth in SEQ ID NO:15); FIG. 34 depicts a map of the AAV2/5 vector comprising the CAR promoter and the gluconeogenesis gene, Pcx-1 (the sequence of this vector is set forth in SEQ ID NO:16).

Alternatively, an AAV-GFP vector was co-injected with the three AAV vectors comprising a gluconeogeneis gene to allow detection of successful targeting of the viral inoculum. These vectors were used to infect the retina of wild type, CD1, mice to determine if protein encoded by the three gluconeogeneis gene was produced. Retinas were injected as described and subsequently used to make protein extracts for analysis by Western blot or for immunohistochemistry.

In one series of experiments, CD1 mice were injected at postnatal day 0 (P0) with three different viral vectors, each comprising a single gluconeogeneis gene operably linked to a CAR promoter (see, e.g., FIGS. 31, 33, and 34). Retinas were harvested at P32. The viral titer for injection was about $1 \times 10^{13}$ for each individual virus. A virus expressing GFP was also co-injected at low concentration ($5 \times 10^{10}$) to identify the retinas with the best injections. Six retinas positive for GFP were processed for Western blot analysis. Each lane was loaded with 40 μg of cytoplasmic protein extract. As depicted in FIG. 25, Western blotting analysis of protein extracts from retinas of CD1 mice transfected with the three virsus, each containing one of the gluconeogeneisis genes, Pcx, Fbp1 and Pck1, demonstrates that all three genes were overexpressed as compared to un-infected control retinas.

In another series of experiments, CD1 mice were injected at postnatal day 0 (P0) with three different viral vectors each comprising a single gluconeogeneis gene operably linked to a CAR promoter (see, e.g., FIGS. 31, 33, and 34) and retinas were harvested at P32. The viral titer for injection was about $1 \times 10^{13}$ for each individual virus. A virus expressing GFP was also co-injected at low concentration ($5 \times 10^{10}$) to identify the retinas with the best injections. As shown in FIGS. 26 and 28, immunofluorescence staining of the harvested retinas demonstrates overexpression of Pcx (FIG. 26) and Fbp1 (FIG. 28) in photoreceptors.

In addition, one AAV vector comprising a gluconeogeneis gene, Pcx, operably linked to the CMV promoter and mGFP (pAAV-CMVpq-Pcx-1-mGFP) and a seond AAV vector comprising the gluconeogeneis genes, Fbp1 and Pck1, operably linked to the CMV promoter and H2BGFP (pAAV-CMVpq-H2BGFP-1-Fbp1-Pck1) were injected into CD1 mice at P0 and retinas were harvested at P18. FIG. 27 shows selective expression of Pcx in cells that are also positive for mGFP demonstrating that the overexpression of Pcx in FIG. 26 is due to specific binding of the antibody.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for inhibiting starvation of a photoreceptor cell compromised by retinitis pigmentosa, comprising contacting said cell with at least one isolated nucleic acid molecule which enhances the intracellular generation and/or uptake of glucose in said photoreceptor cell, wherein the at least one isolated nucleic acid molecule encodes an enzyme selected from the group consisting of glucose-6-phosphatase, pyruvate carboxylase, phosphoenolpyruvate carboxykinase, fructose 1,6-bisphosphatase, glucose-6-phosphate dehydrogenase, 6-phosphogluconolactonase, phosphogluconate dehydrogenase, ribulose-5-phosphate isomerase, ribulose-5-phosphate epimerase, transketolase, transaldolase, GLUT1, GLUT2, GLUT3, GLUT4, GLUT5, GLUT6, GLUT7, GLUT8, GLUT9, GLUT10, GLUT11, GLUT12, GLUT13, and GLUT14, thereby inhibiting starvation of said photoreceptor cell.

2. A method for treating or preventing retinitis pigmentosa in a subject comprising administering to said subject at least one isolated nucleic acid molecule which enhances the intracellular generation and/or uptake of glucose such that starvation of a photoreceptor cell in the subject is inhibited, wherein the at least one isolated nucleic acid molecule encodes an enzyme selected from the group consisting of glucose-6-phosphatase, pyruvate carboxylase, phosphoenolpyruvate carboxykinase, fructose 1,6-bisphosphatase, glucose-6-phosphate dehydrogenase, 6-phosphogluconolactonase, phosphogluconate dehydrogenase, ribulose-5-phosphate isomerase, ribulose-5-phosphate epimerase, transketolase, transaldolase, GLUT1, GLUT2, GLUT3, GLUT4, GLUT5, GLUT6, GLUT7, GLUT8, GLUT9, GLUT10, GLUT11, GLUT12, GLUT13, and GLUT14, thereby treating or preventing retinitis pigmentosa in said subject.

3. A method for prolonging the viability of a cone cell compromised by retinitis pigmentosa, comprising contacting said cell with at least one isolated nucleic acid molecule which enhances the intracellular generation and/or uptake of glucose such that starvation of the cone cell is inhibited, wherein the at least one isolated nucleic acid molecule encodes an enzyme selected from the group consisting of glucose-6-phosphatase, pyruvate carboxylase, phosphoenolpyruvate carboxykinase, fructose 1,6-bisphosphatase, glucose-6-phosphate dehydrogenase, 6-phosphogluconolactonase, phosphogluconate dehydrogenase, ribulose-5-phosphate isomerase, ribulose-5-phosphate epimerase, transketolase, transaldolase, GLUT1, GLUT2, GLUT3, GLUT4, GLUT5, GLUT6, GLUT7, GLUT8, GLUT9, GLUT10, GLUT11, GLUT12, GLUT13, and GLUT14, thereby prolonging the viability of said cone cell.

4. A method for prolonging the viability of a rod cell compromised by retinitis pigmentosa, comprising contacting said cell with at least one isolated nucleic acid molecules which enhances the intracellular generation and/or uptake of glucose such that starvation of the rod cell is inhibited, wherein the at least one isolated nucleic acid molecule encodes an enzyme selected from the group consisting of glucose-6-phosphatase, pyruvate carboxylase, phosphoenolpyruvate carboxykinase, fructose 1,6-bisphosphatase, glucose-6-phosphate dehydrogenase, 6-phosphogluconolactonase, phosphogluconate dehydrogenase, ribulose-5-phosphate isomerase, ribulose-5-phosphate epimerase, transketolase, transaldolase, GLUT1, GLUT2, GLUT3, GLUT4, GLUT5, GLUT6, GLUT7, GLUT8, GLUT9, GLUT10, GLUT11, GLUT12, GLUT13, and GLUT14, thereby prolonging the viability of said rod cell.

5. The method of any one of claims 1 and 2-4, wherein the at least one isolated nucleic acid molecule enhances an activity selected from the group consisting of the intracellular generation of glucose, the uptake of glucose into a cell, the intracellular generation of NADPH, metabolic flux through gluconeogenesis, metabolic flux through the pentose phosphate pathway, the ability of a cell to generate phospholipids, and the ability of a cell to detoxify free oxygen radicals.

6. The method of any one of claims 1 and 2-4, wherein the at least one isolated nucleic acid molecule reduces metabolic flux through glycolysis.

7. The method of any one of claims 1 and 2-4, wherein the at least one isolated nucleic acid molecule encodes an enzyme selected from the group consisting of glucose-6-phosphatase, pyruvate carboxylase, phosphoenolpyruvate carboxykinase, and fructose 1,6-bisphosphatase.

8. The method of any one of claims 1 and 2-4, wherein the at least one isolated nucleic acid molecule encodes an enzyme involved in the pentose phosphate pathway.

9. The method of claim 5, wherein the at least one isolated nucleic acid molecule encodes an enzyme selected from the group consisting of pyruvate carboxylase, phosphoenolpyruvate carboxykinase and fructose 1,6-bisphosphatase.

10. The method of any one of claims 1 and 2-4, wherein the at least one nucleic acid molecule is contained within a vector.

11. The method of claim 10, wherein the vector is a retrovirus, an adenovirus, an adenoviral/retroviral chimera, an adeno-associated virus (AAV), a herpes simplex virus I or II, a parvovirus, a reticuloendotheliosis virus, a poliovirus, a papillomavirus, a vaccinia virus and a lentivirus.

12. The method of claim 2, wherein the administration is intraocular administration.

13. The method of claim 12, wherein the intraocular administration is selected from the group consisting of intravitreal, subconjuctival, sub-tenon, periocular, retrobulbar, suprachoroidal, and intrascleral administration.

14. The method of any one of claim 1, 3, or 4, wherein the cell is contacted with at least two isolated nucleic acid molecules which enhance the intracellular generation and/or uptake of glucose such that starvation of the rod cell is inhibited.

15. The method of claim 2, wherein the subject is administered at least two isolated nucleic acid molecules which enhance the intracellular generation and/or uptake of glucose such that starvation of the rod cell is inhibited.

16. The method of claim 14, wherein the nucleic acid molecules are contained in a single vector.

17. The method of claim 14, wherein the nucleic acid molecules are contained in different vectors.

* * * * *

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgaaggaag tgaatgtcta catg                                          24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctcatatcc agtatgatgg c                                             21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagagtctga tatccagcat ag                                            22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gacagactga taaccagtac g                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agccatgaac ggcacagagg g                                             21
```

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cttaggctgg agccacctgg ct                                             22

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgcgggccg ccaccatggt gagcaagggc gaggagc                             37

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aggtcttctc ggacggcatc ttgtacagct cgtccatgcc gag                      43

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgccgtccg agaagacctt caagc                                          25

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atctcgagtt acacagccat tgctgtcccg aatg                                34

<210> SEQ ID NO 11
<211> LENGTH: 13045
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
cagctgcgcg ctcgctcgct cactgaggcc gcccgggcaa agcccgggcg tcgggcgacc    60

```
tttggtcgcc cggcctcagt gagcgagcga gcgcgcagag agggagtggc caactccatc    120
actaggggtt ccttgtagtt aatgattaac ccgccatgct acttatctac gtacatttat    180
attggctcat gtccaacatt accgccatgt tgacattgat tattgactag ttattaatag    240
taatcaatta cggggtcatt agttcatagc ccatatatgg agttccgcgt tacataactt    300
acggtaaatg gcccgcctgg ctgaccgccc aacgacccccc gcccattgac gtcaataatg    360
acgtatgttc ccatagtaac gccaataggg actttccatt gacgtcaatg ggtggagtat    420
ttacggtaaa ctgcccactt ggcagtacat caagtgtatc atatgccaag tacgccccct    480
attgacgtca atgacggtaa atggcccgcc tggcattatg cccagtacat gaccttatgg    540
gactttccta cttggcagta catctacgta ttagtcatcg ctattaccat ggtgatgcgg    600
ttttggcagt acatcaatgg gcgtggatag cggtttgact cacggggatt ccaagtctc    660
caccccattg acgtcaatgg gagtttgttt tggcaccaaa atcaacggga ctttccaaaa    720
tgtcgtaaca actccgcccc attgacgcaa atgggcggta ggcgtgtacg gtgggaggtc    780
tatataagca gagctcgttt agtgaaccgt cagatcgcct ggagacgcca ccacgctgt    840
tttgacctcc atagaagaca ccgggaccga tccagcctcc cctcgaagct ttacatgtgg    900
taccgagctc ggatcctgag aacttcaggg tgagtctatg ggaccttga tgttttcttt    960
cccccttcttt tctatggtta agttcatgtc ataggaaggg gagaagtaac agggtacaca   1020
tattgaccaa atcagggtaa ttttgcattt gtaattttaa aaaatgcttt cttcttttaa   1080
tatactttttt tgtttatctt atttctaata ctttccctaa tctctttctt tcagggcaat   1140
aatgatacaa tgtatcatgc ctctttgcac cattctaaag aataacagtg ataatttctg   1200
ggttaaggca atagcaatat ttctgcatat aaatatttct gcatataaat tgtaactgat   1260
gtaagaggtt tcatattgct aatagcagct acaatccagc taccattctg cttttatttt   1320
atggttggga taaggctgga ttattctgag tccaagctag gcccttttgc taatcatgtt   1380
catacctctt atcttcctcc cacagctcct gggcaacgtg ctggtctgtg tgctggccca   1440
tcactttggc aaagaattcc gcgggcggcc gccaccatgc tgaagttcca aacagttcga   1500
ggggggcctga ggctcctggg tgtccgccga tcctcctcgg cccctgttgc ctccccaaat   1560
gtccggcgtc tggagtataa gcctatcaag aaagtaatgg tggccaacag aggtgagatt   1620
gccatccgag tgtttcgtgc gtgcacagag ctgggtatcc gcacagtggc tgtctactcg   1680
gagcaggaca cagggcagat gcacaggcag aaagctgatg aagcctacct tattggccgt   1740
ggcctggcac ctgtgcaggc ctacctgcac attccagaca tcatcaaggt ggccaaggaa   1800
aatggtgtag atgcggtgca tcctggctat gggttcctct cagagcgagc agactttgcc   1860
caggcctgcc aagatgctgg agtccggttc attggtccaa gcccagaggt ggtccgcaag   1920
atgggagaca aggtggaagc ccgggccatt gccatcgctg caggcgttcc agtggtcccc   1980
ggcacggact cccccatcag ctccctgcac gaggcgcatg agttctccaa caccttcggc   2040
ttccctatta tcttcaaggc cgcctacgga ggtgggggcc gcggcatgcg ggtcgtgcat   2100
agctatgagg agttggaaga gaattacacc cgggcctact ccgaggcctt ggcagccttt   2160
gggaatggag cgttgtttgt ggagaagttc attgagaagc caaggcacat tgaggtgcag   2220
atcctagggg accagtatgg gaacatcctg cacctgtacg agcgagactg ctccatccag   2280
cgtcggcacc agaaggtggt agagatcgcc cctgctaccc acctggatcc ccaacttcgc   2340
tcacgtctca ccagtgactc tgtcaaactt gccaagcagg taggctatga aacgccggc   2400
actgtggagt tcctggtgga caagcacggc aagcactact tcatcgaggt caattcccgc   2460
```

```
ctgcaggtgg agcacacggt caccgaggag atcacagatg tggacctggt ccatgctcag    2520
atccacgtgt ccgaaggccg gagcctgcct gacctgggcc tgcggcagga gaacatccgc    2580
atcaatggct gtgccattca gtgtcgggtc accaccgagg accctgcacg cagcttccag    2640
ccagacaccg gccgcattga ggttttccgg agtggtgagg gcatgggcat ccgcctggac    2700
aacgcctctg cattccaggg cgctgtcata tcgccccact atgactctct gctcgtcaag    2760
gtcattgcac acggcaaaga ccaccccaca gctgccacca agatgagcag agccctggcc    2820
gagttccgtg tccgaggtgt aaagaccaac atccccttcc tgcagaatgt tctcaacaac    2880
cagcagttcc tggcaggcac agtggacacc cagttcatcg atgagaaccc tgagctgttc    2940
cagcttcggc ctgcacagaa ccgggccag aagttgctac attacctcgg acatgtcatg    3000
gtgaatggcc ctaccactcc aatccctgtc aatgtgagcc ccagtcctgt ggatcctgct    3060
gttcctgtgg tgcccatagg cccacctcca gctggtttca gggacatcct tctgcgagaa    3120
gggccagagg gctttgcccg agctgtgcgg aatcaccagg ggctgctgtt gatggacaca    3180
accttccggg atgcccacca gtcactactg gccactagag tgcgcacaca tgatctcaaa    3240
aagattgcgc cctatgttgc ccacaacttc aacaagctct tcagcatgga gaactgggga    3300
ggcgccacgt tcgacgttgc catgcgcttc ctgtacgagt gccctggcg gcggctccag    3360
gagctccggg agcttatccc gaacatcccg ttccagatgc tactgagggg gccaatgct    3420
gtgggctaca ccaactaccc tgacaacgtg gtcttcaagt tctgtgaggt ggccaaagag    3480
aatggtatgg acgtcttccg agtctttgac tccctcaact acttgccaaa catgctgctg    3540
ggcatggaag cagcaggcag tgctgggggt gtggtggagg ctgccatctc atacacgggg    3600
gacgtggctg accctagtcg cactaaatac tcactggagt actacatggg cttagctgaa    3660
gaactggtgc gagctggcac tcacatcctg tgcattaagg acatggcggg cctgctgaag    3720
cctgccgcct gcaccatgct ggtcagctcc ctccgggacc gattcccga cctcccactg    3780
cacatccata cccatgatac atcaggggca ggtgtggcag ccatgctggc ctgtgcacaa    3840
gcaggggctg atgttgtgga cgtggcagta gactccatgt ctgggatgac ctcacagcca    3900
agcatggggg cctggtggc ctgtaccaaa gggactcctt tggacacaga ggtaccctg    3960
gagcgtgtgt ttgactacag tgagtactgg gaaggggctc ggggactgta cgcagccttc    4020
gattgcacgg ctaccatgaa gtctggcaac tccgacgtgt atgagaatga attccaggg    4080
ggccagtaca ccaacctgca cttccaggcc catagcatgg ggcttggctc caagttcaag    4140
gaggtcaaga aggcctatgt ggaggctaac cagatgctgg gggacctcat caaggtgaca    4200
ccatcctcca agattgtggg ggacctggcc cagttcatgg tgcagaatgg gttgagccgg    4260
gcagaggcag aagctcaggc agaagagctg tccttccccc gctctgtggt ggagttcctg    4320
cagggctaca ttggcattcc ccatggggt ttccctgagc cctttcgctc taaggtgcta    4380
aaggacctgc caagaataga ggggcggcct ggagcctccc tccctcccct gaacctgaag    4440
gagctggaga aggacctgat tgataggcat ggggaggagg tgaccccaga ggacgtcctc    4500
tctgcagcca tgtaccctga tgtctttgct caattcaaag acttcacggc taccttcggc    4560
cccctggata gccttaatac tcgtctcttt cttcaaggac ccaaaattgc agaggagttt    4620
gaggttgagc tggaacgggg caagaccctg cacatcaaag ccctggctgt aagcgacctg    4680
aaccgtgctg gccagaggca ggtgttcttt gaactcaatg gcagcttcg atccattctg    4740
gttaaagaca cccaggccat gaaggagatg cacttccatc ccaaggcttt gaaggatgtg    4800
```

```
aagggccaaa ttggggcccc gatgcctggg aaggtcatag acatcaaggt ggcagcaggg    4860
gacaaggtgg ctaagggcca gcccctctgt gtgctcagcg ccatgaagat ggagactgtg    4920
gtgacttcgc ccatggaggg cactatccga aaggttcatg ttaccaagga catgactctg    4980
gaaggcgacg acctcatcct agagattgag tgagaattcc gcccctctcc ctccccccc    5040 cctaacgtta ctggccgaag ccgcttggaa taaggccggt gtgcgtttgt ctatatgtta    5100
ttttccacca tattgccgtc ttttggcaat gtgagggccc ggaaacctgg ccctgtcttc    5160
ttgacgagca ttcctagggg tctttcccct ctcgccaaag gaatgcaagg tctgttgaat    5220
gtcgtgaagg aagcagttcc tctggaagct tcttgaagac aaacaacgtc tgtagcgacc    5280 cttttgcaggc agcggaaccc cccacctggc gacaggtgcc tctgcggcca aaagccacgt    5340
gtataagata cacctgcaaa ggcggcacaa ccccagtgcc acgttgtgag ttggatagtt    5400
gtggaaagag tcaaatggct ctcctcaagc gtattcaaca aggggctgaa ggatgcccag    5460 aaggtaccc cattgtatggg atctgatctg gggcctcggt gcacatgctt acatgtgtt    5520 tagtcgaggt taaaaaacgt ctaggccccc cgaaccacgg ggacgtggtt ttcctttgaa    5580
aaacacgatg ataagcttga tcacgcgtgc caccatggcg aaccatgcgc ccttcgaaac    5640
ggatatcagc accctgaccc gcttcgtcat ggagcagggc aggaaggctc agggcacggg    5700
ggagttgacc cagctgctga attcgctctg caccgcgatc aaagccatct cgtctgcggt    5760
gcgccaggcg ggcatcgcac agctctatgg tatcgctggc tcaaccaatg tgactgggga    5820
tcaagtaaag aagctggaca tactttccaa tgacctggtg atcaatatgc tgaagtcgtc    5880
ctacgctacc tgtgttcttg tgtctgaaga aaacacaaat gccatcataa tcgaacctga    5940 gaagagggggc aaatatgttg tctgtttcga tccccttgat ggctcatcca acattgactg    6000
ccttgtgtcc atcggaacca ttttttggcat ttacagaaaa aaagtactg atgagccttc    6060 tgagaaggat gctctgcagc ccggccggga cctggtggca gccgggtatg cgctctatgg    6120
cagtgccacc atgttggtcc ttgccatgga ttgtggtgtc aactgcttca tgctggaccc    6180
gtccattgga gaattcatta tggtggacag ggacgtgaag atgaagaaga aggtaacat    6240 ctacagccctt aatgagggtt atgccaagga ctttgaccct gccatcaatg agtatctcca    6300
gaggaaaaag ttccctccgg atggttcagc cccctatggt gcccggtatg tggggtccat    6360
ggtggctgat attcaccgca ctctggtata tggagggatc ttttttatacc ccgccaacaa    6420 gaaaagccca agtggaaagc tgcggctgct gtatgagtgc aaccccatag cttatgtcat    6480
ggagaaggcc ggtgggctcg ccaccacggg ggacaaagat atattagaca tcgttcccac    6540
cgagatccac cagaaggcac cagtcgtcat ggggtcctct gaagatgtgc aggagttcct    6600
ggagatctac aggaagcaca aagccaagtg actcgaccga ttctagactc cctcccccc    6660 ccctaacgtt actggccgaa gccgcttgga ataaggccgg tgtgcgtttg tctatatgtt    6720
atttttcacc atattgccgt cttttggcaa tgtgagggcc cggaaacctg gccctgtctt    6780
cttgacgagc attcctaggg gtctttcccc tctcgccaaa ggaatgcaag gtctgttgaa    6840
tgtcgtgaag gaagcagttc ctctggaagc ttcttgaaga caaacaacgt ctgtagcgac    6900
cctttgcagg cagcggaacc cccacctgg cgacaggtgc ctctgcggcc aaaagccacg    6960
tgtataagat acacctgcaa aggcggcaca accccagtgc cacgttgtga gttggatagt    7020
tgtggaaaga gtcaaatggc tctcctcaag cgtattcaac aaggggctga aggatgccca    7080
gaaggtaccc cattgtatgg gatctgatct ggggcctcgg tgcacatgct ttacgtgtgt    7140
ttagtcgagg ttaaaaaacg tctaggcccc cgaaccacg gggacgtggt tttcctttga    7200
```

```
aaaacacgat gataatacca tggccatgcc tcctcagctg cataacggtc tggacttctc    7260
tgccaaggtc atccagggca gcctcgacag cctgccccag gcagtgagga agttcgtgga    7320
aggcaatgct cagctgtgcc agccggagta tatccacatc tgcgatggct ccgaggagga    7380
gtacgggcag ttgctgaccc acatgcagga ggagggtgtc atccgcaagc tgaagaaata    7440
tgacaactgt tggctggctc tcactgaccc tcgagatgtg gccaggatcg aaagcaagac    7500
agtcatcatc acccaagagc agagagacac agtgcccatc cccaaaactg gcctcagcca    7560
gctgggccgc tggatgtcgg aagaggactt tgagaaagca ttcaacgcca ggttcccagg    7620
gtgcatgaaa ggccgcacca tgtatgtcat cccattcagc atggggccac tgggctcgcc    7680
gctggccaag attggtattg aactgacaga ctcgccctat gtggtggcca gcatgcggat    7740
catgactcgg atgggcatat ctgtgctgga ggccctggga gatggggagt tcatcaagtg    7800
cctgcactct gtggggtgcc ctctcccctt aaaaaagcct ttggtcaaca actgggcctg    7860
caaccctgag ctgaccctga tcgcccacct cccggaccgc agagagatca tctcctttgg    7920
aagcggatat ggtgggaact cactactcgg gaagaaatgc tttgcgttgc ggatcgccag    7980
ccgtctggct aaggaggaag ggtggctggc ggagcatatg ctgatcctgg gcataactaa    8040
ccccgaaggc aagaagaaat acctggccgc agccttccct agtgcctgtg ggaagaccaa    8100
cttggccatg atgaaccccc agcctgccgg gtggaaggtc gaatgtgtgg gcgatgacat    8160
cgcctggatg aagtttgatg cccaaggcaa cttaagggct atcaacccag aaaacgggtt    8220
ttttggagtt gctcctggca cctcagtgaa gacaaatcca aatgccatta aaaccatcca    8280
gaaaaacacc atcttcacca cgtggctgag gactagcgat gggggtgttt actgggaagg    8340
catcgatgag ccgctggccc cgggagtcac catcacctcc tggaagaaca aggagtggag    8400
accgcaggac gcggaaccat gtgcccatcc caactcgaga ttctgcaccc ctgccagcca    8460
gtgccccatt attgaccctg cctgggaatc tccagaagga gtaccattg agggtatcat    8520 cttttggtggc cgtagacctg aaggtgtccc ccttgtctat gaagccctca gctggcagca    8580
tggggtgttt gtaggagcag ccatgagatc tgaggccaca gctgctgcag aacacaaggg    8640
caagatcatc atgcacgacc cctttgccat gcgacccttc ttcggctaca acttcggcaa    8700 ataccctggcc cactggctga gcatggccca ccgcccagca gccaagttgc ccaagatctt    8760
ccatgtcaac tggttccgga aggacaaaga tgcaagttc ctctggccag gctttggcga    8820
gaactcccgg gtgctggagt ggatgttcgg gcggattgaa ggggaagaca gcgccaagct    8880
cacgcccatc ggctacatcc ctaaggaaaa cgccttgaac ctgaaaggcc tggggggcgt    8940
caacgtggag gagctgtttg ggatctctaa ggagttctgg gagaaggagg tggaggagat    9000
cgacaggtat ctgaggacc aggtcaacac cgacctccct tacgaaattg agagggagct    9060
ccgagccctg aaacagagaa tcagccagat gtaagcggcc gctctagagg atccaagctt    9120
atcgataccg tcgacctcga gtgctttatt tgtgaaattt gtgatactat tgctttattt    9180
gtaaccatta taagctgcaa taaacaagtt aacaacaaca attgcattca ttttattgtt    9240
tcaggttcag ggggaggtgt gggaggtttt ttaaagggg aggggtacg tagataagta    9300 gcatggcggg ttaatcatta actacaagga accctagtg atggagttgg ccactccctc    9360
tctgcgcgct cgctcgctca ctgaggccgg gcgaccaaag gtcgcccgac gcccgggctt    9420 tgccgggcg gcctcagtga gcgagcgagc gcgccagctg gcgtaatagc gaagaggccc    9480
gcaccgatcg cccttcccaa cagttgcgca gcctgaatgg cgaatggcga ttctgttgca    9540
```

```
atggctggcg gtaatattgt tctggatatt accagcaagg ccgatagttt gagttcttct    9600
actcaggcaa gtgatgttat tactaatcaa agaagtattg cgacaacggt taatttgcgt    9660
gatggacaga ctcttttact cggtggcctc actgattata aaaacacttc tcaggattct    9720
ggcgtaccgt tcctgtctaa aatccctta atcggcctcc tgtttagctc ccgctctgat    9780
tctaacgagg aaagcacgtt atacgtgctc gtcaaagcaa ccatagtacg cgccctgtag    9840
cggcgcatta agcgcggcgg gtgtggtggt tacgcgcagc gtgaccgcta cacttgccag    9900
cgccctagcg cccgctcctt tcgctttctt cccttccttt ctcgccacgt tcgccggctt    9960
tccccgtcaa gctctaaatc ggggctccc tttagggttc cgatttagtg ctttacggca   10020
cctcgacccc aaaaaacttg attagggtga tggttcacgt agtgggccat cgccctgata   10080
gacggttttt cgccctttga cgttggagtc cacgttcttt aatagtggac tcttgttcca   10140
aactggaaca acactcaacc ctatctcggt ctattctttt gatttataag ggattttgcc   10200
gatttcggcc tattggttaa aaatgagct gatttaacaa aaatttaacg cgaatttta   10260
caaaatatta acgtttacaa tttaaatatt tgcttataca atcttcctgt ttttgggct   10320
tttctgatta tcaaccgggg tacatatgat tgacatgcta gttttacgat taccgttcat   10380
cgattctctt gtttgctcca gactctcagg caatgacctg atagcctttg tagagacctc   10440
tcaaaaatag ctaccctctc cggcatgaat ttatcagcta gaacggttga atatcatatt   10500
gatggtgatt tgactgtctc cggcctttct cacccgtttg aatctttacc tacacattac   10560
tcaggcattg catttaaaat atatgagggt tctaaaaatt tttatccttg cgttgaaata   10620
aaggcttctc ccgcaaaagt attacaggg cataatgttt ttggtacaac cgatttagct   10680
ttatgctctg aggctttatt gcttaatttt gctaattctt tgccttgcct gtatgattta   10740
ttggatgttg gaatgccctg atgcggtatt ttctccttac gcatctgtgc ggtatttcac   10800
accgcatatg gtgcactctc agtacaatct gctctgatgc cgcatagtta agccagcccc   10860
gacacccgcc aacacccgct gacgcgccct gacgggcttg tctgctcccg gcatccgctt   10920
acagacaagc tgtgaccgtc tccgggagct gcatgtgtca gaggttttca ccgtcatcac   10980
cgaaacgcgc gagacgaaag ggcctcgtga tacgcctatt tttataggtt aatgtcatga   11040
taataatggt ttcttagacg tcaggtggca cttttcgggg aaatgtgcgc ggaacccta   11100
tttgtttatt tttctaaata cattcaaata tgtatccgct catgagacaa taaccctgat   11160
aaatgcttca ataatattga aaaggaaga gtatgagtat tcaacatttc cgtgtcgccc   11220
ttattccctt ttttgcggca ttttgccttc ctgttttgc tcacccagaa acgctggtga   11280
aagtaaaaga tgctgaagat cagttgggtg cacgagtggg ttacatcgaa ctggatctca   11340
acagcggtaa gatccttgag agttttcgcc ccgaagaacg ttttccaatg atgagcactt   11400
ttaaagttct gctatgtggc gcggtattat cccgtattga cgccgggcaa gagcaactcg   11460
gtcgccgcat acactattct cagaatgact tggttgagta ctcaccagtc acagaaaagc   11520
atcttacgga tggcatgaca gtaagagaat tatgcagtgc tgccataacc atgagtgata   11580
acactgcggc caacttactt ctgacaacga tcggaggacc gaaggagcta accgcttttt   11640
tgcacaacat gggggatcat gtaactcgcc ttgatcgttg ggaaccggag ctgaatgaag   11700
ccataccaaa cgacgagcgt gacaccacga tgcctgtagc aatggcaaca acgttgcgca   11760
aactattaac tggcgaacta cttactctag cttcccggca acaattaata gactggatgg   11820
aggcggataa agttgcagga ccacttctgc gctcggccct tccggctggc tggtttattg   11880
ctgataaatc tggagccggt gagcgtgggt ctcgcggtat cattgcagca ctggggccag   11940
```

```
atggtaagcc ctcccgtatc gtagttatct cacgacggg gagtcaggca actatggatg    12000
aacgaaatag acagatcgct gagataggtg cctcactgat taagcattgg taactgtcag    12060 accaagtttta ctcatatata ctttagattg atttaaaact tcattttttaa tttaaaagga   12120 tctaggtgaa gatccttttt gataatctca tgaccaaaat cccttaacgt gagttttcgt    12180
tccactgagc gtcagacccc gtagaaaaga tcaaggatc ttcttgagat ccttttttttc    12240 tgcgcgtaat ctgctgcttg caaacaaaaa aaccaccgct accagcggtg gtttgtttgc    12300
cggatcaaga gctaccaact cttttttccga aggtaactgg cttcagcaga gcgcagatac    12360
caaatactgt ccttctagtg tagccgtagt taggccacca cttcaagaac tctgtagcac    12420
cgcctacata cctcgctctg ctaatcctgt taccagtggc tgctgccagt ggcgataagt    12480
cgtgtcttac cgggttggac tcaagacgat agttaccgga taaggcgcag cggtcgggct    12540 gaacggggg ttcgtgcaca cagcccagct tggagcgaac gacctacacc gaactgagat    12600
acctacagcg tgagctatga gaaagcgcca cgcttcccga aggagaaaag gcggacaggt    12660
atccggtaag cggcagggtc ggaacaggag agcgcacgag ggagcttcca gggggaaacg    12720
cctggtatct ttatagtcct gtcgggtttc gccacctctg acttgagcgt cgattttgt    12780 gatgctcgtc agggggcgg agcctatgga aaaacgccag caacgcggcc ttttacggt    12840 tcctggcctt tgctggcct tttgctcaca tgttctttcc tgcgttatcc cctgattctg    12900
tggataaccg tattaccgcc tttgagtgag ctgataccgc tcgccgcagc cgaacgaccg    12960
agcgcagcga gtcagtgagc gaggaagcgg aagagcgccc aatacgcaaa ccgcctctcc    13020
ccgcgcgttg gccgattcat taatg                                         13045
```

<210> SEQ ID NO 12
<211> LENGTH: 9570
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac gtacatttat    180
attggctcat gtccaacatt accgccatgt tgacattgat tattgactag acttttttt    240 tacctttttg gttcctttgg ccttttggct tttggcttcc agggcttctg gatccccccc    300
aacccctccc atacacatac acatgtgcac tcgtgcactc aacccagcac aggataatgt    360
tcattcttga cctttccaca tacatctggc tatgttctct ctcttatcta caataaatct    420
cctccactat acttaggagc agttatgttc ttcttcttttc tttctttttt tttttttca    480 ttcagtaaca tcatcagaat cccctagctc tggcctacct cctcagtaac aatcagctga    540
tccctggcca ctaatctgta ctcactaatc tgttttccaa actcttggcc cctgagctaa    600
ttatagcagt gcttcatgcc acccacccca accctattct tgttctctga ctcccactaa    660
tctacacatt cagaggattg tggatataag aggctgggag gccagcttag caaccagagc    720
tggaggctgc gcggccgcca ccatgctgaa gttccaaaca gttcgagggg gcctgaggct    780
cctgggtgtc cgccgatcct cctcggcccc tgttgcctcc ccaaatgtcc ggcgtctgga    840
gtataagcct atcaagaaag taatggtggc caacagaggt gagattgcca tccgagtgtt    900
```

```
tcgtgcgtgc acagagctgg gtatccgcac agtggctgtc tactcggagc aggacacagg    960
gcagatgcac aggcagaaag ctgatgaagc ctaccttatt ggccgtggcc tggcacctgt   1020
gcaggcctac ctgcacattc agacatcat caaggtggcc aaggaaaatg tgtagatgc    1080 ggtgcatcct ggctatgggt tcctctcaga gcgagcagac tttgcccagg cctgccaaga   1140
tgctggagtc cggttcattg gtccaagccc agaggtggtc cgcaagatgg agacaaggt    1200 ggaagcccgg gccattgcca tcgctgcagg cgttccagtg gtccccggca cggactcccc   1260
catcagctcc ctgcacgagg cgcatgagtt ctccaacacc ttcggcttcc ctattatctt   1320
caaggccgcc tacggaggtg ggggccgcgc catgcgggtc gtgcatagct atgaggagtt   1380
ggaagagaat tacacccggg cctactccga ggccttggca gcctttggga tggagcgtt    1440 gtttgtggag aagttcattg agaagccaag gcacattgag gtgcagatcc taggggacca   1500
gtatgggaac atcctgcacc tgtacgagcg agactgctcc atccagcgtc ggcaccagaa   1560
ggtggtagag atcgcccctg ctacccacct ggatccccaa cttcgctcac gtctcaccag   1620
tgactctgtc aaacttgcca agcaggtagg ctatgagaac gccggcactg tggagttcct   1680
ggtggacaag cacggcaagc actacttcat cgaggtcaat tcccgcctgc aggtggagca   1740
cacggtcacc gaggagatca cagatgtgga cctggtccat gctcagatcc acgtgtccga   1800
aggccggagc ctgcctgacc tgggcctgcg gcaggagaac atccgcatca atggctgtgc   1860
cattcagtgt cgggtcacca ccgaggaccc tgcacgcagc ttccagccag acaccggccg   1920
cattgaggtt ttccggagtg gtgagggcat gggcatccgc ctggacaacg cctctgcatt   1980
ccagggcgct gtcatatcgc cccactatga ctctctgctc gtcaaggtca ttgcacacgg   2040
caaagaccac cccacagctg ccaccaagat gagcagagcc ctggccgagt tccgtgtccg   2100
aggtgtaaag accaacatcc ccttcctgca gaatgttctc aacaaccagc agttcctggc   2160
aggcacagtg gacacccagt tcatcgatga gaaccctgag ctgttccagc ttcggcctgc   2220
acagaaccgg gcccagaagt tgctacatta cctcggacat gtcatggtga atggccctac   2280
cactccaatc cctgtcaatg tgagccccag tcctgtggat cctgctgttc ctgtggtgcc   2340
cataggccca cctccagctg gtttcaggga catccttctg cgagaagggc cagagggctt   2400
tgcccgagct gtgcggaatc accagggggct gctgttgatg gacacaacct tccgggatgc   2460
ccaccagtca ctactggcca ctagagtgcg cacacatgat ctcaaaaaga ttgcgcccta   2520
tgttgcccac aacttcaaca agctcttcag catggagaac tgggggaggcg ccacgttcga   2580 cgttgccatg cgcttcctgt acgagtgccc ctggcggcgg ctccaggagc tccgggagct   2640
tatcccgaac atcccgttcc agatgctact gaggggggcc aatgctgtgg gctacaccaa   2700
ctaccctgac aacgtggtct tcaagttctg tgaggtggcc aaagagaatg gtatggacgt   2760
cttccgagtc tttgactccc tcaactactt gccaaacatg ctgctgggca tggaagcagc   2820
aggcagtgct gggggtgtgg tggaggctgc catctcatac acgggggacg tggctgaccc   2880
tagtcgcact aaatactcac tggagtacta catgggctta gctgaagaac tggtgcgagc   2940
tggcactcac atcctgtgca ttaaggacat ggcgggcctg ctgaagcctg ccgcctgcac   3000
catgctggtc agctccctcc gggaccgatt ccccgacctc ccactgcaca tccataccca   3060
tgatacatca ggggcaggtg tggcagccat gctggcctgt gcacaagcag ggctgatgt    3120 tgtggacgtg gcagtagact ccatgtctgg gatgacctca cagccaagca tggggggccct   3180 ggtggcctgt accaaaggga ctcctttgga cacagaggta cccctggagc gtgtgtttga   3240
```

```
ctacagtgag tactgggaag gggctcgggg actgtacgca gccttcgatt gcacggctac    3300
catgaagtct ggcaactccg acgtgtatga gaatgagatt ccaggggcc  agtacaccaa    3360 cctgcacttc caggcccata gcatggggct tggctccaag ttcaaggagg tcaagaaggc    3420
ctatgtggag gctaaccaga tgctggggga cctcatcaag gtgacaccat cctccaagat    3480
tgtgggggac ctggcccagt tcatggtgca gaatgggttg agccgggcag aggcagaagc    3540
tcaggcagaa gagctgtcct tcccccgctc tgtggtggag ttcctgcagg gctacattgg    3600
cattccccat gggggtttcc ctgagccctt tcgctctaag gtgctaaagg acctgccaag    3660
aatagagggg cggcctggag cctccctccc tcccctgaac ctgaaggagc tggagaagga    3720
cctgattgat aggcatgggg aggaggtgac cccagaggac gtcctctctg cagccatgta    3780
ccctgatgtc tttgctcaat tcaaagactt cacggctacc ttcggccccc tggatagcct    3840
taatactcgt ctctttcttc aaggacccaa aattgcagag gagtttgagg ttgagctgga    3900
acggggcaag accctgcaca tcaaagccct ggctgtaagc gacctgaacc gtgctggcca    3960
gaggcaggtg ttctttgaac tcaatgggca gcttcgatcc attctggtta aagacaccca    4020
ggccatgaag gagatgcact tccatcccaa ggctttgaag gatgtgaagg gccaaattgg    4080
ggccccgatg cctgggaagg tcatagacat caaggtggca gcagggggaca aggtggctaa    4140 gggccagccc ctctgtgtgc tcagcgccat gaagatggag actgtggtga cttcgcccat    4200
ggagggcact atccgaaagg ttcatgttac caaggacatg actctggaag cgacgacct    4260 catcctagag attgagtgag aattccgccc ctctccctcc ccccccccta acgttactgg    4320
ccgaagccgc ttggaataag gccggtgtgc gtttgtctat atgttatttt ccaccatatt    4380
gccgtctttt ggcaatgtga gggcccggaa acctggccct gtcttcttga cgagcattcc    4440
taggggtctt tcccctctcg ccaaaggaat gcaaggtctg ttgaatgtcg tgaaggaagc    4500
agttcctctg gaagcttctt gaagacaaac aacgtctgta gcgaccctt  gcaggcagcg    4560 gaacccccca cctggcgaca ggtgcctctg cggccaaaag ccacgtgtat aagatacacc    4620
tgcaaaggcg gcacaacccc agtgccacgt tgtgagttgg atagttgtgg aaagagtcaa    4680
atggctctcc tcaagcgtat tcaacaaggg gctgaaggat gcccagaagg tacccccattg    4740 tatgggatct gatctggggc ctcggtgcac atgctttaca tgtgtttagt cgaggttaaa    4800
aaacgtctag gccccccgaa ccacggggac gtggttttcc tttgaaaaac acgatgataa    4860
gcttgatcac gcgtgccacc atgctgtgct gtatgagaag aaccaaacag gttgaaaaga    4920
atgatgagga ccaaaagatc atggtgagca agggcgagga gctgttcacc ggggtggtgc    4980
ccatcctggt cgagctggac ggcgacgtaa acggccacaa gttcagcgtg tccggcgagg    5040
gcgagggcga tgccacctac ggcaagctga ccctgaagtt catctgcacc accggcaagc    5100
tgcccgtgcc ctggcccacc ctcgtgacca ccctgaccta cggcgtgcag tgcttcagcc    5160
gctaccccga ccacatgaag cagcacgact tcttcaagtc cgccatgccc gaaggctacg    5220
tccaggagcg caccatcttc ttcaaggacg acggcaacta caagacccgc gccgaggtga    5280
agttcgaggg cgacaccctg gtgaaccgca tcgagctgaa gggcatcgac ttcaaggagg    5340
acggcaacat cctggggcac aagctggagt acaactacaa cagccacaac gtctatatca    5400
tggccgacaa gcagaagaac ggcatcaagg tgaacttcaa gatccgccac aacatcgagg    5460
acggcagcgt gcagctcgcc gaccactacc agcagaacac ccccatcggc gacggccccg    5520
tgctgctgcc cgacaaccac tacctgagca cccagtccgc cctgagcaaa gaccccaacg    5580
agaagcgcga tcacatggtc ctgctggagt tcgtgaccgc cgccgggatc actctcggca    5640
```

```
tggacgagct gtacaagtaa ctcgagtgct ttatttgtga aatttgtgat actattgctt    5700
tatttgtaac cattataagc tgcaataaac aagttaacaa caacaattgc attcatttta    5760
ttgtttcagg ttcaggggga ggtgtgggag gttttttaaa ggggagggg gtacgtagat     5820 aagtagcatg cgggttaat cattaactac aaggaacccc tagtgatgga gttggccact    5880
ccctctctgc gcgctcgctc gctcactgag gccgggcgac caaaggtcgc ccgacgcccg    5940
ggctttgccc gggcggcctc agtgagcgag cgagcgcgcc agctggcgta atagcgaaga    6000
ggcccgcacc gatcgccctt cccaacagtt gcgcagcctg aatggcgaat ggcgattctg    6060
ttgcaatggc tggcggtaat attgttctgg atattaccag caaggccgat agtttgagtt    6120
cttctactca ggcaagtgat gttattacta atcaaagaag tattgcgaca acggttaatt    6180
tgcgtgatgg acagactctt ttactcggtg gcctcactga ttataaaaac acttctcagg    6240
attctggcgt accgttcctg tctaaaatcc ctttaatcgg cctcctgttt agctcccgct    6300
ctgattctaa cgaggaaagc acgttatacg tgctcgtcaa agcaaccata gtacgcgccc    6360
tgtagcggcg cattaagcgc ggcgggtgtg gtggttacgc gcagcgtgac cgctacactt    6420
gccagcgccc tagcgcccgc tcctttcgct ttcttccctt cctttctcgc cacgttcgcc    6480
ggctttcccc gtcaagctct aaatcggggg ctccctttag ggttccgatt tagtgcttta    6540
cggcacctcg accccaaaaa acttgattag ggtgatggtt cacgtagtgg gccatcgccc    6600
tgatagacgg ttttcgccc tttgacgttg gagtccacgt tctttaatag tggactcttg    6660
ttccaaactg gaacaacact caaccctatc tcggtctatt cttttgattt ataagggatt    6720
ttgccgattt cggcctattg gttaaaaaat gagctgattt aacaaaaatt taacgcgaat    6780
tttaacaaaa tattaacgtt tacaatttaa atatttgctt atacaatctt cctgtttttg    6840
gggcttttct gattatcaac cggggtacat atgattgaca tgctagtttt acgattaccg    6900
ttcatcgatt ctcttgtttg ctccagactc tcaggcaatg acctgatagc ctttgtagag    6960
acctctcaaa aatagctacc ctctccggca tgaatttatc agctagaacg gttgaatatc    7020
atattgatgg tgatttgact gtctccggcc tttctcaccc gtttgaatct ttacctacac    7080
attactcagg cattgcattt aaaatatatg agggttctaa aaattttat ccttgcgttg     7140 aaataaaggc ttctcccgca aaagtattac agggtcataa tgtttttggt acaaccgatt    7200
tagctttatg ctctgaggct ttattgctta attttgctaa ttctttgcct tgcctgtatg    7260
atttattgga tgttggaatg ccctgatgcg gtattttctc cttacgcatc tgtgcggtat    7320
ttcacaccgc atatggtgca ctctcagtac aatctgctct gatgccgcat agttaagcca    7380
gccccgacac ccgccaacac ccgctgacgc gccctgacgg gcttgtctgc tcccggcatc    7440
cgcttacaga caagctgtga ccgtctccgg gagctgcatg tgtcagaggt tttcaccgtc    7500
atcaccgaaa cgcgcgagac gaaagggcct cgtgatacgc ctatttttat aggttaatgt    7560
catgataata atggtttctt agacgtcagg tggcactttt cggggaaatg tgcgcggaac    7620
ccctatttgt ttatttttct aaatacattc aaatatgtat ccgctcatga gacaataacc    7680
ctgataaatg cttcaataat attgaaaaag gaagagtatg agtattcaac atttccgtgt    7740
cgcccttatt ccctttttg cggcattttg ccttcctgtt tttgctcacc cagaaacgct    7800
ggtgaaagta aaagatgctg aagatcagtt gggtgcacga gtgggttaca tcgaactgga    7860
tctcaacagc ggtaagatcc ttgagagttt tcgccccgaa gaacgttttc caatgatgag    7920
cacttttaaa gttctgctat gtggcgcggt attatcccgt attgacgccg ggcaagagca    7980
```

| | | | | |
|---|---|---|---|---|
| actcggtcgc | cgcatacact | attctcagaa | tgacttggtt | gagtactcac cagtcacaga | 8040 |
| aaagcatctt | acggatggca | tgacagtaag | agaattatgc | agtgctgcca taaccatgag | 8100 |
| tgataacact | gcggccaact | tacttctgac | aacgatcgga | ggaccgaagg agctaaccgc | 8160 |
| ttttttgcac | aacatggggg | atcatgtaac | tcgccttgat | cgttgggaac cggagctgaa | 8220 |
| tgaagccata | ccaaacgacg | agcgtgacac | cacgatgcct | gtagcaatgg caacaacgtt | 8280 |
| gcgcaaacta | ttaactggcg | aactacttac | tctagcttcc | cggcaacaat taatagactg | 8340 |
| gatggaggcg | gataaagttg | caggaccact | tctgcgctcg | gcccttccgg ctggctggtt | 8400 |
| tattgctgat | aaatctggag | ccggtgagcg | tgggtctcgc | ggtatcattg cagcactggg | 8460 |
| gccagatggt | aagccctccc | gtatcgtagt | tatctacacg | acggggagtc aggcaactat | 8520 |
| ggatgaacga | aatagacaga | tcgctgagat | aggtgcctca | ctgattaagc attggtaact | 8580 |
| gtcagaccaa | gtttactcat | atatacttta | gattgattta | aaacttcatt tttaatttaa | 8640 |
| aaggatctag | gtgaagatcc | ttttttgataa | tctcatgacc | aaaatccctt aacgtgagtt | 8700 |
| ttcgttccac | tgagcgtcag | accccgtaga | aaagatcaaa | ggatcttctt gagatccttt | 8760 |
| ttttctgcgc | gtaatctgct | gcttgcaaac | aaaaaaacca | ccgctaccag cggtggtttg | 8820 |
| tttgccggat | caagagctac | caactctttt | tccgaaggta | actggcttca gcagagcgca | 8880 |
| gataccaaat | actgtccttc | tagtgtagcc | gtagttaggc | caccacttca agaactctgt | 8940 |
| agcaccgcct | acatacctcg | ctctgctaat | cctgttacca | gtggctgctg ccagtggcga | 9000 |
| taagtcgtgt | cttaccgggt | tggactcaag | acgatagtta | ccggataagg cgcagcggtc | 9060 |
| gggctgaacg | gggggttcgt | gcacacagcc | cagcttggag | cgaacgacct acaccgaact | 9120 |
| gagataccta | cagcgtgagc | tatgagaaag | cgccacgctt | cccgaaggga gaaaggcgga | 9180 |
| caggtatccg | gtaagcggca | gggtcggaac | aggagagcgc | acgagggagc ttccaggggg | 9240 |
| aaacgcctgg | tatctttata | gtcctgtcgg | gtttcgccac | ctctgacttg agcgtcgatt | 9300 |
| tttgtgatgc | tcgtcagggg | ggcggagcct | atggaaaaac | gccagcaacg cggccttttt | 9360 |
| acggttcctg | gccttttgct | ggccttttgc | tcacatgttc | tttcctgcgt tatcccctga | 9420 |
| ttctgtggat | aaccgtatta | ccgcctttga | gtgagctgat | accgctcgcc gcagccgaac | 9480 |
| gaccgagcgc | agcgagtcag | tgagcgagga | agcggaagag | cgcccaatac gcaaaccgcc | 9540 |
| tctccccgcg | cgttggccga | ttcattaatg | | | 9570 |

<210> SEQ ID NO 13
<211> LENGTH: 6548
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

| | | | | |
|---|---|---|---|---|
| cagctgcgcg | ctcgctcgct | cactgaggcc | gcccgggcaa | agcccgggcg tcgggcgacc | 60 |
| tttggtcgcc | cggcctcagt | gagcgagcga | gcgcgcagag | agggagtggc caactccatc | 120 |
| actaggggtt | ccttgtagtt | aatgattaac | ccgccatgct | acttatctac gtacatttat | 180 |
| attggctcat | gtccaacatt | accgccatgt | tgacattgat | tattgactag actttttttt | 240 |
| tacctttttg | gttcctttgg | ccttttggct | tttggcttcc | agggcttctg gatcccccc | 300 |
| aaccccctccc | atacacatac | acatgtgcac | tcgtgcactc | aacccagcac aggataatgt | 360 |
| tcattcttga | cctttccaca | tacatctggc | tatgttctct | ctcttatcta caataaatct | 420 |

```
cctccactat acttaggagc agttatgttc ttcttctttc tttctttttt tttttttca      480 ttcagtaaca tcatcagaat ccctagctc tggcctacct cctcagtaac aatcagctga      540
tccctggcca ctaatctgta ctcactaatc tgttttccaa actcttggcc cctgagctaa     600
ttatagcagt gcttcatgcc acccacccca accctattct tgttctctga ctcccactaa     660
tctacacatt cagaggattg tggatataag aggctgggag gccagcttag caaccagagc     720
tggaggctgc gcggccgcca ccatgcctcc tcagctgcat aacggtctgg acttctctgc     780
caaggtcatc cagggcagcc tcgacagcct gccccaggca gtgaggaagt tcgtggaagg     840
caatgctcag ctgtgccagc cggagtatat ccacatctgc gatggctccg aggaggagta     900
cgggcagttg ctgaccccaca tgcaggagga gggtgtcatc cgcaagctga agaaatatga     960
caactgttgg ctggctctca ctgaccctcg agatgtggcc aggatcgaaa gcaagacagt    1020
catcatcacc caagagcaga gagacacagt gcccatcccc aaaactggcc tcagccagct    1080
gggccgctgg atgtcggaag aggactttga gaaagcattc aacgccaggt tcccagggtg    1140
catgaaaggc cgcaccatgt atgtcatccc attcagcatg gggccactgg gctcgccgct    1200
ggccaagatt ggtattgaac tgacagactc gccctatgtg gtggccagca tgcggatcat    1260
gactcggatg ggcatatctg tgctggaggc cctgggagat ggggagttca tcaagtgcct    1320
gcactctgtg gggtgccctc tccccttaaa aaagcctttg gtcaacaact gggcctgcaa    1380 cccctgagctg accctgatcg cccacctccc ggaccgcaga gagatcatct cctttggaag    1440
cggatatggt gggaactcac tactcgggaa gaaatgcttt gcgttgcgga tcgccagccg    1500
tctggctaag gaggaagggt ggctggcgga gcatatgctg atcctgggca taactaaccc    1560
cgaaggcaag aagaaatacc tggccgcagc cttccctagt gcctgtggga agaccaactt    1620
ggccatgatg aaccccagcc tgcccgggtg gaaggtcgaa tgtgtgggcg atgacatcgc    1680
ctggatgaag tttgatgccc aaggcaactt aagggctatc aacccagaaa cgggttttt    1740 tggagttgct cctggcacct cagtgaagac aaatccaaat gccattaaaa ccatccagaa    1800
aaacaccatc ttcaccaacg tggctgagac tagcgatggg ggtgtttact gggaaggcat    1860
cgatgagccg ctggccccgg gagtcaccat cacctcctgg aagaacaagg agtggagacc    1920
gcaggacgcg gaaccatgtg cccatcccaa ctcgagattc tgcaccctg ccagccagtg    1980 ccccattatt gaccctgcct gggaatctcc agaaggagta cccattgagg gtatcatctt    2040
tggtggccgt agacctgaag gtgtccccct tgtctatgaa gccctcagct ggcagcatgg    2100
ggtgtttgta ggagcagcca tgagatctga ggccacagct gctgcagaac acaagggcaa    2160
gatcatcatg cacgaccct ttgccatgcg accttcttc ggctacaact tcggcaaata    2220
cctggcccac tggctgagca tggcccaccg cccagcagcc aagttgccca agatcttcca    2280
tgtcaactgg ttccggaagg acaaagatgg caagttcctc tggccaggct ttggcgagaa    2340
ctcccgggtg ctggagtgga tgttcgggcg gattgaaggg gaagacagcg ccaagctcac    2400
gcccatcggc tacatcccta aggaaaacgc cttgaacctg aaaggcctgg ggcgtcaa    2460 cgtggaggag ctgtttggga tctctaagga gttctgggag aaggaggtgg aggagatcga    2520
caggtatctg gaggaccagg tcaacaccga cctcccttac gaaattgaga gggagctccg    2580
agccctgaaa cagagaatca gccagatgta agaattcacc ggtcgacacc ggtgatatct    2640
cgagtgcttt atttgtgaaa tttgtgatac tattgcttta tttgtaacca ttataagctg    2700
caataaacaa gttaacaaca acaattgcat tcatttttatt gttttcaggt tcaggggagg    2760
tgtgggaggt tttttaaagg gggagggggt acgtagataa gtagcatggc gggttaatca    2820
```

```
ttaactacaa ggaacccta gtgatggagt tggccactcc ctctctgcgc gctcgctcgc    2880
tcactgaggc cgggcgacca aaggtcgccc gacgcccggg cttttgcccgg gcggcctcag   2940 tgagcgagcg agcgcgccag ctggcgtaat agcgaagagg cccgcaccga tcgcccttcc   3000
caacagttgc gcagcctgaa tggcgaatgg cgattctgtt gcaatggctg gcggtaatat   3060
tgttctggat attaccagca aggccgatag tttgagttct tctactcagg caagtgatgt   3120
tattactaat caaagaagta ttgcgacaac ggttaatttg cgtgatggac agactctttt   3180
actcggtggc ctcactgatt ataaaaacac ttctcaggat tctggcgtac cgttcctgtc   3240
taaaatccct ttaatcggcc tcctgtttag ctcccgctct gattctaacg aggaaagcac   3300
gttatacgtg ctcgtcaaag caaccatagt acgcgccctg tagcggcgca ttaagcgcgg   3360
cgggtgtggt ggttacgcgc agcgtgaccg ctacacttgc cagcgcccta gcgcccgctc   3420 cttttcgcttt cttcccttcc tttctcgcca cgttcgccgg ctttccccgt caagctctaa   3480
atcgggggct cccttaggg ttccgattta gtgctttacg gcacctcgac cccaaaaaac   3540
ttgattaggg tgatggttca cgtagtgggc catcgccctg atagacggtt tttcgccctt   3600
tgacgttgga gtccacgttc tttaatagtg actcttgtt ccaaactgga acaacactca    3660
accctatctc ggtctattct tttgatttat aagggatttt gccgatttcg gcctattggt   3720
taaaaaatga gctgatttaa caaaaattta acgcgaattt taacaaaata ttaacgttta   3780
caatttaaat atttgcttat acaatcttcc tgttttttggg gcttttctga ttatcaaccg   3840
gggtacatat gattgacatg ctagttttac gattaccgtt catcgattct cttgtttgct   3900
ccagactctc aggcaatgac ctgatagcct ttgtagagac ctctcaaaaa tagctaccct   3960
ctccggcatg aatttatcag ctagaacggt tgaatatcat attgatggtg atttgactgt   4020
ctccggcctt tctcacccgt ttgaatcttt acctacacat tactcaggca ttgcatttaa   4080
aatatatgag ggttctaaaa attttttatcc ttgcgttgaa ataaaggctt ctcccgcaaa   4140
agtattacag ggtcataatg ttttttggtac aaccgattta gctttatgct ctgaggcttt   4200
attgcttaat tttgctaatt ctttgccttg cctgtatgat ttattggatg ttggaatgcc   4260
ctgatgcggt attttctcct tacgcatctg tgcggtattt cacaccgcat atggtgcact   4320
ctcagtacaa tctgctctga tgccgcatag ttaagccagc cccgacaccc gccaacaccc   4380
gctgacgcgc cctgacgggc ttgtctgctc ccggcatccg cttacagaca agctgtgacc   4440
gtctccggga gctgcatgtg tcagaggttt tcaccgtcat caccgaaacg cgcgagacga   4500
aagggcctcg tgatacgcct attttttatag gttaatgtca tgataataat ggtttcttag   4560
acgtcaggtg cacttttcg gggaaatgtg cgcggaaccc ctatttgttt attttttctaa   4620 atacattcaa atatgtatcc gctcatgaga caataaccct gataaatgct tcaataatat   4680 tgaaaagga agagtatgag tattcaacat ttccgtgtcg cccttattcc cttttttgcg    4740 gcatttttgcc ttcctgtttt tgctcaccca gaaacgctgg tgaaagtaaa agatgctgaa   4800
gatcagttgg gtgcacgagt gggttacatc gaactggatc tcaacagcgg taagatcctt   4860
gagagttttc gccccgaaga acgttttcca atgatgagca cttttaaagt tctgctatgt   4920
ggcgcggtat tatcccgtat tgacgccggg caagagcaac tcggtcgccg catacactat   4980
tctcagaatg acttggttga gtactcacca gtcacagaaa agcatcttac ggatggcatg   5040
acagtaagag aattatgcag tgctgccata accatgagtg ataacactgc ggccaactta   5100
cttctgacaa cgatcggagg accgaaggag ctaaccgctt ttttgcacaa catgggggat   5160
```

```
catgtaactc gccttgatcg ttgggaaccg gagctgaatg aagccatacc aaacgacgag    5220
cgtgacacca cgatgcctgt agcaatggca acaacgttgc gcaaactatt aactggcgaa    5280
ctacttactc tagcttcccg gcaacaatta atagactgga tggaggcgga taaagttgca    5340
ggaccacttc tgcgctcggc ccttccggct ggctggttta ttgctgataa atctggagcc    5400
ggtgagcgtg gtctcgcgg tatcattgca gcactggggc cagatggtaa gccctcccgt    5460
atcgtagtta tctacacgac ggggagtcag gcaactatgg atgaacgaaa tagacagatc    5520
gctgagatag gtgcctcact gattaagcat tggtaactgt cagaccaagt ttactcatat    5580
atactttaga ttgatttaaa acttcatttt taatttaaaa ggatctaggt gaagatcctt    5640
tttgataatc tcatgaccaa aatcccttaa cgtgagtttt cgttccactg agcgtcagac    5700
cccgtagaaa agatcaaagg atcttcttga gatcctttt ttctgcgcgt aatctgctgc    5760
ttgcaaacaa aaaaccacc gctaccagcg gtggtttgtt tgccggatca agagctacca    5820 actcttttc cgaaggtaac tggcttcagc agagcgcaga taccaaatac tgtccttcta    5880
gtgtagccgt agttaggcca ccacttcaag aactctgtag caccgcctac atacctcgct    5940
ctgctaatcc tgttaccagt ggctgctgcc agtggcgata gtcgtgtct taccgggttg    6000 gactcaagac gatagttacc ggataagcg cagcggtcgg gctgaacggg gggttcgtgc    6060
acacagccca gcttggagcg aacgacctac accgaactga gatacctaca gcgtgagcta    6120
tgagaaagcg ccacgcttcc cgaagggaga aaggcggaca ggtatccggt aagcggcagg    6180
gtcggaacag gagagcgcac gagggagctt ccaggggaa acgcctggta tctttatagt    6240
cctgtcgggt ttcgccacct ctgacttgag cgtcgatttt tgtgatgctc gtcagggggg    6300
cggagcctat ggaaaaacgc cagcaacgcg gccttttac ggttcctggc cttttgctgg    6360
ccttttgctc acatgttctt tcctgcgtta tcccctgatt ctgtggataa ccgtattacc    6420
gcctttgagt gagctgatac cgctcgccgc agccgaacga ccgagcgcag cgagtcagtg    6480
agcgaggaag cggaagagcg cccaatacgc aaaccgcctc tccccgcgcg ttggccgatt    6540
cattaatg                                                              6548
```

<210> SEQ ID NO 14
<211> LENGTH: 9888
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120 actagggtt ccttgtagtt aatgattaac ccgccatgct acttatctac gtacatttat     180
attggctcat gtccaacatt accgccatgt tgacattgat tattgactag actttttttt     240
tacctttttg gttcctttgg cttttggct tttggcttcc agggcttctg gatccccccc     300
aaccctcccc atacacatac acatgtgcac tcgtgcactc aacccagcac aggataatgt     360
tcattcttga ccttccaca tacatctggc tatgttctct ctcttatcta caataaatct     420
cctccactat acttaggagc agttatgttc ttcttcttc tttctttttt ttttttttca     480
ttcagtaaca tcatcagaat cccctagctc tggcctacct cctcagtaac aatcagctga     540
tccctggcca ctaatctgta ctcactaatc tgttttccaa actcttggcc cctgagctaa     600
```

```
ttatagcagt gcttcatgcc acccacccca accctattct tgttctctga ctcccactaa    660
tctacacatt cagaggattg tggatataag aggctgggag gccagcttag caaccagagc    720
tggaggctgc gcggccgcca tgccagagcc agcgaagtct gctcccgccc cgaaaaaggg    780
ctccaagaag gcggtgacta aggcgcagaa gaaagacggc aagaagcgca agcgcagccg    840
caaggagagc tattccatct atgtgtacaa ggttctgaag caggtccacc ctgacaccgg    900
catttcgtcc aaggccatgg gcatcatgaa ttcgtttgtg aacgacattt tcgagcgcat    960
cgcaggtgag gcttcccgcc tggcgcatta caacaagcgc tcgaccatca cctccaggga   1020
gatccagacg gccgtgcgcc tgctgctgcc tggggagttg gccaagcacg ccgtgtccga   1080
gggtactaag gccatcacca agtacaccag cgctaaggat ccaccggtcg ccaccatggt   1140
gagcaagggc gaggagctgt tcaccggggt ggtgcccatc ctggtcgagc tggacggcga   1200
cgtaaacggc cacaagttca gcgtgtccgg cgagggcgag ggcgatgcca cctacggcaa   1260
gctgaccctg aagttcatct gcaccaccgg caagctgccc gtgccctggc ccaccctcgt   1320
gaccaccctg acctacggcg tgcagtgctt cagccgctac cccgaccaca tgaagcagca   1380
cgacttcttc aagtccgcca tgcccgaagg ctacgtccag agcgcacca tcttcttcaa    1440 ggacgacggc aactacaaga cccgcgccga ggtgaagttc gagggcgaca ccctggtgaa   1500
ccgcatcgag ctgaagggca tcgacttcaa ggaggacggc aacatcctgg ggcacaagct   1560
ggagtacaac tacaacagcc acaacgtcta tatcatggcc gacaagcaga gaacggcat    1620 caaggtgaac ttcaagatcc gccacaacat cgaggacggc agcgtgcagc tcgccgacca   1680
ctaccagcag aacaccccca tcggcgacgg ccccgtgctg ctgcccgaca ccactacct    1740 gagcacccag tccgccctga caaagaccc caacgagaag cgcgatcaca tggtcctgct   1800
ggagttcgtg accgccgccg ggatcactct cggcatggac gagctgtaca gtaaacaat    1860 tccgcccctc tcctccccc ccccctaacg ttactggccg aagccgcttg gaataaggcc    1920
ggtgtgcgtt tgtctatatg ttattttcca ccatattgcc gtcttttggc aatgtgaggg   1980
cccggaaacc tggccctgtc ttcttgacga gcattcctag gggtcttttcc cctctcgcca   2040 aaggaatgca aggtctgttg aatgtcgtga aggaagcagt tcctctggaa gcttcttgaa    2100
gacaaacaac gtctgtagcg acccttttgca ggcagcggaa ccccccacct ggcgacaggt   2160
gcctctgcgg ccaaaagcca cgtgtataag atacacctgc aaaggcggca caaccccagt   2220
gccacgttgt gagttggata gttgtggaaa gagtcaaatg gctctcctca agcgtattca   2280
acaaggggct gaaggatgcc cagaaggtac cccattgtat gggatctgat ctggggcctc   2340
ggtgcacatg ctttacatgt gtttagtcga ggttaaaaaa cgtctaggcc ccccgaacca   2400
cggggacgtg gttttccttt gaaaaacacg atgataagct tgatcacgcg tgccaccatg   2460
gcgaaccatg cgcccttcga aacggatatc agcaccctga cccgcttcgt catggagcag   2520
ggcaggaagg ctcagggcac gggggagttg acccagctgc tgaattcgct ctgcaccgcg   2580
atcaaagcca tctcgtctgc ggtgcgccag gcgggcatcg cacagctcta tggtatcgct   2640
ggctcaacca atgtgactgg ggatcaagta aagaagctgg acatactttc caatgacctg   2700
gtgatcaata tgctgaagtc gtcctacgct acctgtgttc ttgtgtctga agaaaacaca   2760
aatgccatca taatcgaacc tgagaagagg ggcaaatatg ttgtctgttt cgatcccctt   2820
gatggctcat ccaacattga ctgccttgtg tccatcggaa ccattttggg catttacaga   2880
aagaaaagta ctgatgagcc ttctgagaag gatgctctgc agcccggccg ggacctggtg   2940
gcagccgggt atgcgctcta tggcagtgcc accatgttgg tccttgccat ggattgtggt   3000
```

```
gtcaactgct tcatgctgga cccgtccatt ggagaattca ttatggtgga cagggacgtg   3060
aagatgaaga agaaaggtaa catctacagc cttaatgagg gttatgccaa ggactttgac   3120
cctgccatca atgagtatct ccagaggaaa aagttccctc cggatggttc agcccctat    3180
ggtgcccggt atgtggggtc catggtggct gatattcacc gcactctggt atatggaggg   3240
atcttttat accccgccaa caagaaaagc ccaagtggaa agctgcggct gctgtatgag    3300
tgcaacccca tagcttatgt catggagaag gccgtgggc tcgccaccac ggggacaaa     3360
gatatattag acatcgttcc caccgagatc caccagaagg caccagtcgt catggggtcc   3420
tctgaagatg tgcaggagtt cctggagatc tacaggaagc acaaagccaa gtgactcgac   3480
cgattctaga ctccctcccc cccccctaac gttactggcc gaagccgctt ggaataaggc   3540
cggtgtgcgt ttgtctatat gttattttcc accatattgc cgtcttttgg caatgtgagg   3600
gcccggaaac ctggccctgt cttcttgacg agcattccta ggggtctttc ccctctcgcc   3660
aaaggaatgc aaggtctgtt gaatgtcgtg aaggaagcag ttcctctgga gcttcttga    3720
agacaaacaa cgtctgtagc gacccttgc aggcagcgga acccccacc tggcgacagg     3780
tgcctctgcg gccaaaagcc acgtgtataa gatacacctg caaaggcggc acaaccccag   3840
tgccacgttg tgagttggat agttgtggaa agagtcaaat ggctctcctc aagcgtattc   3900
aacaaggggc tgaaggatgc ccagaaggta ccccattgta tgggatctga tctgggcct    3960
cggtgcacat gctttacgtg tgtttagtcg aggttaaaaa acgtctaggc ccccccgaacc  4020
acggggacgt ggttttcctt tgaaaaacac gatgataata ccatggccat gcctcctcag   4080
ctgcataacg gtctggactt ctctgccaag gtcatccagg gcagcctcga cagcctgccc   4140
caggcagtga ggaagttcgt ggaaggcaat gctcagctgt gccagccgga gtatatccac   4200
atctgcgatg gctccgagga ggagtacggg cagttgctga cccacatgca ggaggagggt   4260
gtcatccgca agctgaagaa atatgacaac tgttggctgg ctctcactga ccctcgagat   4320
gtggccagga tcgaaagcaa gacagtcatc atcacccaag agcagagaga cacagtgccc   4380
atccccaaaa ctggcctcag ccagctgggc cgctggatgt cggaagagga ctttgagaaa   4440
gcattcaacg ccaggttccc agggtgcatg aaaggccgca ccatgtatgt catcccattc   4500
agcatggggc cactgggctc gccgctggcc aagattggta ttgaactgac agactcgccc   4560
tatgtggtgg ccagcatgcg gatcatgact cggatgggca tatctgtgct ggaggccctg   4620
ggagatgggg agttcatcaa gtgcctgcac tctgtggggt gccctctccc cttaaaaaag   4680
cctttggtca caactgggc ctgcaaccct gagctgaccc tgatcgccca cctcccggac    4740
cgcagagaga tcatctcctt tggaagcgga tatggtggga actcactact cgggaagaaa   4800
tgctttgcgt tgcggatcgc cagccgtctg gctaaggagg aagggtggct ggcggagcat   4860
atgctgatcc tgggcataac taaccccgaa ggcaagaaga aatacctggc cgcagccttc   4920
cctagtgcct gtgggaagac caacttggcc atgatgaacc ccagcctgcc cgggtggaag   4980
gtcgaatgtg tgggcgatga catcgcctgg atgaagtttg atgcccaagg caacttaagg   5040
gctatcaacc cagaaaacgg gttttttgga gttgctcctg gcacctcagt gaagacaaat   5100
ccaaatgcca ttaaaaccat ccagaaaaac accatcttca ccaacgtggc tgagactagc   5160
gatggggtg tttactggga aggcatcgat gagccgctgg ccccgggagt caccatcacc    5220
tcctggaaga acaaggagtg gagaccgcag gacgcggaac catgtgccca tcccaactcg   5280
agattctgca cccctgccag ccagtgcccc attattgacc ctgcctggga atctccagaa   5340
```

```
ggagtaccca ttgagggtat catctttggt ggccgtagac ctgaaggtgt cccccttgtc  5400
tatgaagccc tcagctggca gcatggggtg tttgtaggag cagccatgag atctgaggcc  5460
acagctgctg cagaacacaa gggcaagatc atcatgcacg accccttgtc catgcgaccc  5520
ttcttcggct acaacttcgg caaatacctg gcccactggc tgagcatggc caccgccca   5580
gcagccaagt tgcccaagat cttccatgtc aactggttcc ggaaggacaa agatggcaag  5640
ttcctctggc caggctttgg cgagaactcc cgggtgctgg agtggatgtt cgggcggatt  5700
gaaggggaag acagcgccaa gctcacgccc atcggctaca tccctaagga aaacgccttg  5760
aacctgaaag gcctgggggg cgtcaacgtg gaggagctgt ttgggatctc taaggagttc  5820
tgggagaagg aggtggagga atcgacagg tatctggagg accaggtcaa caccgacctc   5880
ccttacgaaa ttgagaggga gctccgagcc ctgaaacaga gaatcagcca gatgtaagcg  5940
gccgctctag aggatccaag cttatcgata ccgtcgacct cgagtgcttt atttgtgaaa  6000
tttgtgatac tattgcttta tttgtaacca ttataagctg caataaacaa gttaacaaca  6060
acaattgcat tcattttatt gtttcaggtt caggggagg tgtgggaggt ttttaaagg    6120
gggaggggt acgtagataa gtagcatggc gggttaatca ttaactacaa ggaacccta    6180
gtgatggagt tggccactcc ctctctgcgc gctcgctcgc tcactgaggc cgggcgacca  6240
aaggtcgccc gacgcccggg ctttgcccgg gcggcctcag tgagcgagcg agcgcgccag  6300
ctggcgtaat agcgaagagg cccgcaccga tcgcccttcc caacagttgc gcagcctgaa  6360
tggcgaatgg cgattctgtt gcaatggctg gcggtaatat tgttctggat attaccagca  6420
aggccgatag tttgagttct tctactcagg caagtgatgt tattactaat caaagaagta  6480
ttgcgacaac ggttaatttg cgtgatggac agactctttt actcggtggc ctcactgatt  6540
ataaaaacac ttctcaggat tctggcgtac cgttcctgtc taaatccct ttaatcggcc    6600
tcctgtttag ctcccgctct gattctaacg aggaaagcac gttatacgtg ctcgtcaaag  6660
caaccatagt acgcgccctg tagcggcgca ttaagcgcgg cgggtgtggt ggttacgcgc  6720
agcgtgaccg ctacacttgc cagcgcccta gcgcccgctc ctttcgcttt cttcccttcc  6780
tttctcgcca cgttcgccgg ctttccccgt caagctctaa atcggggggct ccctttaggg 6840
ttccgattta gtgctttacg gcacctcgac cccaaaaaac ttgattaggg tgatggttca  6900
cgtagtgggc catcgccctg atagacggtt tttcgccctt tgacgttgga gtccacgttc  6960
tttaatagtg gactcttgtt ccaaactgga acaacactca accctatctc ggtctattct  7020
tttgatttat aagggatttt gccgatttcg gcctattggt taaaaatga gctgatttaa    7080
caaaaattta acgcgaattt taacaaaata ttaacgttta caatttaaat atttgcttat   7140
acaatcttcc tgttttttggg cttttctga ttatcaaccg gggtacatat gattgacatg   7200
ctagttttac gattaccgtt catcgattct cttgtttgct ccagactctc aggcaatgac  7260
ctgatagcct ttgtagagac ctctcaaaaa tagctaccct ctccggcatg aatttatcag  7320
ctagaacggt tgaatatcat attgatggtg atttgactgt ctccggcctt tctcacccgt  7380
ttgaatcttt acctacacat tactcaggca ttgcatttaa aatatatgag ggttctaaaa  7440
attttattatcc ttgcgttgaa ataaaggctt ctccccgcaaa agtattacag ggtcataatg 7500
tttttggtac aaccgattta gctttatgct ctgaggcttt attgcttaat tttgctaatt  7560
ctttgccttg cctgtatgat ttattggatg ttggaatgcc ctgatgcggt attttctcct  7620
tacgcatctg tgcggtattt cacaccgcat atggtgcact ctcagtacaa tctgctctga  7680
tgccgcatag ttaagccagc cccgacaccc gccaacaccc gctgacgcgc cctgacgggc  7740
```

-continued

```
ttgtctgctc ccggcatccg cttacagaca agctgtgacc gtctccggga gctgcatgtg    7800
tcagaggttt tcaccgtcat caccgaaacg cgcgagacga aagggcctcg tgatacgcct    7860
atttttatag gttaatgtca tgataataat ggtttcttag acgtcaggtg cacttttcg     7920
gggaaatgtg cgcggaaccc ctatttgttt attttcttaa atacattcaa atatgtatcc    7980
gctcatgaga caataaccct gataaatgct tcaataatat tgaaaaagga agagtatgag    8040
tattcaacat ttccgtgtcg cccttattcc cttttttgcg gcattttgcc ttcctgtttt    8100
tgctcaccca gaaacgctgg tgaaagtaaa agatgctgaa gatcagttgg gtgcacgagt    8160
gggttacatc gaactggatc tcaacagcgg taagatcctt gagagttttc gccccgaaga    8220
acgttttcca atgatgagca cttttaaagt tctgctatgt ggcgcggtat tatcccgtat    8280
tgacgccggg caagagcaac tcggtcgccg catacactat tctcagaatg acttggttga    8340
gtactcacca gtcacagaaa agcatcttac ggatggcatg acagtaagag aattatgcag    8400
tgctgccata accatgagtg ataacactgc ggccaactta cttctgacaa cgatcggagg    8460
accgaaggag ctaaccgctt ttttgcacaa catgggggat catgtaactc gccttgatcg    8520
ttgggaaccg gagctgaatg aagccatacc aaacgacgag cgtgacacca cgatgcctgt    8580
agcaatggca acaacgttgc gcaaactatt aactggcgaa ctacttactc tagcttcccg    8640
gcaacaatta atagactgga tggaggcgga taaagttgca ggaccacttc tgcgctcggc    8700
ccttccggct ggctggttta ttgctgataa atctggagcc ggtgagcgtg gtctcgcgg    8760
tatcattgca gcactggggc cagatggtaa gccctcccgt atcgtagtta tctacacgac    8820
ggggagtcag gcaactatgg atgaacgaaa tagacagatc gctgagatag gtgcctcact    8880
gattaagcat tggtaactgt cagaccaagt ttactcatat atactttaga ttgatttaaa    8940
acttcatttt taatttaaaa ggatctaggt gaagatcctt tttgataatc tcatgaccaa    9000
aatcccttaa cgtgagtttt cgttccactg agcgtcagac cccgtagaaa agatcaaagg    9060
atcttcttga tcctttttt tctgcgcgt aatctgctgc ttgcaaacaa aaaaaccacc    9120
gctaccagcg gtggtttgtt tgccggatca agagctacca actctttttc cgaaggtaac    9180
tggcttcagc agagcgcaga taccaaatac tgtccttcta gtgtagccgt agttaggcca    9240
ccacttcaag aactctgtag caccgcctac atacctcgct ctgctaatcc tgttaccagt    9300
ggctgctgcc agtggcgata agtcgtgtct taccgggttg gactcaagac gatagttacc    9360
ggataaggcg cagcggtcgg gctgaacggg gggttcgtgc acacagccca gcttggagcg    9420
aacgacctac accgaactga gatacctaca gcgtgagcta tgagaaagcg ccacgcttcc    9480
cgaagggaga aaggcggaca ggtatccggt aagcggcagg gtcggaacag gagagcgcac    9540
gagggagctt ccagggggaa acgcctggta tctttatagt cctgtcgggt ttcgccacct    9600
ctgacttgag cgtcgatttt tgtgatgctc gtcaggggg cggagcctat ggaaaaacgc    9660
cagcaacgcg gcctttttac ggttcctggc cttttgctgg ccttttgctc acatgttctt    9720
tcctgcgtta tcccctgatt ctgtggataa ccgtattacc gcctttgagt gagctgatac    9780
cgctcgccgc agccgaacga ccgagcgcag cgagtcagtg agcgaggaag cggaagagcg    9840
cccaatacgc aaaccgcctc tccccgcgcg ttggccgatt cattaatg                 9888
```

<210> SEQ ID NO 15
<211> LENGTH: 5098
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 15

```
cagctgcgcg ctcgctcgct cactgaggcc gcccgggcaa agcccgggcg tcgggcgacc        60
tttggtcgcc cggcctcagt gagcgagcga gcgcgcagag agggagtggc caactccatc       120
actaggggtt ccttgtagtt aatgattaac ccgccatgct acttatctac gtacatttat       180
attggctcat gtccaacatt accgccatgt tgacattgat tattgactag acttttttt        240
tacctttttg gttcctttgg ccttttggct tttggcttcc agggcttctg gatcccccc        300
aaccctccc atacacatac acatgtgcac tcgtgcactc aacccagcac aggataatgt        360
tcattcttga cctttccaca tacatctggc tatgttctct ctcttatcta caataaatct       420
cctccactat acttaggagc agttatgttc ttcttctttc tttctttttt ttttttttca       480
ttcagtaaca tcatcagaat cccctagctc tggcctacct cctcagtaac aatcagctga       540
tccctggcca ctaatctgta ctcactaatc tgttttccaa actcttggcc cctgagctaa       600
ttatagcagt gcttcatgcc acccacccca accctattct tgttctctga ctcccactaa       660
tctacacatt cagaggattg tggatataag aggctgggag gccagcttag caaccagagc       720
tggaggctgc gcggccgcgg acgcgtgcca ccatggcgaa ccatgcgccc ttcgaaacgg       780
atatcagcac cctgacccgc ttcgtcatgg agcagggcag gaaggctcag ggcacggggg       840
agttgaccca gctgctgaat tcgctctgca ccgcgatcaa agccatctcg tctgcggtgc       900
gccaggcggg catcgcacag ctctatggta tcgctggctc aaccaatgtg actggggatc       960
aagtaaagaa gctggacata ctttccaatg acctggtgat caatatgctg aagtcgtcct      1020
acgctacctg tgttcttgtg tctgaagaaa acacaaatgc catcataatc gaacctgaga      1080
agaggggcaa atatgttgtc tgtttcgatc cccttgatgg ctcatccaac attgactgcc      1140
ttgtgtccat cggaaccatt tttgcatttt acagaaagaa aagtactgat gagccttctg      1200
agaaggatgc tctgcagccc ggccgggacc tggtggcagc cgggtatgcg ctctatggca      1260
gtgccaccat gttggtcctt gccatggatt gtggtgtcaa ctgcttcatg ctggacccgt      1320
ccattggaga attcattatg gtggacaggg acgtgaagat gaagaagaaa ggtaacatct      1380
acagccttaa tgagggttat gccaaggact tgaccctgc catcaatgag tatctccaga      1440
ggaaaaagtt ccctccggat ggttcagccc cctatggtgc ccgtatgtg gggtccatgg       1500
tggctgatat tcaccgcact ctggtatatg gagggatctt tttatacccc gccaacaaga      1560
aaagcccaag tggaaagctg cggctgctgt atgagtgcaa ccccatagct tatgtcatgg      1620
agaaggccgg tgggctcgcc accacggggg acaaagatat attagacatc gttcccaccg      1680
agatccacca gaaggcacca gtcgtcatgg ggtcctctga agatgtgcag gagttcctgg      1740
agatctacag gaagcacaaa gccaagtgac tcgagtgctt tatttgtgaa atttgtgata      1800
ctattgcttt atttgtaacc attataagct gcaataaaca agttaacaac aacaattgca      1860
ttcattttat tgtttcaggt tcagggggag gtgtgggagg tttttaaag ggggagggg       1920
tacgtagata agtagcatgg cgggttaatc attaactaca aggaacccct agtgatggag      1980
ttggccactc cctctctgcg cgctcgctcg ctcactgagg ccgggcgacc aaaggtcgcc      2040
cgacgcccgg gctttgcccg ggcggcctca gtgagcgagc gagcgcgcca gctggcgtaa      2100
tagcgaagag gcccgcaccg atcgcccttc ccaacagttg cgcagcctga atggcgaatg      2160
gcgattctgt tgcaatggct ggcggtaata ttgttctgga tattaccagc aaggccgata      2220
```

```
gtttgagttc ttctactcag gcaagtgatg ttattactaa tcaaagaagt attgcgacaa    2280
cggttaattt gcgtgatgga cagactcttt tactcggtgg cctcactgat tataaaaaca    2340
cttctcagga ttctggcgta ccgttcctgt ctaaaatccc tttaatcggc ctcctgttta    2400
gctcccgctc tgattctaac gaggaaagca cgttatacgt gctcgtcaaa gcaaccatag    2460
tacgcgccct gtagcggcgc attaagcgcg gcgggtgtgg tggttacgcg cagcgtgacc    2520
gctacacttg ccagcgccct agcgcccgct cctttcgctt tcttcccttc ctttctcgcc    2580
acgttcgccg gctttccccg tcaagctcta atcggggggc tcccttta gg gttccgattt    2640 agtgctttac ggcacctcga ccccaaaaaa cttgattagg gtgatggttc acgtagtggg    2700
ccatcgccct gatagacggt ttttcgccct ttgacgttgg agtccacgtt ctttaatagt    2760
ggactcttgt tccaaactgg aacaacactc aaccctatct cggtctattc ttttgattta    2820
taagggattt tgccgatttc ggcctattgg ttaaaaaatg agctgattta acaaaaattt    2880
aacgcgaatt ttaacaaaat attaacgttt acaatttaaa tatttgctta tacaatcttc    2940
ctgtttttgg ggcttttctg attatcaacc ggggtacata tgattgacat gctagtttta    3000
cgattaccgt tcatcgattc tcttgtttgc tccagactct caggcaatga cctgatagcc    3060
tttgtagaga cctctcaaaa atagctaccc tctccggcat gaatttatca gctagaacgg    3120
ttgaatatca tattgatggt gatttgactg tctccggcct ttctcacccg tttgaatctt    3180
tacctacaca ttactcaggc attgcattta aaatatatga gggttctaaa aattttttatc   3240 cttgcgttga aataaaggct tctcccgcaa agtattaca gggtcataat gttttttggta    3300 caaccgattt agctttatgc tctgaggctt tattgcttaa ttttgctaat tctttgcctt    3360
gcctgtatga tttattggat gttggaatgc cctgatgcgg tatttctcc ttacgcatct    3420 gtgcggtatt tcacaccgca tatggtgcac tctcagtaca atctgctctg atgccgcata    3480
gttaagccag ccccgacacc cgccaacacc cgctgacgcg ccctgacggg cttgtctgct    3540
cccggcatcc gcttacagac aagctgtgac cgtctccggg agctgcatgt gtcagaggtt    3600
ttcaccgtca tcaccgaaac gcgcgagacg aaagggcctc gtgatacgcc tatttttata    3660
ggttaatgtc atgataataa tggtttctta gacgtcaggt ggcactttc ggggaaatgt     3720 gcgcggaacc cctatttgtt tattttccta aatacattca aatatgtatc cgctcatgag    3780
acaataaccc tgataaatgc ttcaataata ttgaaaaagg aagagtatga gtattcaaca    3840
tttccgtgtc gcccttattc cctttttttgc ggcatttttgc cttcctgttt ttgctcaccc   3900
agaaacgctg gtgaaagtaa aagatgctga agatcagttg ggtgcacgag tgggttacat    3960
cgaactggat ctcaacagcg gtaagatcct tgagagtttt cgccccgaag aacgttttcc    4020
aatgatgagc acttttaaag ttctgctatg tggcgcggta ttatcccgta ttgacgccgg    4080
gcaagagcaa ctcggtcgcc gcatacacta ttctcagaat gacttggttg agtactcacc    4140
agtcacagaa aagcatctta cggatggcat gacagtaaga gaattatgca gtgctgccat    4200
aaccatgagt gataacactg cggccaactt acttctgaca acgatcggag gaccgaagga    4260
gctaaccgct ttttttgcaca acatggggga tcatgtaact cgccttgatc gttgggaacc    4320
ggagctgaat gaagccatac caaacgacga gcgtgacacc acgatgcctg tagcaatggc    4380
aacaacgttg cgcaaactat taactggcga actacttact ctagcttccc ggcaacaatt    4440
aatagactgg atggaggcgg ataaagttgc aggaccactt ctgcgctcgg cccttccggc    4500
tggctggttt attgctgata aatctggagc cggtgagcgt gggtctcgcg gtatcattgc    4560
agcactgggg ccagatggta agccctcccg tatcgtagtt atctacacga cggggagtca    4620
```

```
ggcaactatg gatgaacgaa atagacagat cgctgagata ggtgcctcac tgattaagca    4680
ttggtaactg tcagaccaag tttactcata tatactttag attgatttaa aacttcattt    4740
ttaatttaaa aggatctagg tgaagatcct ttttgataat ctcatgacca aaatccctta    4800
acgtgagttt tcgttccact gagcgtcaga ccccgtagaa aagatcaaag gatcttcttg    4860 agatccttt tttctgcgcg taatctgctg cttgcaaaca aaaaaaccac cgctaccagc    4920
ggtggtttgt ttgccggatc aagagctacc aactcttttt ccgaaggtaa ctggcttcag    4980
cagagcgcag ataccaaata ctgtccttct agtgtagccg tagttaggcc accacttcaa    5040
gaactctgta gcaccgccta catacctcgc tctgctaatc ctgttaccag tggctgct     5098
```

<210> SEQ ID NO 16
<211> LENGTH: 8216
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt ccttgtagtt aatgattaac ccgccatgct actatctac gtacatttat      180 attggctcat gtccaacatt accgccatgt tgacattgat tattgactag actttttttt     240
tacctttttg gttcctttgg cctttggct tttggcttcc agggcttctg gatcccccc       300 aacccctccc atacacatac acatgtgcac tcgtgcactc aacccagcac aggataatgt     360
tcattcttga cctttccaca tacatctggc tatgttctct ctcttatcta caataaatct     420
cctccactat acttaggagc agttatgttc ttcttcttc tttctttttt tttttttca      480 ttcagtaaca tcatcagaat cccctagctc tggcctacct cctcagtaac aatcagctga     540
tccctggcca ctaatctgta ctcactaatc tgttttccaa actcttggcc cctgagctaa     600
ttatagcagt gcttcatgcc acccacccca accctattct tgttctctga ctcccactaa     660
tctacacatt cagaggattg tggatataag aggctgggag gccagcttag caaccagagc     720
tggaggctgc gcggccgcca ccatgctgaa gttccaaaca gttcgagggg gcctgaggct     780
cctgggtgtc cgccgatcct cctcggcccc tgttgcctcc ccaaatgtcc ggcgtctgga     840
gtataagcct atcaagaaag taatggtggc caacagaggt gagattgcca tccgagtgtt     900
tcgtgcgtgc acagagctgg gtatccgcac agtggctgtc tactcggagc aggacacagg     960
gcagatgcac aggcagaaag ctgatgaagc ctaccttatt ggccgtggcc tggcacctgt    1020
gcaggcctac ctgcacattc agacatcat caaggtggcc aaggaaaatg gtgtagatgc    1080
ggtgcatcct ggctatgggt tcctctcaga gcgagcagac tttgcccagg cctgccaaga    1140
tgctggagtc cggttcattg gtccaagccc agaggtggtc cgcaagatgg agacaaggt    1200 ggaagcccgg gccattgcca tcgctgcagg cgttccagtg gtccccggca cggactcccc    1260
catcagctcc ctgcacgagg cgcatgagtt ctccaacacc ttcggcttcc ctattatctt    1320
caaggccgcc tacggaggtg gggccgcgg catgcgggtc gtgcatagct atgaggagtt    1380
ggaagagaat tacacccggg cctactccga ggccttggca gcctttggga atggagcgtt    1440
gtttgtggag aagttcattg agaagccaag gcacattgag gtgcagatcc taggggacca    1500
gtatgggaac atcctgcacc tgtacgagcg agactgctcc atccagcgtc ggcaccagaa    1560
```

```
ggtggtagag atcgccctg ctacccacct ggatccccaa cttcgctcac gtctcaccag    1620
tgactctgtc aaacttgcca agcaggtagg ctatgagaac gccggcactg tggagttcct    1680
ggtggacaag cacggcaagc actacttcat cgaggtcaat tcccgcctgc aggtggagca    1740
cacggtcacc gaggagatca cagatgtgga cctggtccat gctcagatcc acgtgtccga    1800
aggccggagc ctgcctgacc tgggcctgcg gcaggagaac atccgcatca atggctgtgc    1860
cattcagtgt cgggtcacca ccgaggaccc tgcacgcagc ttccagccag acaccggccg    1920
cattgaggtt ttccggagtg gtgagggcat gggcatccgc ctggacaacg cctctgcatt    1980
ccagggcgct gtcatatcgc cccactatga ctctctgctc gtcaaggtca ttgcacacgg    2040
caaagaccac cccacagctg ccaccaagat gagcagagcc ctggccgagt ccgtgtccg    2100 aggtgtaaag accaacatcc ccttcctgca gaatgttctc aacaaccagc agttcctggc    2160
aggcacagtg gacacccagt tcatcgatga gaaccctgag ctgttccagc ttcggcctgc    2220
acagaaccgg gcccagaagt tgctacatta cctcggacat gtcatggtga atggccctac    2280
cactccaatc cctgtcaatg tgagccccag tcctgtggat cctgctgttc ctgtggtgcc    2340
cataggccca cctccagctg gtttcaggga catccttctg cgagaagggc cagagggctt    2400
tgcccgagct gtgcggaatc accaggggct gctgttgatg acacaacct tccgggatgc    2460 ccaccagtca ctactggcca ctagagtgcg cacacatgat ctcaaaaaga ttgcgcccta    2520
tgttgcccac aacttcaaca agctcttcag catggagaac tggggaggcg ccacgttcga    2580
cgttgccatg cgcttcctgt acgagtgccc ctggcggcgg ctccaggagc tccgggagct    2640
tatcccgaac atcccgttcc agatgctact gagggggcc aatgctgtgg gctacaccaa    2700
ctaccctgac aacgtggtct tcaagttctg tgaggtggcc aaagagaatg gtatggacgt    2760
cttccgagtc tttgactccc tcaactactt gccaaacatg ctgctgggca tggaagcagc    2820
aggcagtgct ggggggtgtg tggaggctgc catctcatac acggggacg tggctgaccc    2880 tagtcgcact aaatactcac tggagtacta catgggctta gctgaagaac tggtgcgagc    2940
tggcactcac atcctgtgca ttaaggacat ggcgggcctg ctgaagcctg ccgcctgcac    3000
catgctggtc agctccctcc gggaccgatt ccccgacctc ccactgcaca tccataccca    3060
tgatacatca ggggcaggtg tggcagccat gctggcctgt gcacaagcag ggctgatgt    3120 tgtggacgtg gcagtagact ccatgtctgg gatgacctca cagccaagca tggggccct    3180 ggtggcctgt accaaaggga ctccttgga cacagaggta cccctggagc gtgtgtttga    3240
ctacagtgag tactgggaag gggctcgggg actgtacgca gccttcgatt gcacggctac    3300
catgaagtct ggcaactccg acgtgtatga gaatgagatt ccagggggcc agtacaccaa    3360
cctgcacttc caggcccata gcatgggct tggctccaag ttcaaggagg tcaagaaggc    3420
ctatgtggag gctaaccaga tgctggggga cctcatcaag gtgacaccat cctccaagat    3480 tgtggggac ctggcccagt tcatggtgca gaatggttg agccgggcag aggcagaagc    3540
tcaggcagaa gagctgtcct tcccccgctc tgtggtggag ttcctgcagg gctacattgg    3600
cattccccat ggggtttcc ctgagcccytt tcgctctaag gtgctaaagg acctgccaag    3660
aatagagggg cggcctggag cctccctccc tcccctgaac ctgaaggagc tggagaagga    3720
cctgattgat aggcatgggg aggaggtgac cccagaggac gtcctctctg cagccatgta    3780
ccctgatgtc tttgctcaat tcaaagactt cacggctacc ttcggccccc tggatagcct    3840
taatactcgt ctctttcttc aaggacccaa aattgcagag gagtttgagg ttgagctgga    3900
```

```
acggggcaag accctgcaca tcaaagccct ggctgtaagc gacctgaacc gtgctggcca    3960
gaggcaggtg ttctttgaac tcaatgggca gcttcgatcc attctggtta aagacaccca    4020
ggccatgaag gagatgcact tccatcccaa ggctttgaag gatgtgaagg gccaaattgg    4080
ggccccgatg cctgggaagg tcatagacat caaggtggca gcagggggaca aggtggctaa    4140 gggccagccc ctctgtgtgc tcagcgccat gaagatggag actgtggtga cttcgcccat    4200
ggagggcact atccgaaagg ttcatgttac caaggacatg actctggaag gcgacgacct    4260
catcctagag attgagtgag aattcaccgg tcgacaccgg tgatatctcg agtgctttat    4320
ttgtgaaatt tgtgatacta ttgctttatt tgtaaccatt ataagctgca ataaacaagt    4380
taacaacaac aattgcattc attttattgt ttcaggttca gggggaggtg tgggaggttt    4440
tttaaagggg gaggggtac gtagataagt agcatggcgg gttaatcatt aactacaagg    4500 aaccctagt gatggagttg gccactccct ctctgcgcgc tcgctcgctc actgaggccg    4560
ggcgaccaaa ggtcgcccga cgccgggct tgcccgggc ggcctcagtg agcgagcgag    4620
cgcgccagct ggcgtaatag cgaagaggcc cgcaccgatc gcccttccca acagttgcgc    4680
agcctgaatg gcgaatggcg attctgttgc aatggctggc ggtaatattg ttctggatat    4740
taccagcaag gccgatagtt tgagttcttc tactcaggca agtgatgtta ttactaatca    4800
aagaagtatt gcgacaacgg ttaatttgcg tgatggacag actcttttac tcggtggcct    4860
cactgattat aaaaacactt ctcaggattc tggcgtaccg ttcctgtcta aaatcccttt    4920
aatcggcctc ctgtttagct cccgctctga ttctaacgag gaaagcacgt tatacgtgct    4980
cgtcaaagca accatagtac gcgccctgta gcggcgcatt aagcgcggcg ggtgtggtgg    5040
ttacgcgcag cgtgaccgct acacttgcca gcgccctagc gcccgctcct ttcgctttct    5100
tcccttcctt tctcgccacg ttcgccggct ttccccgtca gctctaaat cggggctcc    5160 ctttagggtt ccgatttagt gctttacggc acctcgaccc caaaaaactt gattagggtg    5220
atggttcacg tagtgggcca tcgccctgat agacggtttt tcgccctttg acgttggagt    5280
ccacgttctt taatagtgga ctcttgttcc aaactggaac aacactcaac cctatctcgg    5340
tctattcttt tgatttataa gggattttgc cgatttcggc ctattggtta aaaaatgagc    5400
tgatttaaca aaaatttaac gcgaattta acaaaatatt aacgtttaca atttaaatat    5460
ttgcttatac aatcttcctg ttttggggc tttctgatt atcaaccggg gtacatatga    5520
ttgacatgct agttttacga ttaccgttca tcgattctct tgtttgctcc agactctcag    5580
gcaatgacct gatagccttt gtagagacct ctcaaaaata gctaccctct ccggcatgaa    5640
tttatcagct agaacggttg aatatcatat tgatggtgat ttgactgtct ccggcctttc    5700
tcacccgttt gaatctttac ctacacatta ctcaggcatt gcatttaaaa tatatgaggg    5760
ttctaaaaat ttttatcctt gcgttgaaat aaaggcttct cccgcaaaag tattacaggg    5820
tcataatgtt tttggtacaa ccgatttagc tttatgctct gaggctttat tgcttaattt    5880
tgctaattct ttgccttgcc tgtatgattt attggatgtt ggaatgccct gatgcggtat    5940
tttctcctta cgcatctgtg cggtatttca caccgcatat ggtgcactct cagtacaatc    6000
tgctctgatg ccgcatagtt aagccagccc cgacacccgc caacaccgc tgacgcgccc    6060 tgacgggctt gtctgctccc ggcatccgct tacagacaag ctgtgaccgt ctccgggagc    6120
tgcatgtgtc agaggttttc accgtcatca ccgaaacgcg cgagacgaaa gggcctcgtg    6180
atacgcctat tttataggt taatgtcatg ataataatgg tttcttagac gtcaggtggc    6240
acttttcggg gaaatgtgcg cggaacccct atttgtttat ttttctaaat acattcaaat    6300
```

```
atgtatccgc tcatgagaca ataaccctga taaatgcttc aataatattg aaaaaggaag    6360
agtatgagta ttcaacattt ccgtgtcgcc cttattccct tttttgcggc attttgcctt    6420
cctgtttttg ctcacccaga aacgctggtg aaagtaaaag atgctgaaga tcagttgggt    6480
gcacgagtgg gttacatcga actggatctc aacagcggta agatccttga gagttttcgc    6540
cccgaagaac gttttccaat gatgagcact tttaaagttc tgctatgtgg cgcggtatta    6600
tcccgtattg acgccgggca agagcaactc ggtcgccgca tacactattc tcagaatgac    6660
ttggttgagt actcaccagt cacagaaaag catcttacgg atggcatgac agtaagagaa    6720
ttatgcagtg ctgccataac catgagtgat aacactgcgg ccaacttact tctgacaacg    6780
atcggaggac cgaaggagct aaccgctttt ttgcacaaca tgggggatca tgtaactcgc    6840
cttgatcgtt gggaaccgga gctgaatgaa gccataccaa acgacgagcg tgacaccacg    6900
atgcctgtag caatggcaac aacgttgcgc aaactattaa ctggcgaact acttactcta    6960
gcttcccggc aacaattaat agactggatg gaggcggata aagttgcagg accacttctg    7020
cgctcggccc ttccggctgg ctggtttatt gctgataaat ctggagccgg tgagcgtggg    7080
tctcgcggta tcattgcagc actggggcca gatggtaagc cctcccgtat cgtagttatc    7140
tacacgacgg ggagtcaggc aactatggat gaacgaaata gacagatcgc tgagataggt    7200
gcctcactga ttaagcattg gtaactgtca gaccaagttt actcatatat actttagatt    7260
gatttaaaac ttcatttta atttaaaagg atctaggtga agatcctttt tgataatctc    7320
atgaccaaaa tcccttaacg tgagttttcg ttccactgag cgtcagaccc cgtagaaaag    7380
atcaaaggat cttcttgaga tcctttttt ctgcgcgtaa tctgctgctt gcaaacaaaa    7440
aaaccaccgc taccagcggt ggtttgtttg ccggatcaag agctaccaac tctttttccg    7500
aaggtaactg gcttcagcag agcgcagata ccaaatactg tccttctagt gtagccgtag    7560
ttaggccacc acttcaagaa ctctgtagca ccgcctacat acctcgctct gctaatcctg    7620
ttaccagtgg ctgctgccag tggcgataag tcgtgtctta ccgggttgga ctcaagacga    7680
tagttaccgg ataaggcgca gcggtcgggc tgaacggggg gttcgtgcac acagcccagc    7740
ttggagcgaa cgacctacac cgaactgaga tacctacagc gtgagctatg agaaagcgcc    7800
acgcttcccg aagggagaaa ggcggacagg tatccggtaa gcggcagggt cggaacagga    7860
gagcgcacga gggagcttcc agggggaaac gcctggtatc tttatagtcc tgtcgggttt    7920
cgccacctct gacttgagcg tcgatttttg tgatgctcgt caggggggcg gagcctatgg    7980
aaaaacgcca gcaacgcggc ctttttacgg ttcctggcct tttgctggcc ttttgctcac    8040
atgttctttc ctgcgttatc ccctgattct gtggataacc gtattaccgc ctttgagtga    8100
gctgataccg ctcgccgcag ccgaacgacc gagcgcagcg agtcagtgag cgaggaagcg    8160
gaagagcgcc caatacgcaa accgcctctc cccgcgcgtt ggccgattca ttaatg       8216
```